United States Patent
Gellman et al.

(10) Patent No.: US 7,858,737 B2
(45) Date of Patent: Dec. 28, 2010

(54) HETEROGENEOUS FOLDAMERS CONTAINING α, β, AND/OR γ-AMINO ACIDS

(75) Inventors: Samuel H. Gellman, Madison, WI (US); Ahlke Hayen, Gothenburg (SE); Margaret A. Schmitt, Madison, WI (US); Felix N. Ngassa, East Lansing, MI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 487 days.

(21) Appl. No.: 10/648,089

(22) Filed: Aug. 26, 2003

(65) Prior Publication Data

US 2004/0116654 A1    Jun. 17, 2004

Related U.S. Application Data

(60) Provisional application No. 60/406,006, filed on Aug. 26, 2002.

(51) Int. Cl.
*C07K 1/00* (2006.01)
(52) U.S. Cl. .................................................... 530/300
(58) Field of Classification Search ................ 530/332, 530/300, 350, 324–330
See application file for complete search history.

(56) References Cited

U.S. PATENT DOCUMENTS 6,958,384 B2    10/2005    Gellman et al.

OTHER PUBLICATIONS

D.H. Appella, et al. Formation of short, stable helices in aqueous solution by β-amino acid hexamers. J. Am. Chem. Soc. (1999) 121, pp. 2309-2310.*
D.H. Appella, et al. J. Med. Chem. (1999) 121, pp. 2309-2310.*
D.H. Appella, et al. J. Am. Chem. Soc. (1999), 121, pp. 7574-7581.*
B.R. Huck, et al. Organic Letters (2000) 2(17), pp. 2607-2610.*
M.A. Schmitt, et al. J. Am. Chem. Soc. (2005) 127, pp. 13130-13131.*
A.V. Skamrov, et al. Molekuliarnaia Biologiia (1985) 1, pp. 177-195.*
J.Y. Kim et al. Bioorg. Med. Chem. Let. (2000) 10, pp. 2417-2419.*
Abele, Guichard, & Seebach (1998) "(S)-133-homolysine- and (S)-P3-homoserine-containing 13-peptides: CD spectra in aqueous solution," *Helv. Chim. Acta* 81:2141.
Appella, D. H.; Leplae, P. R.; Raguse, T. L.; Geliman, S. H. (2000) "(R,R,R)-2,5-Diaminocyclohexanecarboxylic Acid, a Building Block for Water-Soluble, Helix-Forming β-Peptides", *J. Org. Chem.* 65: 4766-4769.
Appella, Christianson, Karle, Powell, & Gellman (1996) "β-Peptide Foldamers: Robust Helix Formation in a New Family of β-Amino Acid Oligomers," *J. Am.Chem. Soc.* 118:13071.
Appella, Christianson, Klein, Powell, Huang, Barchi, & Gellman (1997) Residue-Based Control of Helix Shape in β-Peptide Oligomers *Nature* 387:381.

Appella, Christianson, Karle, Powell & Gellman (1999)[a] "Synthesis and Characterization of trans-2-Aminocyclohexanecarboxylic Acid Oligomers: An Unnatural Secondary Structure, and Implications for β-Peptide Tertiary Structure," *J. Am. Chem. Soc.* 121:6206.
Appella, Christianson, Klein, Richards, Powell, & Gellman (1999) "Synthesis and Characterization of Helix-Forming β-Peptides: trans-2-aminocyclopentanecarboxylic acid oligomers," *J. Am. Chem. Soc.* 121:7574.
Barchi, Huang, Appella, Christianson, Durell, & Gellman (2000) "Solution Conformations of Helxi-Forming n-Amino Acid Homooligomers," J. Am. Chem. Soc. 122:2711.
Blaskovich, Lin, Delarue, Sun, Park, Coppola, Hamilton, & Sebti (2000) "Design of GFB-111, a platelet-derived growth factor binding molecule with antiangiogenic and anticancer activity against human tumors in mice," *Nature Biotechnol.* 18:1065.
Bolm, Schiffers, Dinter, & Gerlach (2000) "Practical and highly enantioselective ring opening of cyclic *meso*-anhydrides mediated by cinchona alkaloids," *J. Org. Chem.* 65:6984.
Bothner-By, Stephens, Lee, Warren, & Jeanloz R. W. (1984) *J. Am. Chem. Soc.* (1984) 106:811.
Braunseliweiler & Ernst (1983) *J. Magn. Reson.* 53:521.
Cammers-Goodwin, Allen, Oslick, McClure, Lee & Kemp (1996) "Mechanism of stabilization of helical conformations of polypeptides by water containing trifluoroethanol,"*J. Am. Chem. Soc.* 118:3082.
Chin & Schepartz (2001) "Concerted evolution of structure and function in a miniature protein," *J. Am. Chem. Soc.* 123:2929.
Chung, Huck, Christianson, Stanger, Krauthauser, Powell & Gellman (2000) *J. Am. Chem. Soc.* 122:3995.
Cochran (2000) "Antagonists of protein-protein interactions," *Chem. Biol.* 7: R85.
Colucci, Tung, Petri & Rich (1990) *J. Org. Chem.* 55: 2895-2903.
Creighton, T. E. (1993) "Proteins: structures and molecular properties," 2nd Edition, p. 14.
Curran, Chandler, Kennedy, & Keaney (1996) N-α-Benzoyl-*cis*-4-amino-L-20 proLine: a γ-turnmimetic, *Tetrahedron Lett.* 37:1933.
Dado and Gellman (1994) *J. Am. Chem. Soc.* 116:1054-1062.
Fisk, Powell, & Gellman (2000) *J. Am. Chem. Soc.* 122:5443.
Degrado, Schneider, & Hamuro (1999) *Pept. Res.* 54:206.
Gellman (1998) *Acc. Chem. Res.* 31:173.

(Continued)

*Primary Examiner*—Andrew D Kosar
(74) *Attorney, Agent, or Firm*—Joseph T. Leone, Esq.; DeWitt Ross & Stevens S.C.

(57) ABSTRACT

Disclosed are isolated, unnatural polypeptides containing cyclically-constrained β-amino acid residues and cyclically-constrained γ-amino acid residues. The compounds are unnatural and because they contain rotationally constrained residues that are not amenable to enzymatic degradation, the compounds are useful to probe protein-protein and other large molecule interactions.

5 Claims, 5 Drawing Sheets

OTHER PUBLICATIONS

Gellman (1998)[b] "Minimal model systems for β-sheet secondary structure in proteins," *Curr. Opin. Chem. Biol.* 2:717.

Gomez-Vidal & Silverman (2001) "Short, highly efficient syntheses of protected 3-azido- and 4-azidoproline and their precursors," *Org. Lett.* 3:2481.

Goodman, Verdini, Toniolo, Phillips, & Bovey (1969) *Proc. Natl. Acad. Sci.* USA 64:444.

Gung, Zou, Stalcup, & Cottrell, (1999) "Characterization of a water-soluble, helical β-peptide," *J. Org. Chem.* 64:2176.

Hamuro et al. (1999) *J. Am. Chem. Soc.* 121:12200-12201.

Hanessian, Luo, Schaum, Michnick (1998) "Design of secondary structures in unnatural peptides: stable helical γ-tetra-, hexa-, and octapeptides and consequences of α-substitution," *J. Am. Chem. Soc.* 120:8569.

Hanessian, Luo, Schaum (1999) *Tetrahedron Lett.* 40:4925.

Herlt, Kibby, Rickards (1981) *Aust. J. Chem.* 34:1319-1324.

Hintermann, Gademann, Jaun, Seebach (1998) "γ-Peptides forming more stable 10 secondary structures than α-peptides: synthesis and helical NMR-solution structure of the γ-hexapeptide analog of H-(Val-Ala-Leu)$_2$-OH," *Helv. Chem. Acta* 81:983.

Kobayashi, Kamiyama, & Ohno (1990) "Chiral synthon obtained with pig-liver esterase—introduction of chiral centers into cyclohexene skeleton," *Chem. Pharm. Bull.* 38:350-354.

Kobayashi, Kamiyama, & Ohno (1990) "The first enantioselective synthesis of fortamine, the 1,4-diaminocyclitol moiety of fortimicin-A, by chemicoenzymatic approach," *J. Org. Chem.* 55:1169.

Lacroix, Kortemme, Lopez do la Paz, & Serrano (1999) *Curr. Opin. Struct. Biol.* 9:487.

Lee, Syud, Wang, Gellman (2001) "Diversity in Short β-Peptide 12-Helices: High Resolution Structural Analysis in Aqueous Solution of a Hexamer Containing Sulfonylated Pyrrolidine Residues," *J. Am. Chem. Soc.* 123:7721.

LePlae, Umezawa, Lee, Gellman (2001) *J. Org. Chem.* 66:5629-5632.

Luo & Baldwin (1997) "Mechanism of helix induction by trifluoroethanol: a framework for extrapolating the helix-forming properties of peptides from trifluoroethanol/water mixtures back to water," *Biochemistry* 36:8413.

Macura & Ernst (1980) *Mol. Phys.* 41:95.

Merrifield, R. B. (1963) "Solid Phase Peptide Synthesis. I. The Synthesis of a Tetrapeptide," *J. Am. Chem. Soc.* 85:2149-2154.

Ragothama, Awasthi, Balaram, (1998) "β-Hairpin nucleation by Pro-Glyβ-turns. Comparison of D-Pro-Gly and L-Pro-Gly sequences in an apolar octapeptide," *J. Chem. Soc., Perkin Trans.* 2:137.

Seebach et al. (1996) *Helv. Chem. Acta.* 79:913-941.

Seebach & Matthews (1997) *J. Chem. Soc.*, Chem. Commun. 2015-2022.

Seebach, Brenner, Rueping, Schweizer, Jaun (2001) "Preparation and determination of x-ray-crystal and NMR-solution structures of $\gamma^{234}$-peptides," *J. Chem. Soc., Chem. Commun.* 207.

Suhara et al. (1996) *Tetrahedron Lett.* 37(10):1575-1578.

Walgers, Lee, & Cammers-Goodwin, (1998) "An indirect chaotropic mechanism for the stabilization of helix conformation of peptides in aqueous trifluoroethanol and hexafluoro-2-propanol," *J. Am. Chem. Soc.* 120:5073.

Wang, Liu, Zhang, Shan, Han, Srinivasula, Croce, Alnemri, & Huang (2000) "Structure-based discovery of an organic compound that binds Bcl-2 protein and induces apoptosis of tumor cells," *Proc. Natl. Acad. Sci.* USA 97:7124.

Woll, Lai, Guzei, Taylor, Smith, Gellman, "Parallel Sheet Secondary Structur 20 in γ-Peptides," *J. Am. Chem. Soc.*, in press.

Zutshi, Brickner, & Chmielewski (1998) "Inhibiting the assembly of protein-protein interfaces," *Curr. Opin Chem. Biol.* 2:62.

Actimol, ActiMol Compounds and Compound Collection, http://www.actimol.com/.

Chembridge Corporation, http://chembridge.com.

Nanosyn, Chemistry on Demand, Accelerating Drug Discovery, http://www.nanosyn.com/.

Seebach et al (2003) Design and Synthesis of γ-Dipeptide Derivatives with Submicromolar Affinities for Human Somatostatin Receptors,: Angew. Chem. Int. Ed., 42(7):776-778.

* cited by examiner

HETEROGENEOUS FOLDAMERS CONTAINING α, β, AND/OR γ-AMINO ACIDS

CROSS-REFERENCE TO RELATED APPLICATIONS

Priority is hereby claimed to provisional application Ser. No. 60/406,006, filed Aug. 26, 2002, the entire contents of which is incorporated herein.

GOVERNMENT SUPPORT

This invention was made with United States government support awarded by the following agency: NSF 9820952. The United States has certain rights in this invention.

FIELD OF THE INVENTION

The invention is directed to polypeptides comprising α-amino acids and cyclically-constrained β and/or γ-amino acids. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution.

DESCRIPTION OF THE RELATED ART

Chemists have long sought to extrapolate the power of biological catalysis and recognition to synthetic systems. These efforts have focused largely on low-molecular weight catalysts and receptors. Most biological systems, however, rely almost exclusively on large polymers such as proteins and RNA to perform complex chemical functions. Predicting and modeling the solution-phase behavior of these large molecules has also been an on-going and sustained effort conducted by many groups.

Proteins and RNA are unique in their ability to adopt compact, well-ordered conformations. These two biopolymers are unique also because they can perform complex chemical operations (e.g., catalysis, highly selective recognition, etc.). Folding is linked to function in both proteins and RNA because the creation of an "lactive site" requires proper positioning of reactive groups. Consequently, there has been a long-felt need to identify synthetic polymer backbones which display discrete and predictable folding propensities (hereinafter referred to as "foldamers") to mimic natural biological systems. Such backbones will provide molecular "tools" to probe the functionality of large-molecule interactions (e.g. protein-protein and protein-RNA interactions). Insofar as these unnatural backbones are resistant to the action of proteases and peptidases, they are useful as probes having constrained conformational flexibility. Whereas a naturally occurring probe, comprised entirely of α-amino acid residues, will be readily degraded by any number of proteases and peptidases, foldamers comprising a mixture of α-, β-, and γ-amino acid residues are not.

Much work on homo-β-amino acids and peptides synthesized therefrom has been performed by a group led by Dieter Seebach in Zurich, Switzerland. See, for example, Seebach et al. (1996)[a] and Seebach et al. (1996)[b]. In the first of these two papers Seebach et al. describe the synthesis and characterization of a β-hexapeptide, namely (H-β-HVal-β-HAlβ-p-HLeu)$_2$-OH. Interestingly, this paper specifically notes that prior art reports on the structure of β-peptides have been contradictory and "partially controversial." In the second paper, Seebach et al. explore the secondary structure of the above-noted β-hexapeptide and the effects of residue variation on the secondary structure.

Dado and Gellman (1994) describe intramolecular hydrogen bonding in derivatives of β-alanine and γ-amino butyric acid. This paper postulates that β-peptides will fold in manners similar to α-amino acid polymers if intramolecular hydrogen bonding between nearest neighbor amide groups on the polymer backbone is not favored.

Suhara et al. (1996) report a polysaccharide analog of a β-peptide in which D-glycocylamine derivatives are linked to each other via a C-1 β-carboxylate and a C-2 α-amino group. This class of compounds has been given the trivial name "carbopeptoids."

Hamuro et al. (1999) describe antibacterial compositions containing β-peptides having a repeating 3-peptide residue motif. The compounds described are: Fmoc-(β$^3$-HVal-β$^3$-HLys-β$^3$-HLeu)$_n$-OH (n=2-4); H-(β$^3$-HVal-β$^3$-HLys-β$^3$-HLeu)$_n$-OH (n=2-4); and H-(β$^3$-HLeu-β$^3$-HLys-β$^3$-HLeu)$_n$-OH (n=2-6). While these β-peptides are described as being antibacterial, they are also hemolytic at concentrations near the effective antibacterial concentrations, thus limiting their utility as medicaments.

As noted above, the interest in foldamers stems in part from their resistance to enzymatic degradation. They are also interesting molecules because of their conformational behavior. The elucidation of foldamers having discrete conformational propensities akin to those of natural proteins has led to numerous recent explorations of peptides constructed from β-, γ-, or δ-amino acids. For recent reviews, see, for example, Seebach & Matthews (1997), Gellman (1998)[a] and Degrado et al. (1999). γ-Peptides containing residues bearing γ-substitution or α,γ-disubstitution or α,β,γ-trisubstitution have been shown to adopt a helical conformation defined by a 14-member turn that is stabilized by C=O(i)→NH(i+3) hydrogen bonds. See Hintermann et al. (1998) and Hanessian et al. (1998). Hanessian et al. (1999) have reported reverse turn formation by a γ-peptide built from α,γ-disubstituted residues having a stereochemistry that is different from that leading to helical folding.

In the hairpin loop architecture, found in natural proteins, two strands of the amino acid backbone of the molecule are connected by a short loop. The hairpin loop is essential for creating small increments of β-sheet secondary structure in conventional peptides. See Gellman (1998)[b] and Lacroix et al. (1999). Formation of β-sheet secondary structure requires non-covalent attraction between the strand segments, as well as an appropriate conformational propensity in the loop segment. Subtle variations in the covalent structure of the strand segments can prevent sheet formation. See, for example, Fisk, Powell, & Gellman (2000). The loop segment, however, need not be constructed from the same components as the strand segments. Several investigators have shown that non-peptide loops can allow anti-parallel β-sheet interactions between appended α-amino acid strands. Parallel β-sheet hairpins require a non-peptide loop because the strands must be linked C-terminus to C-terminus (or N-terminus to N-terminus). Anti-parallel sheet secondary structure has been documented in β-peptides containing both non-β-peptide and β-peptide linkers. See, for example, Chung et al. (2000).

BRIEF DESCRIPTION OF THE DRAWING FIGURES

FIG. 5 is a series of superimposed circular dichroism (CD) spectra of the γ-amino acid and homo-oligomers of

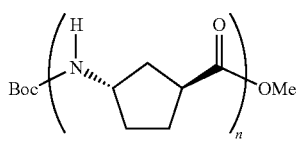

where n=1 to 6

Figure 6A:
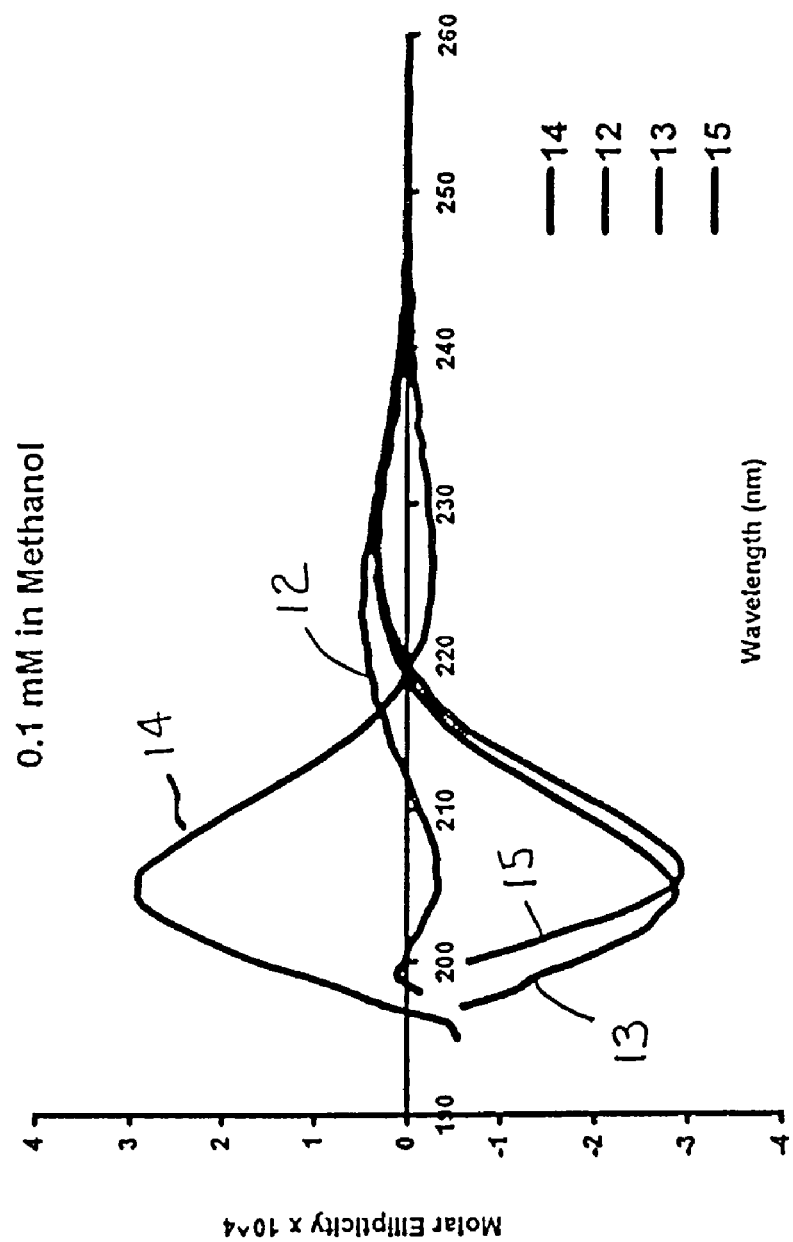
Figure 6B:
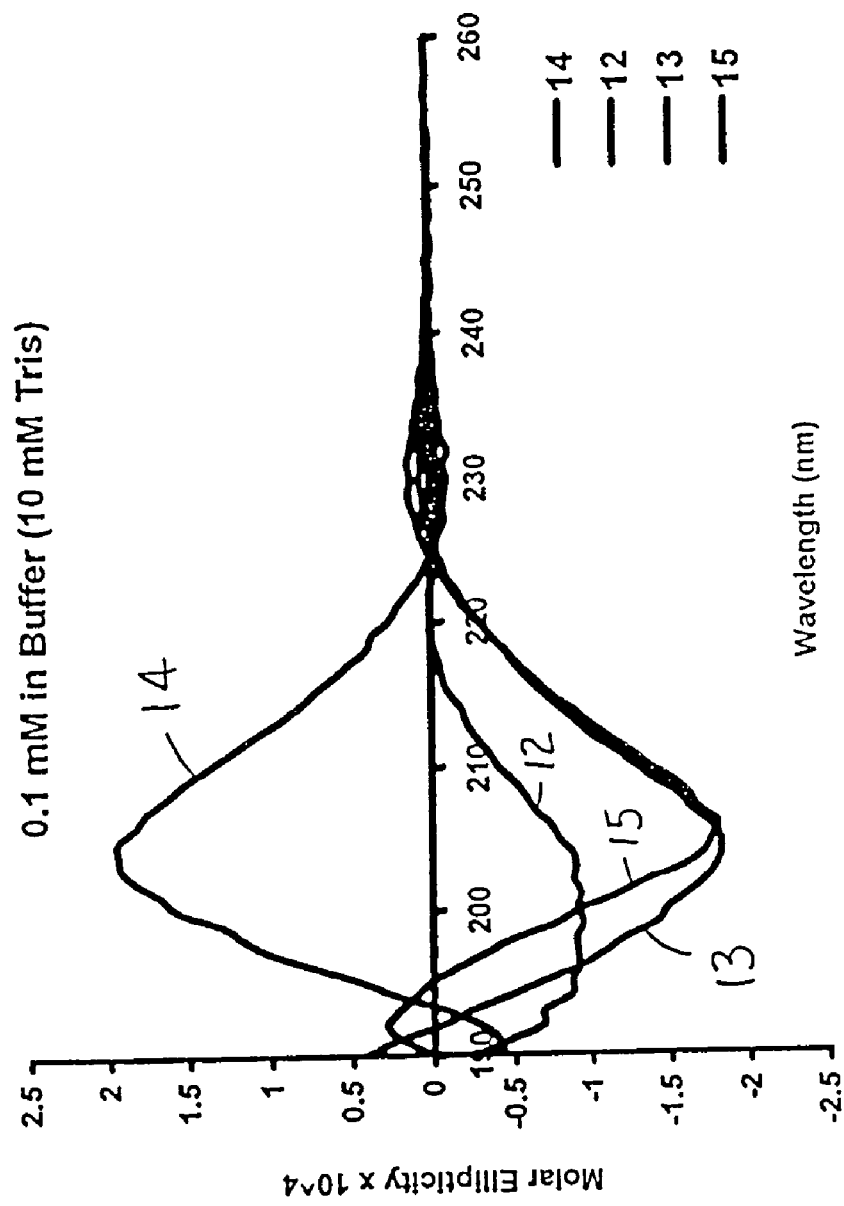

FIGS. 6A and 6B are CD spectra of compounds 12', 13', 14' and 15' (oligopeptides of alternating α-amino acid and β-amino acid residues). FIG. 6A depicts the CD spectra for each of compounds 12'-15' at a concentration of 1 mM in methanol. FIG. 6B depicts the CD spectra for each of compounds 12'-15' at a concentration of 1 mM in aqueous Tris buffer (10 mM).

DETAILED DESCRIPTION OF THE INVENTION

In a first embodiment, the invention is directed to an unnatural polypeptide compound containing at least one residue comprising a cyclically-constrained γ-amino acid residue. Here, the invention is directed to unnatural polypeptide compounds comprising four or more residues, wherein each residue is independently selected from the group consisting of α-amino acid residues, cyclically-constrained β-amino acid residues, and cyclically-constrained γ-amino acid residues, and further wherein at least two of the residues are cyclically-constrained β-amino acid residues or cyclically-constrained γ-amino acid residues, or one cyclically-constrained β-amino acid residue and one cyclically-constrained γ-amino acid residue.

A second embodiment of the invention is directed to related compounds wherein the residues are selected from α-amino acids or cyclically-constrained β-amino acids or cyclically-constrained γ-amino acids. In this embodiment, the invention is directed to an unnatural polypeptide comprising four or more residues, wherein each residue from among the minimum of four is independently selected from the group consisting of cyclically-constrained β-amino acid residues and cyclically-constrained γ-amino acid residues, and further wherein at least one of the minimum of four residues is a cyclically-constrained β-amino acid residue and at least one other of the four residues is a cyclically-constrained γ-amino acid residue.

A third embodiment of the invention is directed to an unnatural polypeptide compound selected from the group consisting of:

(i)

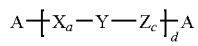

wherein:

each X and each Z is independently variable and is selected from the group consisting of α-amino acid residues, β-amino acid residues, and γ-amino acid residues, provided that at least one X or Z comprises an α-amino acid residue and another of X or Z comprises at least two cyclically-constrained γ-amino acid residues; and wherein each cyclically-constrained γ-amino acid residue is independently selected from the group consisting of:

(ii)

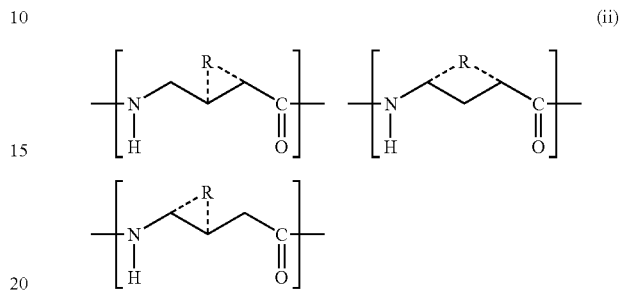

wherein R, together with the carbons to which it is attached, and further together with the β-position carbon in the γ-amino acid backbone where appropriate, independently defines a substituted or unsubstituted C$_4$ to C$_{10}$ cycloalkyl, cycloalkenyl, or heterocycle moiety, the heterocycle moiety having 1, 2, or 3 heteroatoms selected from the group consisting of N, S, and O; and each "Y" is independently variable and is a single bond or a reverse-turn moiety; and each "A" is independently selected from the group consisting of hydrogen, hydroxy, an amino-terminus protecting group, and a carboxy-terminus protecting group; and each "a," "c," and "d" is an independently variable positive integer, and wherein "a"+"c">3; and salts thereof.

When R in formula (ii) above, together with the carbons to which it is attached and the carbon at the position P to the carbonyl group, defines an unsubstituted cyclic moiety, it is preferred that the moiety be selected from the group consisting of:

(iv)

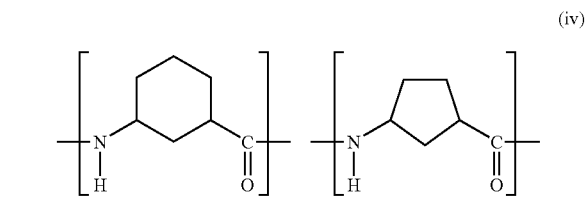

and (v)

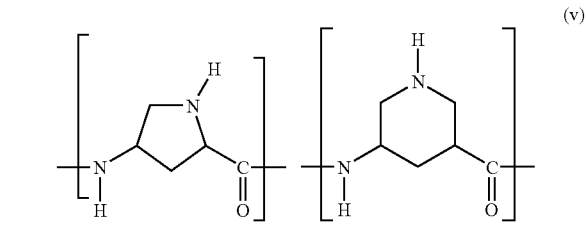

-continued

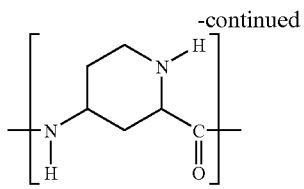

Specifically preferred compounds of the third embodiment are those wherein each R, together with the carbons to which it is attached and together with the β-position carbon in the γ-amino acid backbone where appropriate, independently defines a substituted $C_5$ to $C_6$ cycloalkyl, cycloalkenyl, or heterocycle moiety having a single nitrogen heteroatom; and substituents on the cycloalkyl, cycloalkenyl, or heterocycle moieties are independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{n+1}$—$OR^2$, —$(CH_2)_{n+1}$—$SR^2$, —$(CH_2)_{n+1}$—S(=O)—$CH_2$—$R^2$, —$(CH_2)_{n+1}$—S(=O)$_2$—$CH_2$—$R^2$, —$(CH_2)_{n+1}$—$NR^2R^2$, —$(CH_2)_{n+1}$—NHC(=O)$R^2$, —$(CH_2)_{n+1}$—NHS(=O)$_2$—$CH_2$—$R^2$, —$(CH_2)_{n+1}$—O—$(CH_2)_m$—$R^1$, —$(CH_2)_{n+1}$—S—$(CH_2)_m$—$R^1$, —$(CH_2)_{n+1}$—S(=O)—$(CH_2)_m$—$R^1$, —$(CH_2)_{n+1}$—S(=O)$_2$—$(CH_2)_m$—$R^1$, —$(CH_2)_{n+1}$—NH—$(CH_2)_m$—$R^1$, —$(CH_2)_{n+1}$—N{$(CH_2)_m$—$R^1$}$_2$, —$(CH_2)_{n+1}$—NHC(=O)—$(CH_2)_{n+1}$—$R^1$, —$(CH_2)_{n+1}$—NHS(=O)$_2$—$(CH_2)_m$—$R^1$; —$(CH_2)_n$—OR, —$(CH_2)_n$—$SR^2$, —$(CH_2)_n$—S(=O)—$CH_2$—$R^2$, —$(CH_2)_n$—S(=O)$_2$—$CH_2$—$R^2$, —$(CH_2)_n$—$NR^2R^2$, —$(CH_2)_n$—NHC(=O)$R^2$, —$(CH_2)_n$—NHS(=O)$_2$—$CH_2$—$R^2$, —$(CH_2)_n$—O—$(CH_2)_m$—$R^1$, —$(CH_2)_n$—S—$(CH_2)_m$—$R^1$, —$(CH_2)_n$—S(=O)—$(CH_2)_mR^1$, —$(CH_2)_n$—S(=O)$_2$—$(CH)_m$—$R^1$, —$(CH_2)_n$—NH—$(CH_2)_m$—$R^1$, —$(CH_2)_n$—{$(CH_2)_m$—$R^1$}$_2$—$(CH_2)_n$—NHC(=O)—$(CH_2)_m$—$R^1$, and —$(CH_2)_n$—NHS(=O)$_2$—$(CH_2)_m$—$R^1$; wherein m is an integer of from 2-6 and n is an integer of from 0-6; and wherein $R^2$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R^1$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane.

It is generally preferred that one of X or Z is a γ-amino acid residue wherein R in formula (iii), together with the carbons to which it is attached (and the carbon at the position β to the carbonyl group where appropriate), independently defines a substituted or unsubstituted cyclopentyl, substituted or unsubstituted cyclohexyl, unsubstituted or N-substituted piperidinyl, or unsubstituted or N-substituted pyrrolidinyl.

When Y is a reverse turn moiety, it is preferred that the reverse turn be independently selected from group consisting of a prolyl-glycolic acid residue, a di-nipecotic acid residue, or a compound of the following formula:

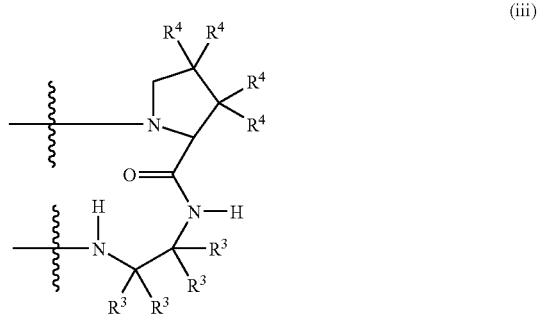

(iii)

where each $R^3$ is independently variable and is selected from the group consisting of hydrogen, linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, and mono- or bicyclic heteroaryl-$C_1$-$C_6$-alkyl; and where each $R^4$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane.

A fourth embodiment of the invention is directed to an unnatural polypeptide compound selected from the group consisting of:

(i)

wherein:

each X and each Z is independently variable and is selected from the group consisting of (α-amino acid residues, β-amino acid residues, and γ-amino acid residues, provided that at least one X or Z comprises an α-amino acid residue and another of X or Z comprises at least two cyclically-constrained β-amino acid residues; and wherein each cyclically-constrained β-amino acid residue is independently selected from the group consisting of:

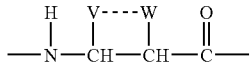
(vi)

wherein V and W are combined, together with the carbon atoms to which they are bonded, and independently define a substituted or unsubstituted $C_3$-$C_8$ cycloalkyl, cycloalkenyl or heterocyclic ring having one or more N, O or S atom(s) as the heteroatom(s);

the substituents on carbon atoms of the rings being independently selected from the group consisting of linear or branched $C_1$-$C_6$-alkyl, alkenyl, alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, and the substituents listed above for X and Y when X and Y are not combined;

the substituents on nitrogen heteroatoms of the rings being independently selected from the group consisting of —S(=O)$_2$—CH$_2$—R$^{17}$, —C(=O)—R$^{17}$, —S(=O)$_2$—(CH$_2$)$_m$—R$^{18}$, and —C(=O)—(CH$_2$)$_{n+1}$—R$^{18}$;

wherein R$^{17}$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein R$^1$ is independently selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and wherein each cyclically-constrained β-amino acid residue is further selected from the group consisting of:

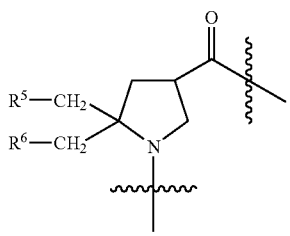
(vii)

and

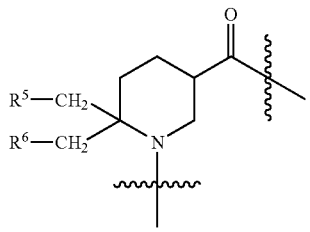

wherein R$^5$ and R$^6$ are independently selected from the group consisting of hydrogen, hydroxy, linear or branched $C_1$-$C_{16}$-alkyl, alkenyl, or alkynyl; mono- or di-$C_1$-C16 alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{0-6}$—NHC(=O)R$^7$, —(CH$_2$)$_{0-6}$—NHS(=O)$_2$—CH$_2$—R$^7$, —(CH$_2$)$_{0-6}$—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein R$^7$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and R$^8$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfonyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and wherein each cyclically-constrained β-amino acid residues is further selected from the group consisting of:

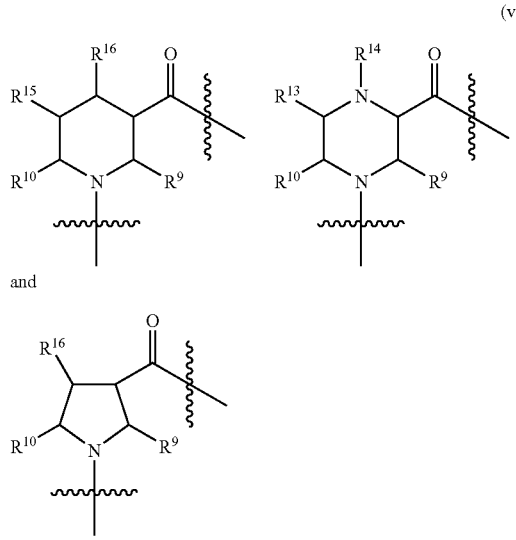

and wherein $R^9$, $R^{10}$, and $R^{13}$ are independently selected from the group consisting of hydrogen, linear or branched $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{1-6}$—$OR^{11}$, —$(CH_2)_{1-6}$—$SR^{11}$, —$(CH_2)$—$S(=O)$—$CH_2$—$R^{11}$, —$(CH_2)_{1-6}$—$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{1-6}$—O—$(CH_2)_{2-6}$—$R^{12}$, —$(CH_2)_{1-6}$—S—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$(CH_2)_{1-6}$—NH—$(CH_2)_{2-6}$—$R^{12}$, —$(CH_2)_{1-6}$—N-$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_2$—$R^{12}$; wherein $R^{11}$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and $R^{12}$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane;

$R^{14}$ is selected from the group consisting of hydrogen, linear or branched $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{1-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and each "Y" is independently variable and is a single bond or a reverse-turn moiety; and each "A" is independently selected from the group consisting of hydrogen, hydroxy, an amino-terminus protecting group, and a carboxy-terminus protecting group; and each "a," "c," and "d" is an independently variable positive integer, and wherein "a"+"c">3; and salts thereof.

A fifth embodiment of the invention is directed to a method of probing, disrupting, or mimicking binding interactions between two protein molecules or fragments thereof, the method comprising: in an in vivo, in vitro, or ex vivo reaction between the two proteins, introducing to the reaction an unnatural polypeptide compound as described hereinabove. Then, quantifying any effect of the added compound on the thermodynamic or kinetic parameters of the binding interaction between the two protein molecules or fragments thereof.

As used in the specification and the claims, the word "independently," when referring to the nature of a variable substituent, explicitly means that each appearance of the defined substituent within a molecule can be different. Thus, for example, in a molecule according to the present invention such as A-$X_3$—$Z_3$—B (where Y is a single bond, A is hydrogen, and B is hydroxy), each appearance of X and each appearance of Z can vary independently within the molecule. Thus, according to this explicit definition, the molecule A-$X_3$—$Z_3$—B explicitly encompasses the molecule A—X'—X"—X'"—Z'—Z"—Z'"—B, where X' may the same as or different from X", and X" may be the same as or different from X'". Likewise, Z' may the same as or different from Z", and Z" may be the same as or different from Z'".

As used herein, the terms "α-amino acid" and "α-amino acid residue" designate any and all natural and unnatural α-amino acids and their respective residues (i.e., the form of the amino acid when incorporated into a polypeptide molecule), without limitation. Thus, "α-amino acid" explicitly encompasses the conventional and well-known naturally occurring amino acids. The term "α-amino acid" thus encompasses, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Illustrative α-amino acids also include analogs such as N-methylated α-amino acids, hydroxylated α-amino acids, and the like. An exemplary list of modified or unusual a-amino acids that can be used in the present invention include (without limitation): N-alkyl α-amino acids (such as N-methyl glycine), hydroxylysine, 3-hydroxyproline, 4-hydroxyproline, nor-valine, nor-leucine, ornithine, and the like.

As used herein, the terms "β-amino acid" and "β-amino acid residue" refer to any and all natural and unnatural β-amino acids and their respective residues (i.e., the form of the amino acid when incorporated into a polypeptide molecule), without limitation. Specifically included are those β-amino acids described in U.S. Pat. No. 6,060,585, issued May 9, 2000, incorporated herein by reference, and those described in U.S. Pat. No. 6,683,154, issued Jan. 27, 2004; U.S. Pat. No. 6,710,186, issued Mar. 23, 2004; and U.S. Pat. No. 6,727,368, issued Apr. 27, 2004, all of which are incorporated herein.

As used herein, the terms "γ-amino acid" and "γ-amino acid residue" refer to any and all natural and unnatural γ-amino acids and their respective residues (i.e., the form of the amino acid when incorporated into a polypeptide molecule), without limitation.

The term "cyclically-constrained," when applied to β-amino acids and residues, designates that the α and β backbone carbon atoms of each β-amino acid or residue are incorporated into a $C_3$-$C_{10}$ cycloalkyl, cycloalkenyl, aryl, or hetercyclic ring. In the case of γ-amino acids and residues, the term "cyclically-constrained" designates that the α and β backbone carbon atoms, the α and γ backbone carbon atoms, or all three of the α, β, and γ backbone carbon atoms of each γ-amino acid or residue are incorporated into a $C_3$-$C_{10}$ cycloalkyl, cycloalkenyl, aryl, or hetercyclic ring.

As used herein, the term "reverse turn moiety," refers to any bifunctional linking moiety that serves to bring the X and Z moieties into alignment so as to have the potential to form sheet structures. Explicitly included within the definition of "reverse turn moiety" are the prolyl-glycolic acid linkage and the di-nipecotic acid linkage described in U.S. Pat. No. 6,683, 154, issued Jan. 27, 2004. See also U.S. Pat. No. 6,060,585. Also explicitly included within the definition of "reverse turn moiety" is the following linkage, where the R3 and R4 groups are as defined hereinabove.

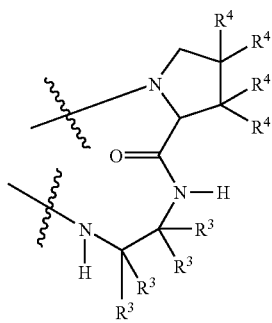

As used herein, the terms "amino-terminus protecting group" and "carboxy-terminus protecting group" refer to any chemical moiety capable of addition to and (optionally) removal from a reactive site (an amino group and a carboxy group, respectively, in this instance) to allow manipulation of a chemical entity at sites other than the reactive site. Protecting groups, and the manner in which they are introduced and removed are described, for example, in "Protective Groups in Organic Chemistry," Plenum Press, London, N.Y. 1973; and in "Methoden der organischen Chemie," Houben-Weyl, 4th edition, Vol. 15/1, Georg-Thieme-Verlag, Stuttgart 1974; and in Theodora W. Greene, "Protective Groups in Organic Synthesis," John Wiley & Sons, New York 1981. A characteristic of many protecting groups is that they can be removed readily, i.e., without the occurrence of undesired secondary reactions, for example by solvolysis, reduction, photolysis or alternatively under physiological conditions.

A host of protecting groups are known in the art. An illustrative, non-limiting list of protecting groups includes methyl, formyl, ethyl, acetyl, t-butyl, benzyl, trifluoroacetyl, t-butoxycarbonyl, benzoyl, 4-methylbenzyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethylchroman-6-sulphonyl. The terms "amino-terminus protecting group" and "carboxy-terminus protecting group" as used herein are explicitly synonymous with such terms as "N-terminal capping group" and "C-terminal capping group," respectively. A host of suitable protecting and capping groups, in addition to those described above, are known in the art. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521,184 (issued May 28, 1996).

Regarding salts of the subject compounds, compounds having at least one basic group or at least one basic radical, for example a free amino group, a pyrazinyl radical, or a pyridyl radical, may form acid addition salts. Thus, the invention encompasses acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or polyacid addition salts may be formed.

As used herein, the terms alkyl, alkenyl, and alkynyl explicitly encompass linear, branched and/or cyclic moieties, including mono- and bicyclic moieties. In the case of disubstituted amine, amide and carboxamide moieties (e.g., a di-$C_1$-$C_6$-alkyl-substituted amine), the disubstitution explicitly encompasses substitution patterns wherein the nitrogen atom defines part of a heterocyclic ring.

When the subject compounds have acidic groups, for example a free carboxy group, the invention encompasses metal and ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethylpiperidine or N,N'-dimethyl-piperazine.

Compounds of formula (i) having both acidic and basic groups can form internal salts. The salts may be pharmaceutically-acceptable salts or pharmaceutically-unacceptable salts.

The subject compounds find use as peptide mimetics that are not easily degraded by the action of proteolytic enzymes. Thus, the cyclically-constrained peptides of the present invention can be used as probes to explore protein-protein interactions. Because the compounds of the present invention are cyclically-constrained, they are more restricted conformationally than their strictly α-polypeptide counterparts. The compounds can be labeled and tracked throughout any given reaction. The effect the compound has on any given reaction provides valuable information on either or both of the kinetics and/or thermodynamics of the reaction being studied. Such reactions can be performed in vitro, in vivo, and ex vivo.

Libraries of the subject compounds can also be prepared by automated means, thus providing access to a huge database which can be used as a tool to test, for example, potentially biologically-active agents.

One highly useful aspect of the invention is that because the backbone is heterogenous, a portion of the residues, such as the α-amino acids, provide functional diversity (thus allowing many different types of reactions in many different types of environments to be explored), while the cyclically-constrained residues provide conformational specificity and stability. For example, massive diversity can be obtained using commercially-available α-amino acids as building blocks, while structural rigidity is conferred by using only a single type of rigidified (i.e., cyclically-constrained) β- or γ-amino acid.

With particular focus on protein-protein interactions, it has long been a goal of biological scientists to disrupt specific protein-protein interactions as a means to explore the nature of the interaction. This goal has proven difficult to achieve using traditional small molecules. Binding size is likely part of the problem. Protein-protein complexes generally involve relatively large molecular surfaces. This makes it difficult for a small molecule to bind competitively at such a site. The present compounds, however, are polyamides and can be quite large. Thus, as a class, these compounds, individually and in the form of large libraries of compounds, are much better suited for probing protein-protein interactions than are small molecules. Additionally, the conformations of the subject compounds are periodic; the conformations can be extended simply by adding additional monomers to the polypeptide. Thus, the present compounds can be fabricated as relatively small skeletons or as very large skeletons, the size being dictated, at least in part, by the size of the binding site to be studied.

I. Alpha Amino Acids and Polypeptides Formed Therefrom

As noted above, the α-amino acids and α-polypeptides that can be utilized in the present invention can be any α-amino acid, natural or unnatural, without limitation. Thus, as used herein, "α-amino acid" explicitly encompasses the conventional and well-known naturally occurring amino acids, their unnatural enantiomers, as well as all synthetic variations, derivatives, and analogs thereof. Preferred are the naturally occurring α-amino acids, and their unnatural enantiomers.

II. Cyclically-Constrainted Beta Amino Acids and Polypeptides Formed Therefrom

The cyclically-constrained β-amino acid polypeptides and monomers that can be utilized in the present invention are those disclosed and claimed in U.S. Pat. No. 6,060,585, issued May 9, 2000, to Gellman et al., and incorporated herein by reference. Additionally, β-amino acid polypeptides and monomers such as those disclosed U.S. Pat. No. 6,683,154, issued Jan. 27, 2004, to Gellman et al, may also be used in the present invention.

Further still, cyclic imino carboxylic acids and gem-di-substituted cyclic imino carboxylic acids (both of which are a type of cyclically-constrained β-amino acid) can also be used in the invention. Preferably, these residues take the form of the compounds (individual residues and polypeptides) disclosed in U.S. Pat. No. 6,727,368, issued Apr. 27, 2004, to Gellman et al.

Further still, these β-residues may also take the form of the gem-di-substituted cyclic imino acids disclosed in U.S. Pat. No. 6,710,186, issued Mar. 25, 2004.

III. Gamma Amino Acids and Polypeptides Formed Therefrom

Molecular modeling studies performed by the inventors suggested that polypeptides containing γ-amino acid residues similar to trans-3-aminocyclopentanecarboxylic acid (trans-3-ACPC) residues would have a high propensity for γ-peptide parallel sheet secondary structure. Molecules exhibiting this type of secondary structure would be in stark contrast to the helical propensity previously documented for acyclic γ-amino acid residues.

Thus, molecules 1 and 2 were prepared. In each of these compounds, two (1S, 3S)-trans-3-ACPC residues are linked via a D-prolyl-(1,1-dimethyl)-1,2-diaminoethyl unit:

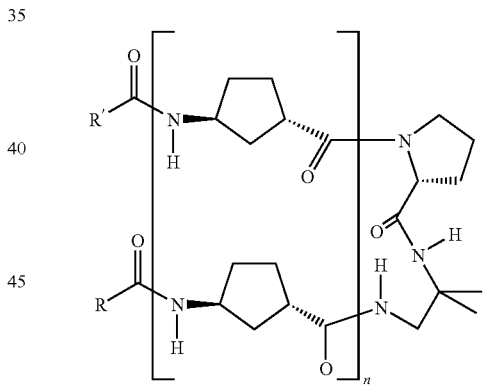

1: n=1, R=R'=OC(CH$_3$)$_3$
2: n=1, R=R'=CH$_2$Ph
3: n=3, R=CH$_2$Ph, R'=C(CH$_3$)$_3$

The diamine linker portion of compounds 1, 2, and 3 has previously been shown to allow parallel β-sheet formation between attached α-amino acid residue strand segments. See Fisk, Powell, & Gellman (2000).

Figure 1:
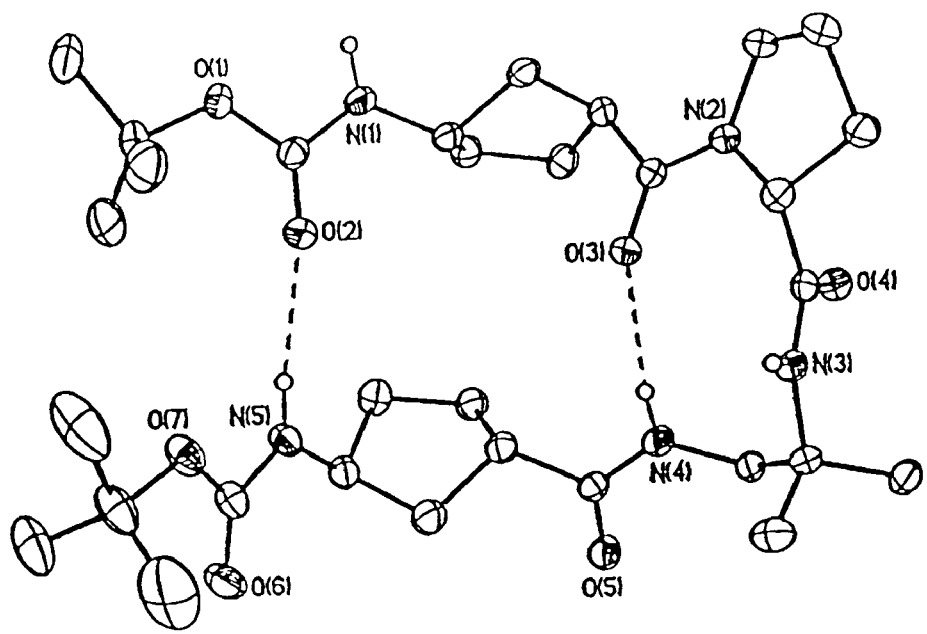
FIG. 1 is a model depicting the solid state crystal structure of compound 1. All hydrogen atoms, except those attached to nitrogen, have been omitted for clarity.

Crystal structures of 1 and 2 show that both molecules adopt the desired hairpin conformation in the solid state. See FIGS. 1 and 2, which are solid-state crystal structures of compounds 1 and 2, respectively. These results, particularly the similarity between two independent structures, show that the non-γ-peptide linker allows a parallel sheet hydrogen bonding pattern between attached γ-peptide strands.

Molecule 2 was examined by two-dimensional NMR methods in CD$_2$Cl$_2$ (3.6 and 5.7 mM, 25° C.) to evaluate the propensity for parallel γ-peptide sheet formation under dynamic conditions. Under these conditions, molecule 2 exhibits little or no aggregation in solution. (The amide proton shifts of 2 displayed minimal variation over the concentration range of from about 0.3 mM to about 10 mM in $CD_2Cl_2$, indicating that there is little or no self-association of 2 under these conditions.) Previous work with small oligoamides, including hairpin molecules that contain α- and/or β-amino acid residues has shown that intramolecular hydrogen bonding provides a modest drive for folding in nonpolar solvents, but that sheet-type hydrogen bonding will not occur unless both the strand and the turn segments have suitable conformational propensities.

Figure 2:
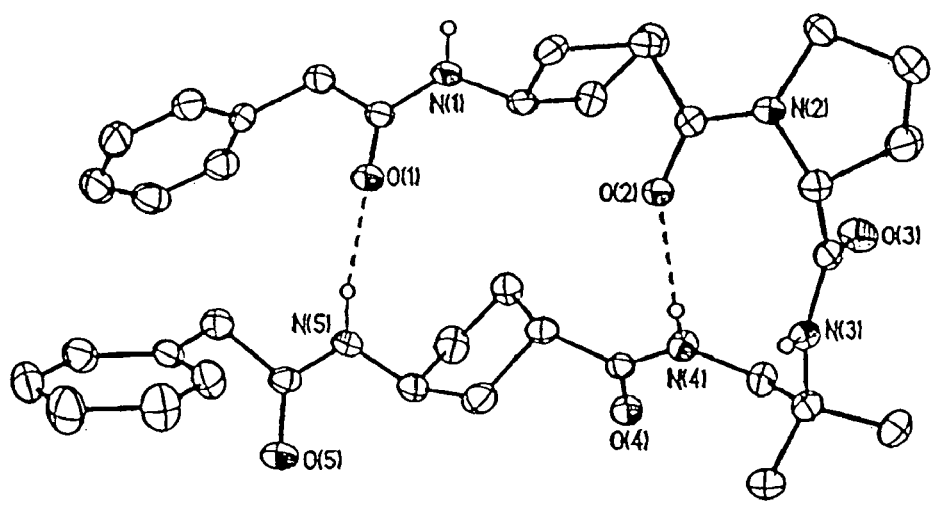
FIG. 2 is a model depicting the solid state crystal structure of compound 2. All hydrogen atoms, except those attached to nitrogen, have been omitted for clarity.

A combination of COSY (correlated spectroscopy), TOCSY (total correlation spectroscopy), and ROESY (rotational nuclear Overhauser effect spectroscopy) spectra provided sufficient data to allow nearly all of the proton resonances from 2 to be unambiguously assigned. This, in turn, enabled the use of the amide proton chemical shift data to gain preliminary insight on folding. In nonpolar solvents C=O to H—N hydrogen bond formation causes an increase (up to 2-3 ppm) in the chemical shift of an amide proton ($\delta$NH). Equilibria between hydrogen bonded and non-hydrogen bonded states are usually rapid on the NMR time scale, and observed $\delta$NH values are therefore weighted averages of the contributing hydrogen bonded and non-hydrogen bonded states. For compound 2 in $CD_2Cl_2$, the pattern of $\delta$NH values observed indicates that a significant population of the molecules adopt the conformation shown in FIG. 2; i.e., in solution, a significant proportion of compound 2 molecules adopt the same conformation as observed in the solid state. $\delta$NH-1 (5.52 ppm) and $\delta$NH (5.63 ppm) are consistent with little or no hydrogen bonding at these amide protons, while $\delta$NH-4 (7.04 ppm) and $\delta$NH-5 (7.24 ppm) indicate substantial hydrogen bond donation by these groups (using atom numbering as shown in FIG. 2).

More detailed structural insight was obtained from ROESY data for 2. Most informative among the short-range NOEs was one between the $C_\delta H$ of proline and the $C_\alpha H$ of the trans-3-ACPC residue attached to proline. This NOE showed that the tertiary amide linkage has the Z configuration in solution, as observed in both crystal structures shown in FIGS. 1 and 2. In addition, six NOEs between the two γ-amino acid residues (or immediately adjacent atoms) could be assigned unambiguously. See FIG. 3 for a graphic representation of these NOEs in compound 2. Five of these NOEs are consistent with the conformation observed for 2 in the solid state or modest distortions from this conformation: $C_\gamma H \rightarrow C_\alpha H$ (strong; 2.29 Å), $C_\gamma H \rightarrow$ linker NH (weak; 3.64 Å), $C_\gamma H \rightarrow C_\in H$ (medium; 2.41 Å), $C_\gamma H \rightarrow$ NH (weak; 3.72 Å), and phenacyl $CH_2 \rightarrow$ NH (weak; 3.95 Å). (The distances given after NOE intensities were measured in the crystal structure of compound 2.)

Figure 3:
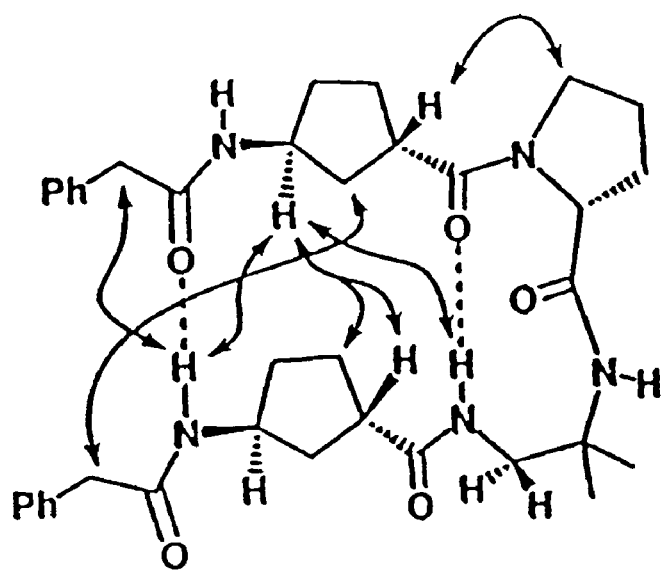
FIG. 3 is a graphic summary of selected NOEs for compound 2 (3.6 mM in CD$_2$Cl$_2$, 25° C.).

The sixth nonadjacent NOE shown in FIG. 3, $C_\beta H \rightarrow$ phenacyl $CH_2$ (weak), suggests that an alternative mode of interstrand interaction occurs to at least a small extent for 2 in $CD_2Cl_2$. This is because the shortest distance between protons on these two methylene groups is 5.91 Å in the crystal structure of 2.

Figure 4:
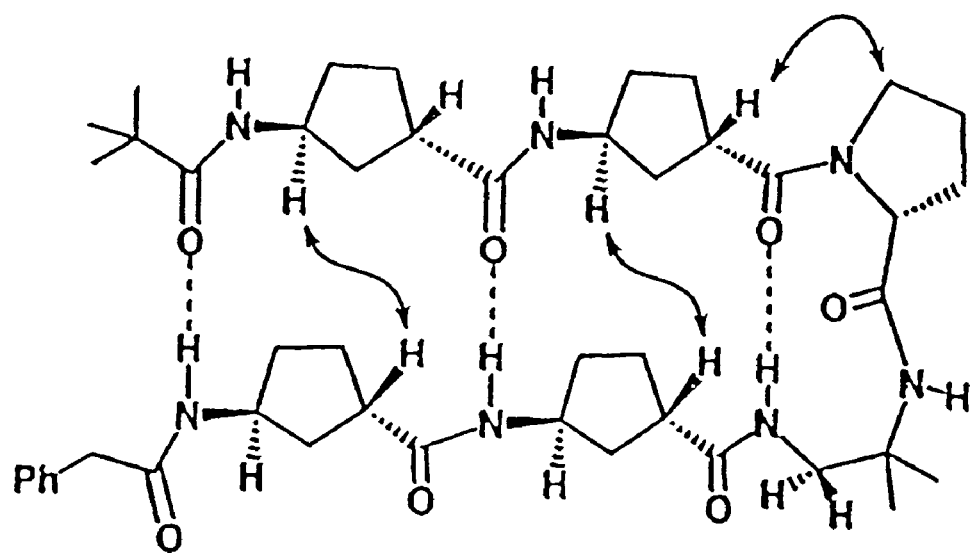
FIG. 4 is a graphic summary of selected NOEs for compound 3 (2 mM in pyridine-d5, 25° C.).

Molecule 3, which has two-residue γ-peptide strands on either side of the loop, was then synthesized and examined to determine whether parallel sheet secondary structure could propagate outward from the loop structure. Two-dimensional NMR analysis was carried out in pyridine-$d_5$ (2 mM, 25° C.) because compound 3 is nearly insoluble in $CD_2Cl_2$. Several key NOEs were unambiguously identified. See FIG. 4. The tertiary amide involving the proline nitrogen was shown to have the Z configuration by observation of a strong NOE between proline $C_\delta H$ and $C_\alpha H$ of the adjacent trans-3-ACPC residue. Strong $C_\gamma H \rightarrow C_\alpha H$ NOEs were observed between the inner pair of trans-3-ACPC residues and between the outer pair of trans-3-ACPC residues. These two NOEs indicate that in solutions of compound 3 there is a significant population of a hairpin conformation in which the parallel γ-peptide sheet involves all four trans-3-ACPC residues.

Thus, the present inventors have shown that the γ-peptides 1, 2, and 3 adopt sheet secondary structure in solution.

The utility of these compounds for probing protein interactions is great because, as noted above, the γ-peptides adopt structures analogous to those seen in natural proteins and peptides. Thus, the subject compounds mimic natural protein conformations in solution, but are resistant or immune to proteolytic degradation by proteases and peptidases. The cyclically-constrained γ-amino acid residues incorporated into homogeneous γ-peptide backbones are useful probes in the study of chemical and enzymatic interactions involving natural proteins. Also, the compounds disclosed herein add greatly to the γ-peptide field, in terms of both the number of alternative secondary structures that can be accessed and the intrinsic stability of those secondary structures. The subject compounds are useful probes because the cyclically-constrained residues create secondary structures with high conformational stability at short oligomer lengths that are also resistant to enzymatic degradation. The invention thus enhances the control over γ-peptide folding preferences, thereby providing a larger "toolbox" of probes to be used in investigating the function of naturally-occurring proteins.

Compound 24a, an analog of 3, as well as higher analogs 24b and 24c are also easily prepared using the methods described herein. NMR analysis of these molecules in methanol, and other organic solvents, will show that the trans-4-aminopyrrolidinyl (trans-4-AP) residue supports γ-peptide hairpin formation in the same fashion as in compounds 1-3.

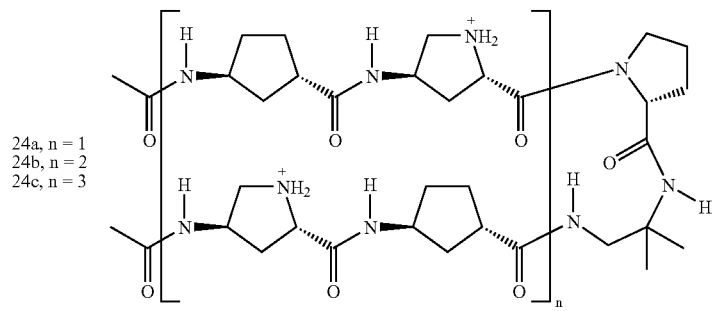

24a, n = 1
24b, n = 2
24c, n = 3

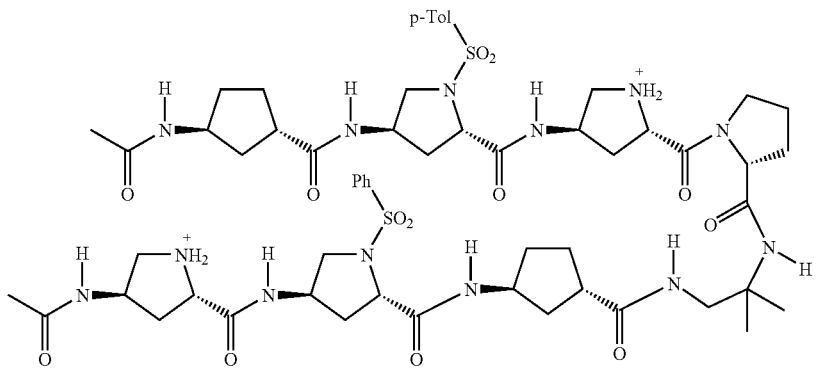

25

Because oligomers containing trans-4-AP will display parallel sheet secondary structure in aqueous solution, diverse side-chains can be introduced into the rigidifying ring via sulfonylation of ring nitrogen atoms (e.g., as shown in compound 25). It has recently been shown that the ring nitrogen sulfonylation of pyrrolidine-based residues allows side-chain introduction in the β-peptide 12-helix, and this approach should function with equal success in the subject γ-peptides. See Lee et al. (2001). The design of 25 places hydrophobic side-chains across from one another, at the second residue of each strand. The crystallographic data for compounds 1 and 2 suggest that the parallel sheet conformation will be stabilized in water by clustering of the hydrophobic sulfonyl substituents.

Antiparallel γ-peptide secondary structure can be created by changing the linker used to connect strand segments. Initial studies will involve minimal hairpin molecules 26a-b, which have trans-3-ACHC residues in the strands.

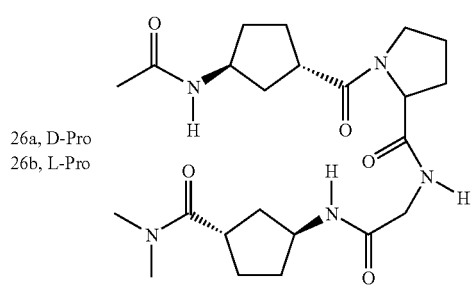

26a, D-Pro
26b, L-Pro

The prolyl-glycyl linker promotes strand interactions between α-amino acid residues. Gellman (1998)[b] and Ragothama et al. (1998). Molecular modeling indicates that this linker is suitable for γ-residues as well.

Molecular modeling also indicates that a heterochiral dimer of cis-3-ACPC will form the γ-peptide analog of the familiar β-turn seen in α-peptides. This hypothesis can be tested by examining tetra-γ-peptides like compound 27.

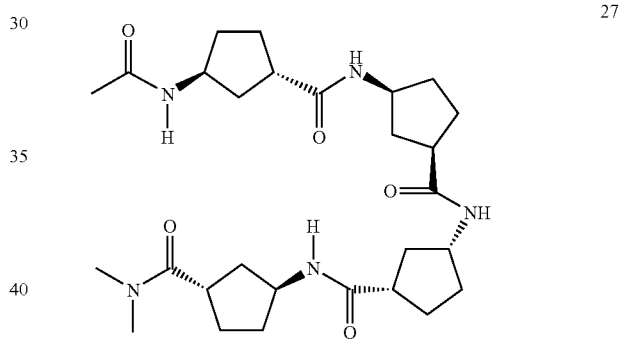

27

Functionally diverse antiparallel γ-peptide sheets that fold in water can thus be created by preparing analogs that contain amino-proline residues.

The only known γ-peptide helix generated to date was made exclusively with acyclic γ-amino acid residues; see Hintermann, Gademann, Jaun, Seebach (1998). Molecular modeling, however, indicates that two different cyclohexyl-rigidified residues, 28 and 29, should stabilize the γ-peptide 14-helix.

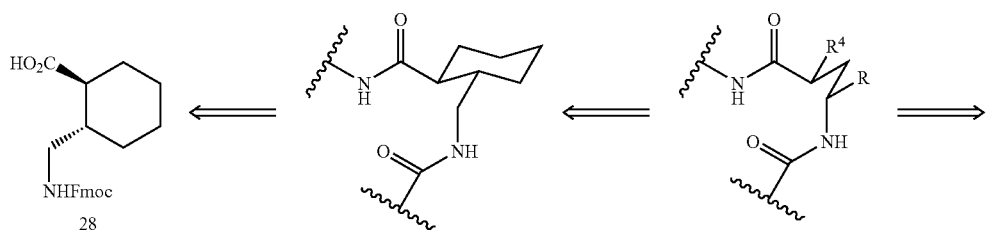

28

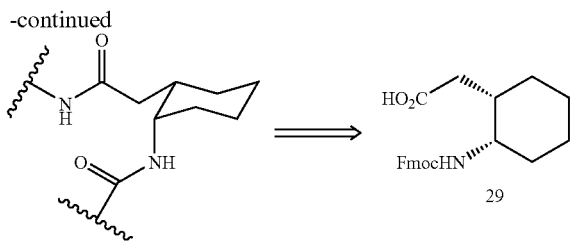

Both of these residues are available in enantiomerically pure form via straightforward extensions from or variations upon the synthetic routes currently in use, see Appella et al. (1999) [a], to provide the β-amino acid trans-2-aminocyclohexanecarboxylic acid (trans-2-ACHC). For example, an N-protected form of cis-2-ACHC subjected to an Arndt-Eisterdt homologation reaction, Goodman et al. (1969), would then provide the N-protected version of 29. Preparation of the Boc-protected analog of 28 would start with the reported enzymatic desymmetrization of cis-4,5-cyclohexenedicarboxylic acid dimethyl ester. See Scheme 2 and Kobayashi, Kamiyama, & Ohno (1990)[a] and (1990)[b].

NMR analysis of these homooligomers, and co-oligomers of 28 and 29, in organic solvents, should reveal their conformational stability. Proton resonance overlap may be too great to allow complete high-resolution structural analysis. If NMR analysis of these γ-peptides is fruitless, preparing γ-peptides containing a few scattered acyclic residues (e.g., hexamer 31) should enhance proton resonance dispersion.

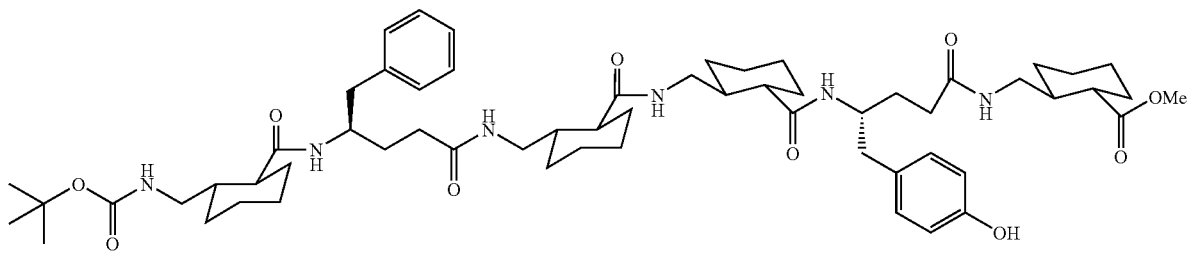

31

SCHEME 2

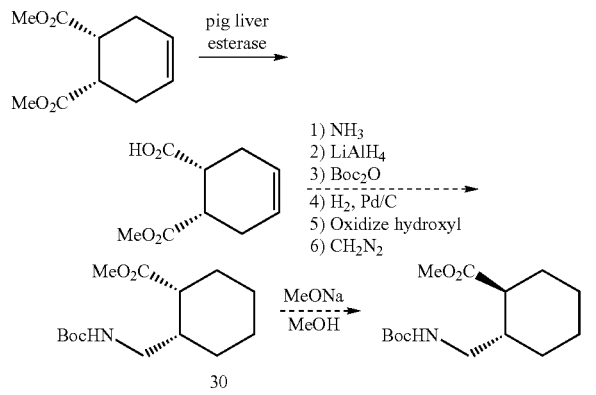

The half ester can be converted to either monoamide, and straightforward reactions will generate the protected cis-γ-amino acid 30. Kobayashi, Kamiyama, & Ohno (1990)[a] and (1990)[b] suggest that base-catalyzed epimerization will lead efficiently to the desired trans isomer, a protected form of 28.

Homo-oligomers of 28 and of 29, up to octamer length, are easily prepared using the linking chemistry described below.

The strategy of mixing cyclic and acyclic residues should also allow the fabrication of water-soluble γ-peptides that benefit from residue pre-organization. Various synthetic routes can then be used to make analogs that bear attachment sites for side-chains. For example, the route to trans-2-ACHC described in the Examples below is also applicable to the commercially-available piperidine β-keto ester 32, which provides cis-amino ester 33 and that should lead ultimately to protected γ-amino acid 34, an analog of 29, via Scheme 3):

SCHEME 3

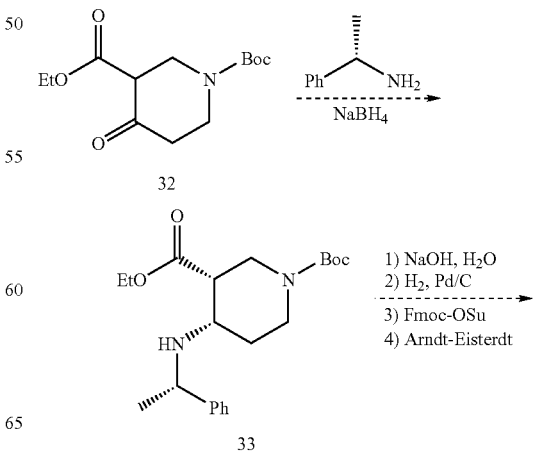

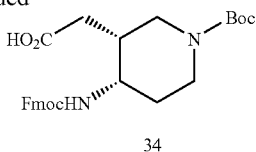

34

Equally useful for purposes of the present invention are cyclic γ-amino acids that are not expected to promote 14-helix formation based on the conformational analysis above, e.g., γ-amino acids 35-40:

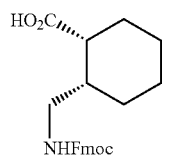

35

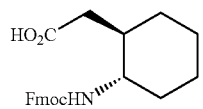

36

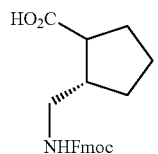

37

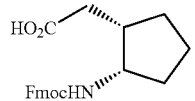

38

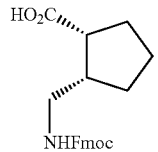

39

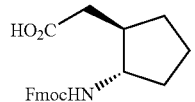

40

These studies should provide unprecedented γ-peptide secondary structures (presumably helical). γ-Amino acids 35 and 36 are diastereomers of 28 and 29 that will disfavor the $g^+,g^+$ torsion sequence along the (O═)CC$_\alpha$-C$_\beta$C$_{65}$ and C$_\alpha$C$_\beta$-C$_\gamma$N backbone bonds, while γ-amino acids 35-40 contain cyclopentane rings. The switch from trans-cyclohexyl to trans-cyclopentyl constraint among β-amino acids causes a profound change in β-peptide secondary structure preference (14- to 12-helix), presumably because the cyclopentyl constraint does not promote 60° angles about the backbone C$_\alpha$-C$_\beta$ bond. See Appella et al. (1996), (1997), (1999)[a & b], and Barchi et al. (2000). By extrapolation, residues derived from 37-40 are expected to disfavor the γ-peptide 14-helix. There is, however, a strong likelihood that these residues will give rise to other discrete secondary structure preference(s) because of the very limited residue conformational freedom.

Synthesis of the necessary γ-peptide building blocks should is straightforward. For example, 30 in Scheme 2 is a precursor to 35. Asymmetric opening of the anhydride of cis-1,2-cyclopentanedicarboxylic acid, Bolm, Schiffers, Dinter, & Gerlach (2000), will lead to 38 and 39. Arndt-Eisterdt homologation of Fmoc-protected trans-2-ACPC will generate Fmoc-protected 40. Pyrrolidine derivatives of 37-40 are available via analogous routes.

Chemistry:

General. Melting points are uncorrected. CH$_2$Cl$_2$ was freshly distilled from CaH$_2$ under N$_2$. DMF was distilled under reduced pressure from ninhydrin and stored over 4 Å molecular sieves. Triethylamine was distilled from CaH$_2$ before use. Other solvents and reagents were used as obtained from commercial suppliers. For BOC removal, 4 M HCl in dioxane from was used. Column chromatography was carried out by using low air pressure (typically 6 psi) with 230-400 mesh silica gel 60. Routine $^1$H-NMR spectra were obtained on a Bruker AC-300 and are referenced to residual protonated NMR solvent. Routine $^{13}$C-NMR spectra were obtained on a Bruker AC-300 and are referenced to the NMR solvent. High resolution electron impact mass spectroscopy was performed on a Kratos MS-80RFA spectrometer with DS55/DS90.

Infrared Spectroscopy. Spectra were obtained on a Nicolet Model 740 FT-IR spectrometer. IR samples were prepared under anhydrous conditions; CH$_2$Cl$_2$ was freshly distilled from CaH$_2$, compounds and glassware were dried under vacuum for 1-2 days, and solutions were prepared under a nitrogen atmosphere. The pure solvent spectrum for a particular solution was subtracted from the sample spectrum prior to analysis. Peaks in the amide NH stretch region were baseline corrected, and analyzed without further manipulation.

NMR Spectroscopy:

Conformational Analysis. NMR samples for conformational analysis were prepared by dissolving the dry compound in dry deuterated solvent under a nitrogen atmosphere. CD$_2$Cl$_2$ samples were then degassed by the freeze-pump-thaw method, and the NMR tubes were sealed under vacuum. Methanol and aqueous samples were sealed with a close fitting cap and parafilm. COSY spectra were obtained on a Bruker AC-300 spectrometer. TOCSY, Braunschweiler et al. (1983); NOESY, Macura & Ernst (1980); and ROESY, Bothner-By et al. (1984) spectra were acquired on a Varian Unity-500 spectrometer using standard Varian pulse sequences and hypercomplex phase cycling (States-Haberkorn method), and the data were processed with Varian "VNMR" version 5.1 software. Proton signals were assigned via COSY and TOCSY spectra, and NOESY and ROESY spectra provided the data used in the conformational analyses. TOCSY spectra were recorded with 2048 points in t$_1$, 320 or 350 points in t$_2$, and 8 or 40 scans per t$_2$ increment. NOESY and ROESY spectra were recorded with a similar number of t$_1$, and t$_2$ points, and 32 and 40 scans per t$_2$ increment, depending on the sample concentration. The width of the spectral window examined was between 2000 and 4000 Hz.

Far UV Circular Dichroism (CD). Data were obtained on a Iasco J-715 instrument at 20° C. In all CD plots contained herein, the mean residue ellipticity is presented on the vertical axis. Presenting the mean residue ellipticity is a standard practice in peptide chemistry wherein the intensity of each CD spectrum is normalized for the number of amide chromophores in the peptide backbone. Consequently, when the intensities of the maximum and minimum peaks characteristic of secondary structure formation increase with increasing chain length, this change represents an increase in the population of the secondary structure, rather than simply an increase in the number of chromophores present in each molecule.

Solid-Phase and Solution-Phase Polypeptide Synthesis:

Construction of polypeptides using any type of α- and/or β- and/or γ-amino acid residue can be accomplished using conventional and widely recognized solid-phase or solution-phase synthesis. Very briefly, in solid-phase synthesis, the desired C-terminal amino acid residue is linked to a polystyrene support as a benzyl ester. The amino group of each subsequent amino acid to be added to the N-terminus of the growing peptide chain is protected with Boc, Fmoc, or another suitable protecting group. Likewise, the carboxylic acid group of each subsequent amino acid to be added to the chain is activated with DCC and reacted so that the N-terminus of the growing chain always bears a removable protecting group. The process is repeated (with much rinsing of the beads between each step) until the desired polypeptide is completed. In the classic route, the N-terminus of the growing chain is protected with a Boc group, which is removed using trifluoracetic acid, leaving behind a protonated amino group. Triethylamine is used to remove the proton from the N-terminus of the chain, leaving a free amino group, which is then reacted with the activated carboxylic acid group from a new protected amino acid. When the desired chain length is reached, a strong acid, such as hydrogen bromide in trifluoracetic acid, is used to both cleave the C-terminus from the polystyrene support and to remove the N-terminus protecting group.

The preferred solid-phase synthesis used herein is shown in Reaction 7. Solid-phase peptide synthesis is widely employed and well known. Consequently, it will not be described in any further detail here. See, for example, "Peptide Synthesis, Structures, and Applications" © 1995 by Academic Press. Chapter 3 of this book, dealing with solid-phase peptide synthesis, is attached hereto and incorporated herein by reference. Many of the subject heterogenous α-, β- and/or γ-peptides can be made using the solid phase approaches described in this reference.

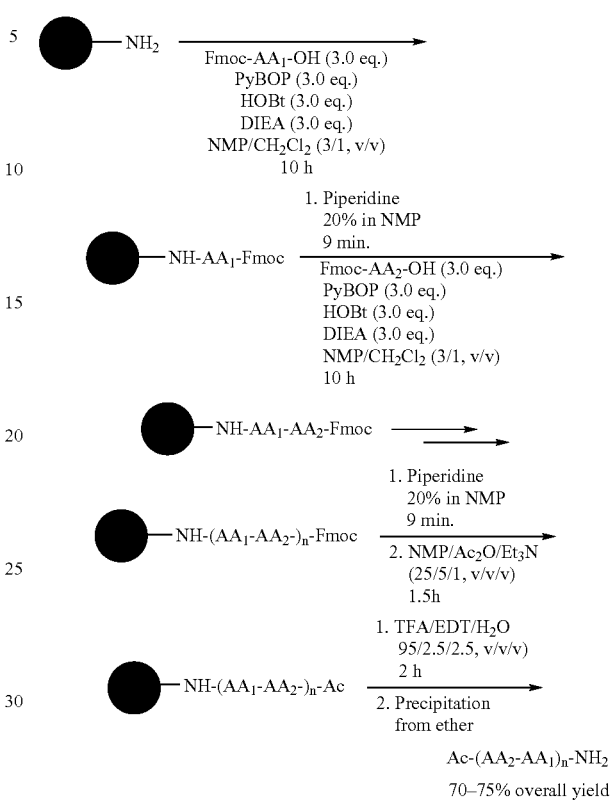

Solution phase synthesis, noted above, can also be used with equal success. For example, solution-phase synthesis of a γ-peptide chain can be accomplished as illustrated in the following coupling reaction:

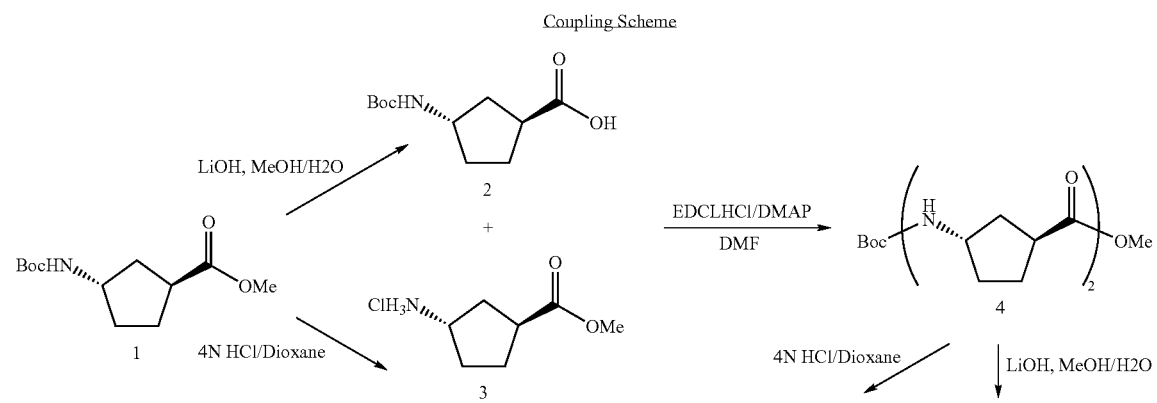

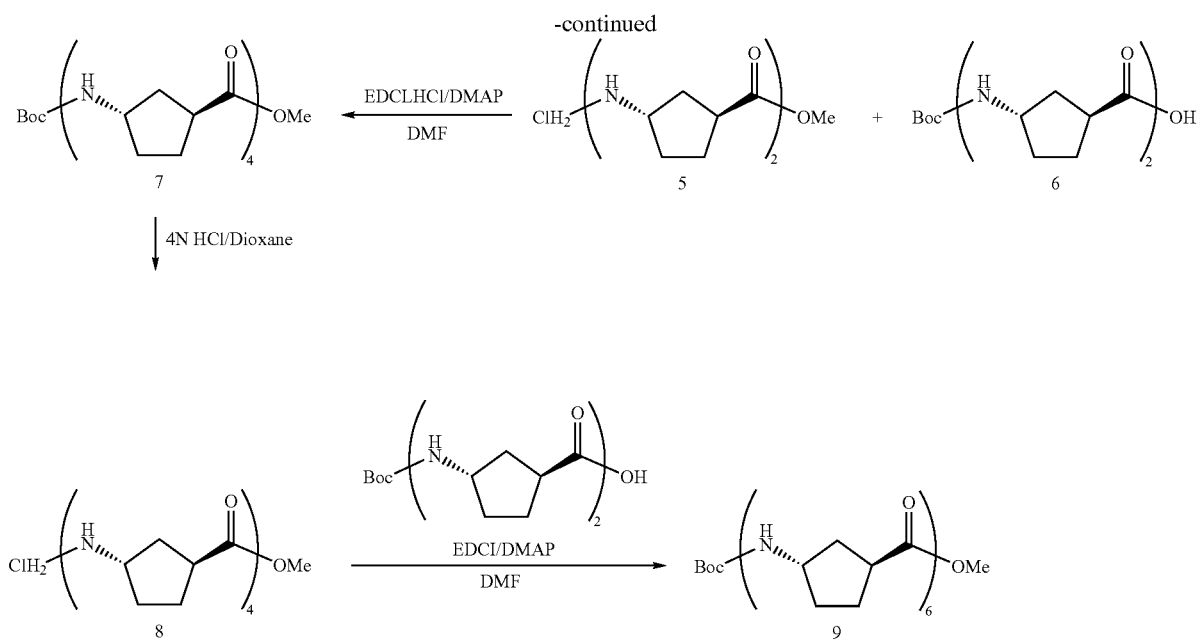

Compound 6: In 10 ml 5:1 MeOH:$H_2O$ 4 (1.8 mmol) was dissolved. $LiOH.H_2O$ (2.71 mmol) was added as a concentrated aqueous solution dropwise, maintaining the pH below 11. Solution stirred at RT 5 h. Neutralized with 0.5 M $NaHSO_4$ and evaporated MeOH. Acidified aqueous layer to pH 2. Extracted with EtOAc 2×. Dried Organics with $MgSO_4$. 1.61 mmol of product was recovered, a white crystalline product. 93%.

Compound 7: To 0.56 mmol 4 was added 2 mL 4N HCl; in dioxane. After stirring at RT for one hour solvents were removed under a stream of nitrogen. Remaining residue was dissolved in DMF (3 mL). To the solution was added 6 (0.56 mmol), followed by DMAP (0.75 mmol), and EDCI (1.25 mmol). Solution stirred at RT 12 h. After about 1 h. a white precipitate could be seen forming. 1 M HCl (2 mL) was added and the precipitate was filtered off and washed with water. Residue was then chromatographed with 20:1 $CH_2Cl_2$: MeOH. The product, a white powdery solid, was recovered in 88% yield. NMR was taken in 1:1 $CDCl_3$:$CD_3OD$ due to poor solubility in other solvents.

All other compounds were synthesized in similar fashion. The hexamer 9 could not be chromatographed due to solubility issues, but was isolated pure by precipitation.

Figure 5:
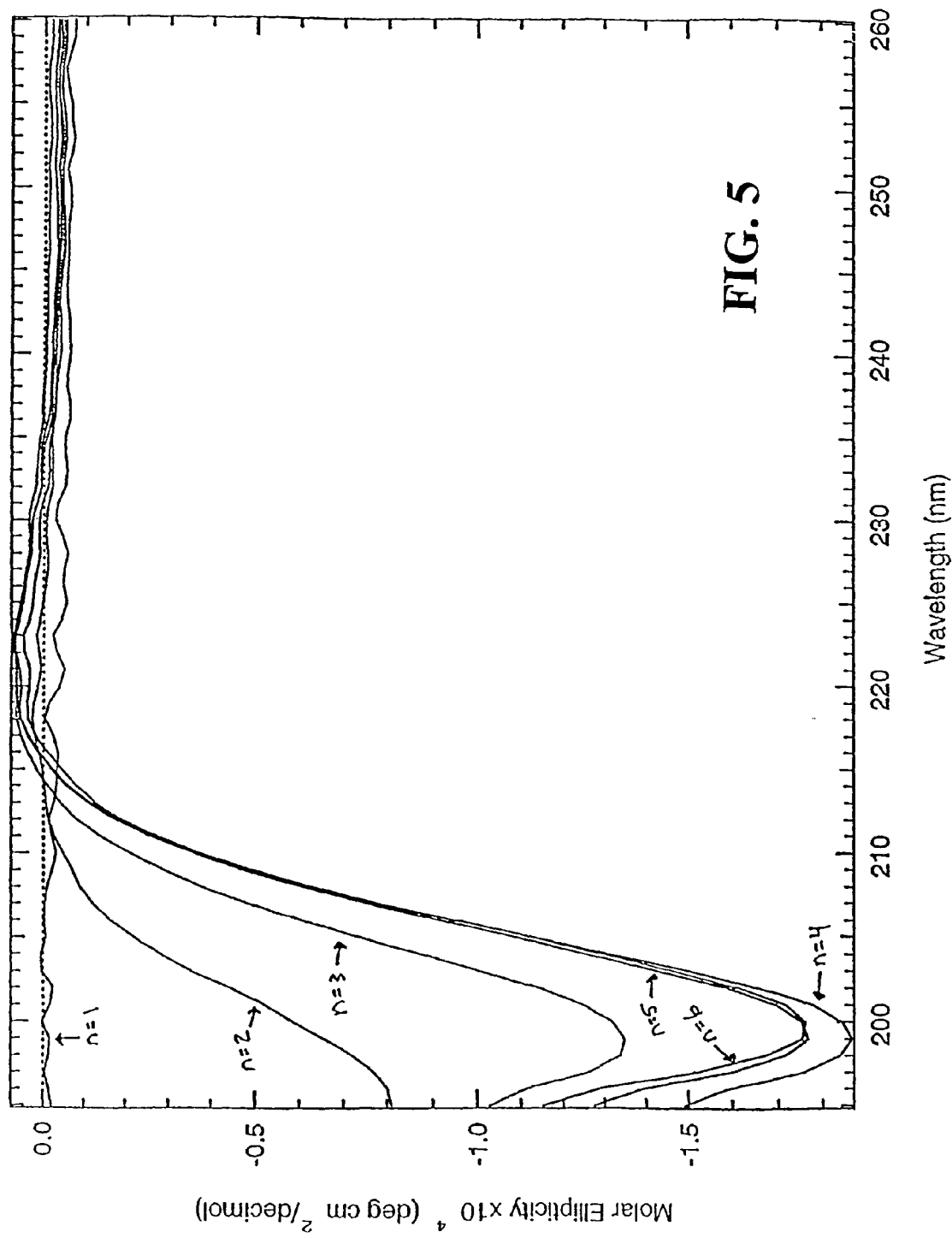

FIG. 5 is a series of superimposed CD spectra of the series leading from the monomer to the hexamer in the above coupling scheme. The spectra show the development of a characteristic minimum at about 190 nm, indicating the development of secondary conformation.

Adding Substituents to the Cyclic Moiety:

As noted above, the heterogeneous peptides of the present invention can be substituted with any number of substituents, including hydroxy, linear or branched $C_1$-$C_6$-alkyl, alkenyl, alkynyl; hydroxy-$C_1$-$C_6$-alkyl, amino-$C_1$-$C_6$-alkyl, $C_1$-$C_6$-alkyloxy, $C_1$-$C_6$-alkyloxy-$C_1$-$C_6$-alkyl, amino, mono- or di-$C_1$-$C_6$-alkylamino, carboxamido, carboxamido-$C_1$-$C_6$-alkyl, sulfonamido, sulfonamido-$C_1$-$C_6$-alkyl, urea, cyano, fluoro, thio, $C_1$-$C_6$-alkylthio, mono- or bicyclic aryl, mono- or bicyclic heteroaryl having up to 5 heteroatoms selected from N, O, and S; mono- or bicyclic aryl-$C_1$-$C_6$-alkyl, heteroaryl-$C_1$-$C_6$-alkyl, and combinations thereof. Effecting such substitutions is well within the set of skills possessed by a synthetic peptide chemist.

For example, appending a sulfonamido moiety to the cyclic backbone substituent can be accomplished in conventional fashion using Reaction 10. This reaction depicts the addition of a sulfonamido moiety to the cyclic back bone of a β-peptide. The same approach, however, will function using the analogous γ-peptide starting materials.

Compound 63: Compound 61 (90 mg) was dissolved in 4 N HCl in dioxane (2.0 ml). The reaction mixture was stirred for 1.5 hours. The dioxane was then removed in vacuo. The residue was dissolved in pyridine (2.0 ml), then cooled to 0° C. in an ice-bath.

Methanesulfonylchloride (71 µL) was added dropwise. After the addition, the reaction mixture was stirred at room temperature for 12 hours. The pyridine was then removed in vacuo. The residue was taken up in ethyl acetate (50 ml). The mixture was washed with dilute brine (2×10 ml), dried over $MgSO_4$, and concentrated to give the clean product as a colorless oil (70 mg) in 82% yield.

Compound 64: Compound 62 (30 mg) was dissolved in 4 N HCl in dioxane (2.0 ml). The reaction mixture was stirred for 1.5 hours. The dioxane was then removed in vacuo. The residue was dissolved in pyridine (1.0 ml), then cooled to 0° C. in an ice-bath. Toluenesulfonylchloride (63 mg) was added in portions. After the addition, the reaction mixture was stirred at room temperature for 12 tours. The pyridine was then removed in vacuo. The residue was taken up in methylene chloride/diethyl ether (1/1, v/v, 100 ml). The mixture was washed with dilute brine (3×20 ml), dried over $MgSO_4$, and concentrated to give a liquid residue. The crude product was purified by column chromatography with ethyl acetate/hexane (4/6, v/v) as eluent to give the clean product as a colorless oil (25 g) in 74% yield.

Analogous reactions will append a carboxyamido group.

REACTION 10

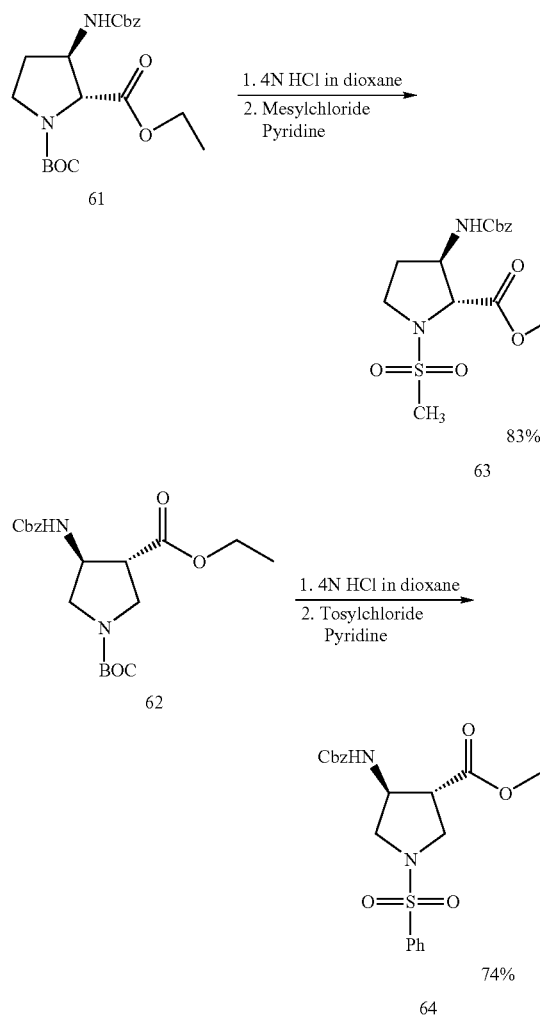

Synthesis and Characterization of Heterogeneous Oligomers:

Heterogeneous oligomers of alternating trans-2-amino cyclohexanecarboxylic acid (ACHC) with various α-amino acids were designed and synthesized to study their conformational properties. Heterogeneous oligomers were synthesized by both solution-phase and solid-phase methods. Standard coupling reagents were used with the coupling proceeding from the C-terminus toward the N-terminus. For efficient coupling to be effected, it is desirable to obtain the monomer in a pure form. It is also important to use protective groups that are tolerant to reaction conditions. For solution-phase synthesis, tert-butyloxycarbonyl (Boc) group was used for N-terminus protection, while the benzyl group was used for C-terminus protection. The α-amino acids were obtained commercially and were used without further purification. The desired α-amino acids for solution-phase synthesis were those protected with the Boc group at the N-terminus and having a free carboxylic acid terminus. For solid-phase synthesis, the desired α-amino acids were those protected with 9-fluorenylmethyloxycarbonyl (Fmoc) at the N-terminus. The side chains of those α-amino acids containing reactive groups were also protected to prevent unwanted side-chain reactions. The β-amino acid required for coupling, trans-2-aminocyclohexanecarboxylic acid (ACHC), in either the Boc- or Fmoc-protected form was synthesized and purified as described in the Examples. The optical rotation was checked to make sure the monomer was sufficiently pure for coupling.

Solution Phase Synthesis:

As earlier mentioned, coupling was designed to proceed from the C-towards the N-terminus. A retro synthetic analysis is shown in Scheme 1 below. A sequential coupling strategy was employed starting with the synthesis of the dimeric backbone.

Scheme 1. Retro synthetic Scheme for Oligomer Synthesis.

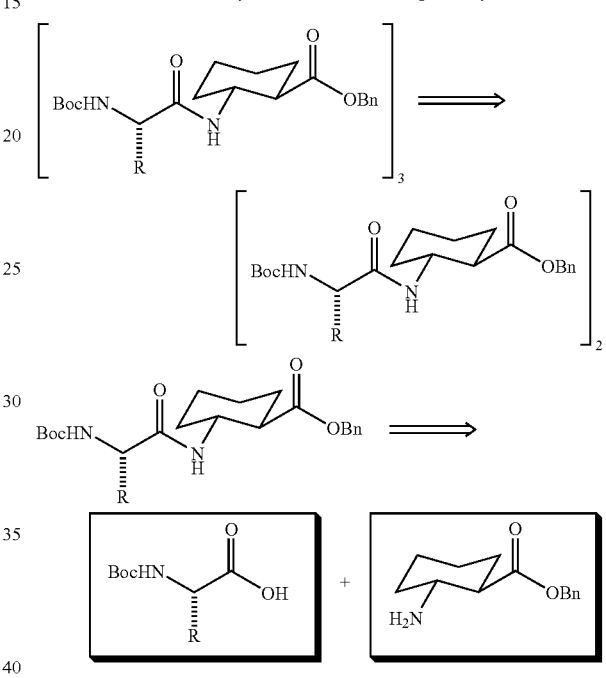

Synthesis of Dimer: The dimer synthesis was accomplished starting with the Boc-protected α-amino acid as the electrophile. The β-amino acid protected by a Boc group at the N-terminus and a benzyl group at the C-terminus was deprotected at the N-terminus to form a free amine that would serve as the nucleophile. Standard deprotection methods involving the use of 4N HCl in dioxane to deprotect the Boc group was carried out as shown in the following scheme. Once the Boc group was deprotected, the free amine was then coupled to the free acid using standard coupling reagents. Dimer couplings generally went for an average of 48 hours and the yields were usually very good to excellent, even after column chromatography. The various dimers that were synthesized and the yields are shown in Table 1.

Dimerization of ACHC with α-Amino Acids.

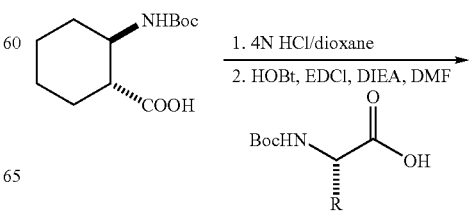

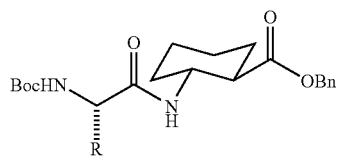

TABLE 1

Heterogeneous Dimers and their Yields

| Dimer | % Yield |
| --- | --- |
| Boc-Ala-ACHC-OBn | 92 |
| Boc-Phe-ACHC-OBn | 94 |
| Boc-Val-ACHC-OBn | 80 |

Synthesis of Trimer, Tetramer and Higher: A sequential or stepwise coupling from the dimer was employed to synthesize oligomers with three or more residues. A general synthetic route leading to oligomers beyond the dimer is shown in the following Scheme Synthesis was quite simple to the level of the tetramer, but beyond the tetramer solubility becomes a concern and yields drop.

A series of oligomers were synthesized having β-amino acids on the interior, and α-amino acids at the N- and C-termini. The idea here was to investigate the effect of terminal α-amino acids on the conformation of a chain of β-amino acids. The various oligomers synthesized and their yields are shown in Tables 2 and 3.

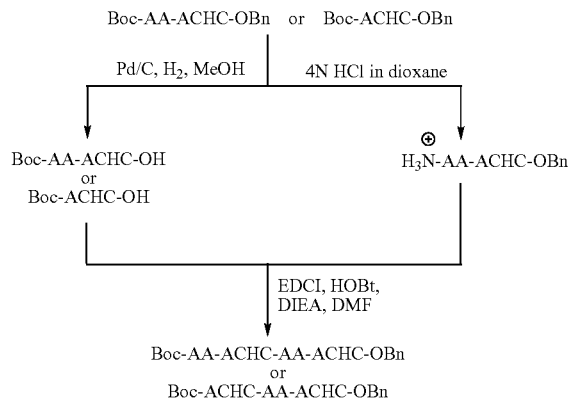

Scheme 2. Synthetic Route to Oligomers with more than 3 Residues; AA = α-amino acid

TABLE 2

Heterogeneous Trimers and their Yields

| Trimer | % Yield |
| --- | --- |
| Boc-Val-Phe-ACHC-OBn | 85% |
| Boc-ACHC-Phe-ACHC-OBn | 52% |
| Boc-ACHC-Val-ACHC-OBn | 62% |
| Boc-Lys(2-Cl-Z)-Val-ACHC-OBn | 84% |

TABLE 3

Heterogeneous Tetramers and their Yields

| Tetramer | % Yield |
| --- | --- |
| Boc-Ala-ACHC-Ala-ACHC-OBn | 75% |
| Boc-Phe-ACHC-Phe-ACHC-OBn | 72% |
| Boc-Val-ACHC-Val-ACHC-Val-OBn | 80% |
| Boc-Lys(2-Cl-Z)-Val-Phe-ACHC-OBn | 60% |
| Boc-Lys(2-Cl-Z)-ACHC-Val-ACHC-OBn | 90% |
| Boc-ACHC-Lys(2-Cl-Z)-Val-ACHC-OBn | 75% |

Solid Phase Synthesis:

Oligomers were synthesized following the general protocol of solid-phase synthesis. The general protocol involves deprotection, activation, and coupling. Extended deprotection, extended coupling, and extended flushes were employed to ensure that synthesis was complete. The columns in the synthesizer were loaded with a three-fold excess of the calculated stoichiometric amount of amino acid needed for coupling. N,N-Dimethylformamide was used as solvent, while HBTU and DIEA reagents were the activators. The purpose of the activators is to convert the carboxyl group to an active ester, which then reacts with the deprotected incoming amino acid. HOBt is an additive whose purpose is to suppress any possible racemization and to accelerate aminolysis. Piperidine and DMF serve to deprotect the Fmoc-protected amino group on the peptide resin in preparation for coupling. THF is used as a secondary solvent to clean the column of primary solvent after synthesis. At the end of the synthesis, the peptide is acetylated and rinsed. The peptide is then cleaved from the resin by a protocol involving the use of 95:2.5:2.5 TFA:ethanedithiol:H$_2$O and stirring for about 5 hours. The peptide is further isolated by precipitation and purified by HPLC. A general route for solid phase synthesis is shown below (Scheme 3).

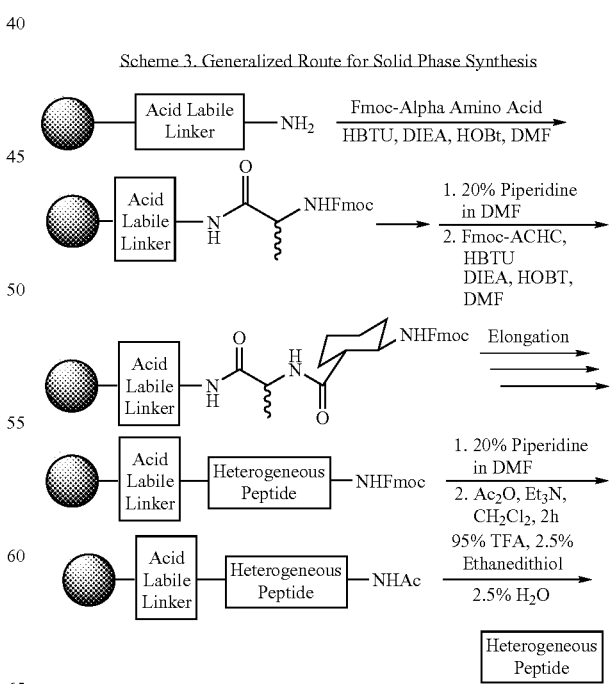

Scheme 3. Generalized Route for Solid Phase Synthesis

The various oligomers synthesized by solid phase methodology were as follows:
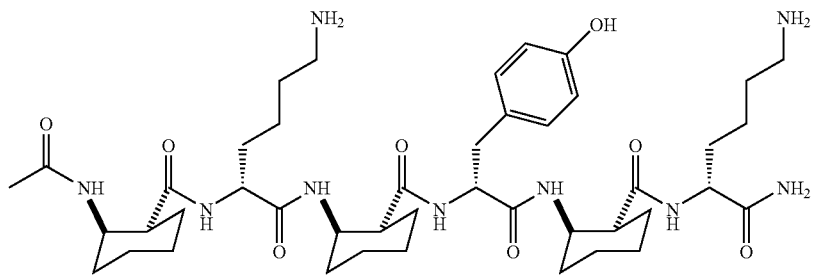
R,R-ACHC and D-Alpha Amino Acid
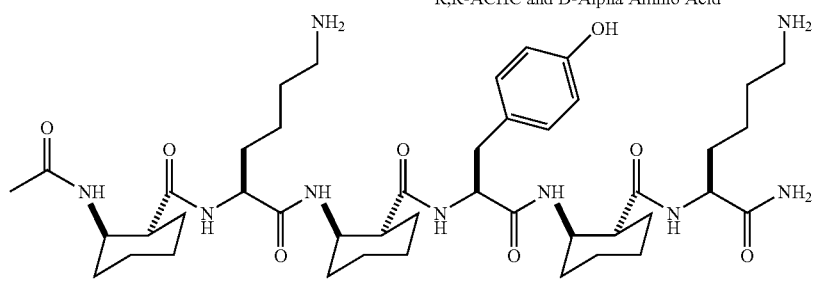
R,R-ACHC and L-Alpha Amino Acid
Heterogeneous Hexamers
30
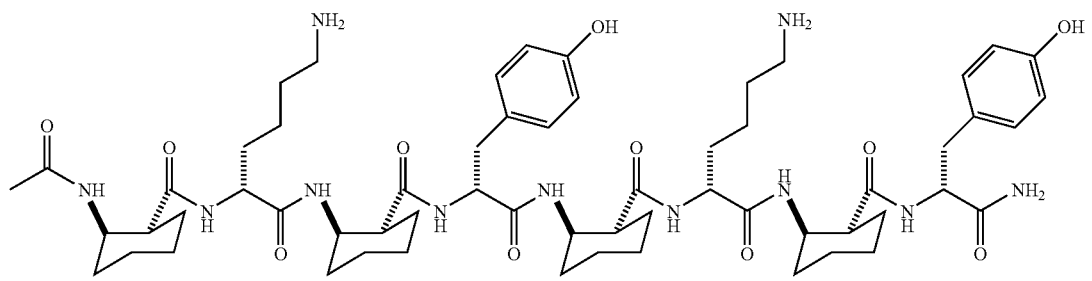
R,R-ACHC and D-Alpha Amino Acid
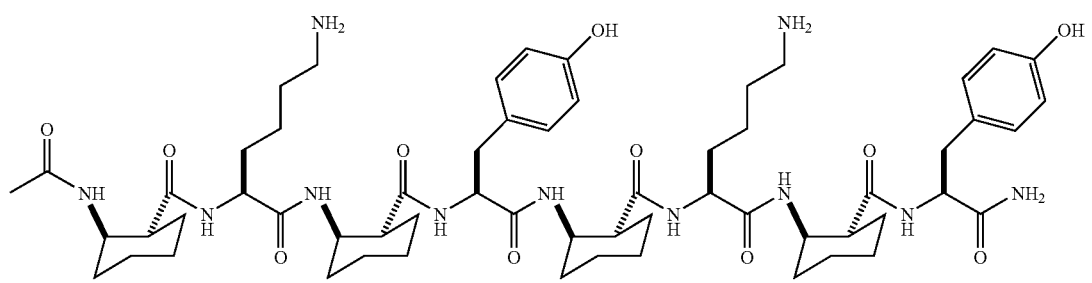
R,R-ACHC and L-Alpha Amino Acid

Heterogeneous Octamers

Heterogeneous Oligomers Comprising ACPC and an Aromatic Monomer:

The following scheme describes the synthesis of aromatic amino acid derivative 7, starting from commercially available methyl 3,5-dinitrobenzoate. Compound 3 in this scheme has been synthesized in the prior art, see Herlt et al. (1981).

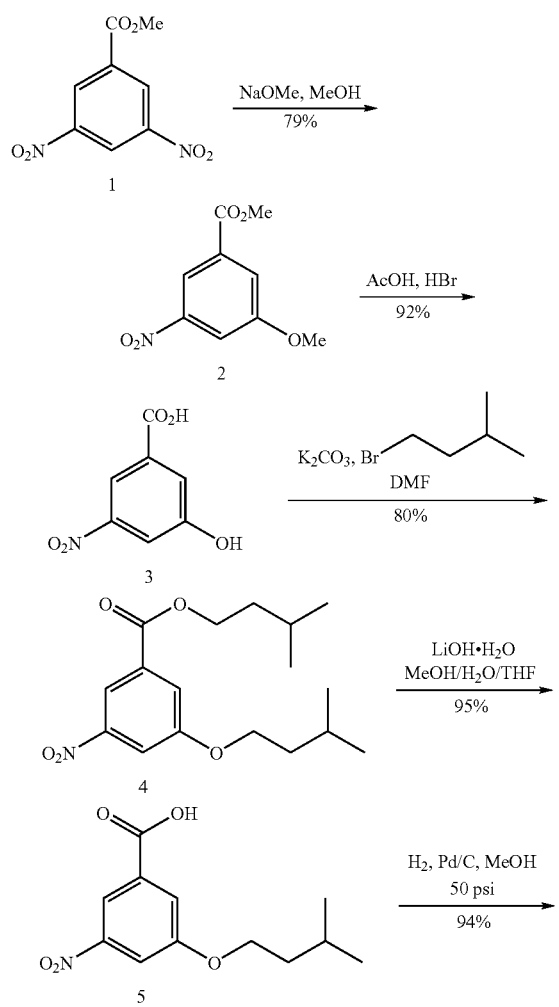

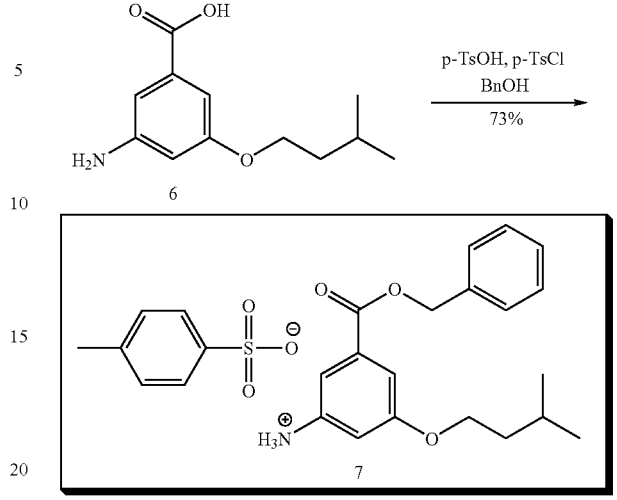

The β-amino acid monomer, (trans) Boc-ACPC-OH was synthesized according to a LaPlae et al. (2001):

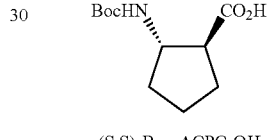

(S,S)-Boc-ACPC-OH

The syntheses of oligomers containing these monomers (from the dimer to the octamer) is illustrated in the following scheme. Coupling reactions were accomplished in solution using chlorotripyrrolidinophosphonium hexafluorophosphate (PyCloP) in combination with DIEA as base, in either methylene chloride or DMF, DMAP was added in sub-stoichiometrical amounts. The oligomers were deprotected for further segment couplings by 4N HCl in dioxane (N-terminus) and transfer hydrogenation (C-terminus). Compounds 8-11 as shown in the following scheme were purified by column chromatography.

1) dimer formation

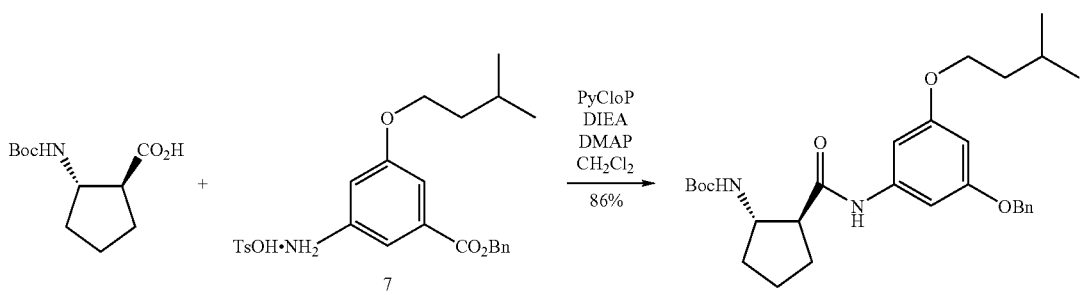

2) dimer deprotection

-continued

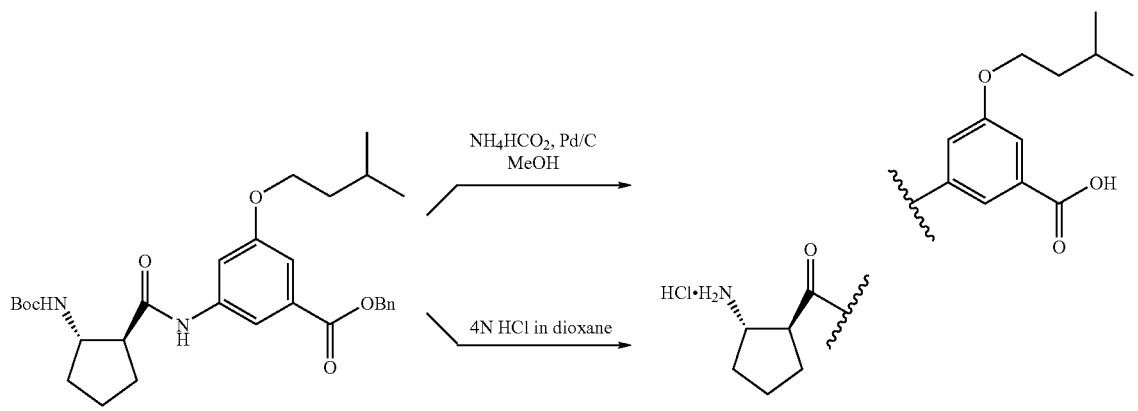

3) tetramer formation: 78% yield, procedure same as before

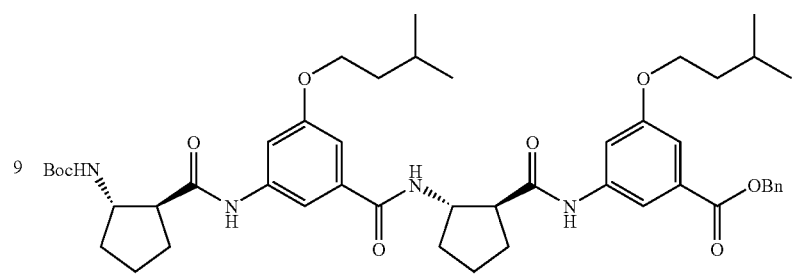

4) tetramer deprotection
5) hexamer formation: 78% yield, procedure same as before

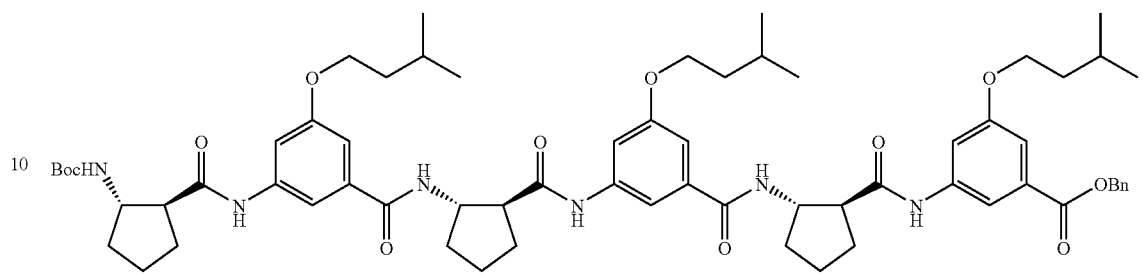

6) hexamer deprotection
7) octamer formation (70% yield, procedure same as before)

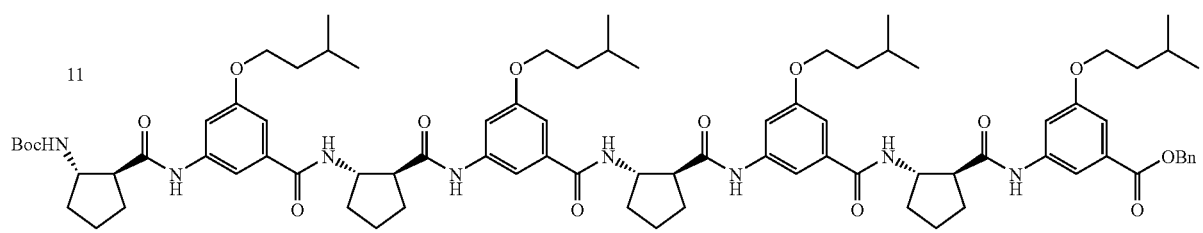

Heterogeneous Oligomers Comprising ACPC and an α-Amino Acid:

Heterogeneous oligomers containing a series of alternating ACPC and α-amino acid monomers, synthesized by automated solid phase synthesis, are presented below as compounds 12-15. Three hexamers and one octamer with the motif Ac-ACPC-K-ACPC-Y-ACPC-K(-ACPC-Y)-NH$_2$, comprising different stereochemical combinations, were synthesized. A "SYNERGY"-brand automated peptide synthesizer (Applied Biosystems Model 432A) was used to carry out the synthesis. The programming used for the automated syntheses came packaged with the synthesizer.

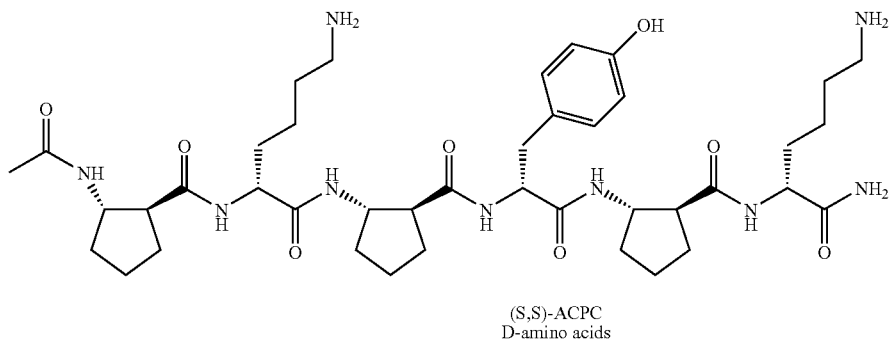
(S,S)-ACPC
D-amino acids
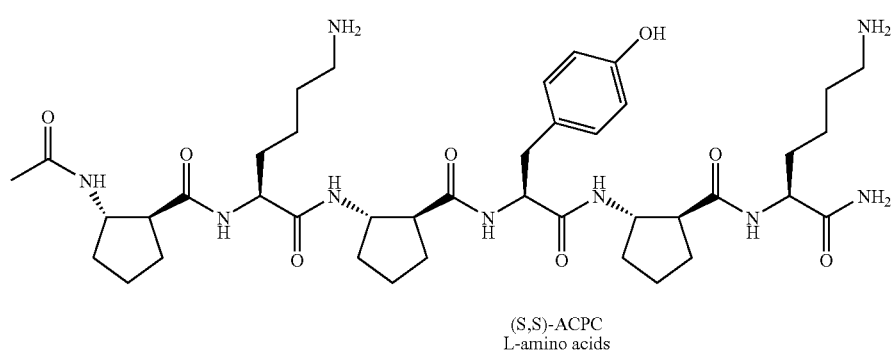
(S,S)-ACPC
L-amino acids
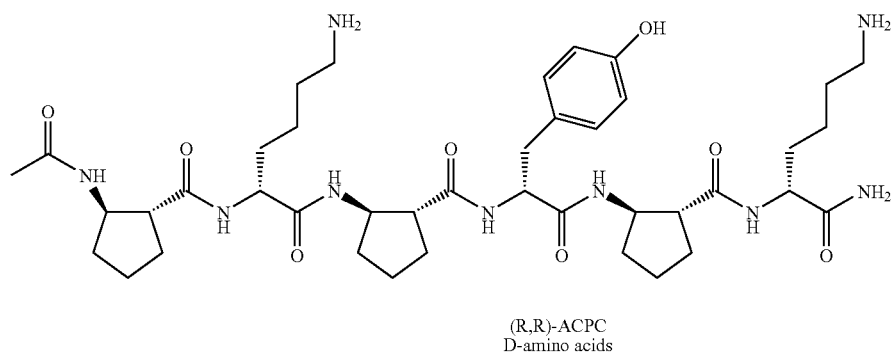
(R,R)-ACPC
D-amino acids
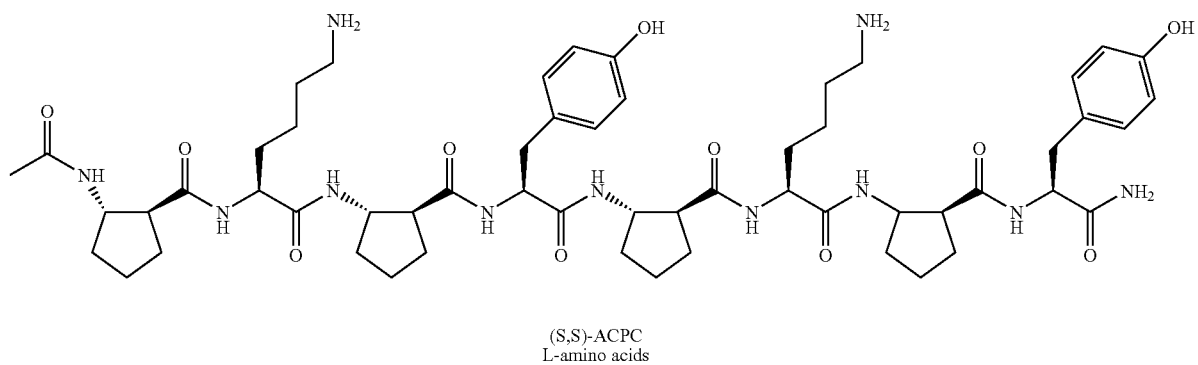
(S,S)-ACPC
L-amino acids CD spectra of compounds 12-15, immediately above, are shown in FIGS. 6A and 6B. FIG. 6A depicts the CD spectra for each of compounds 12-15 at a concentration of 1 mM in methanol. FIG. 6B depicts the CD spectra for each of compounds 12-15 at a concentration of 1 mM in aqueous Tris buffer (10 mM).

NOE's for compounds 12 and 13 were also gathered, with the results as follows:

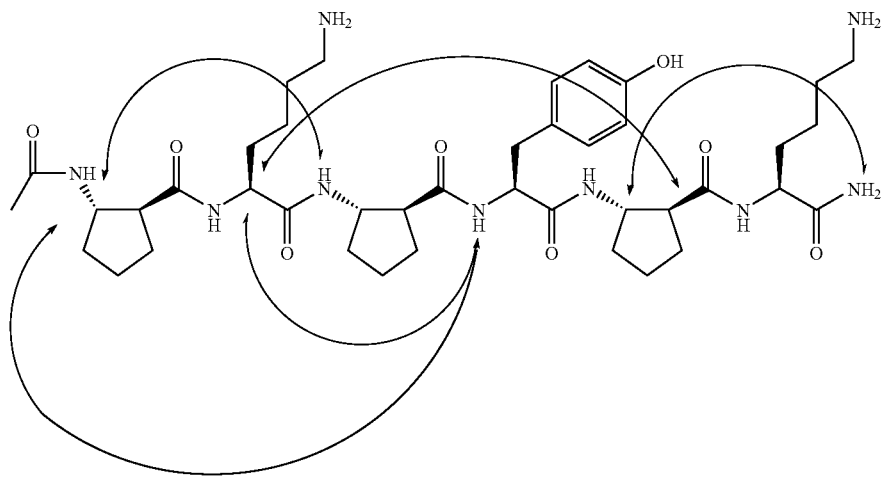

NOEs observed in ROESY analysis for ~3 mM solution in CD$_3$OH at 14° C. Only unambiguously assigned NOEs are shown. Additional long-range NOEs were observed, but spectral overlap interfered with their assignment. Resonance assignments were made based upon COSY and TOCSY data, as well as sequential NOEs from ROESY data.

No long-range NOEs were observed for the hexamer containing D alpha amino acids.

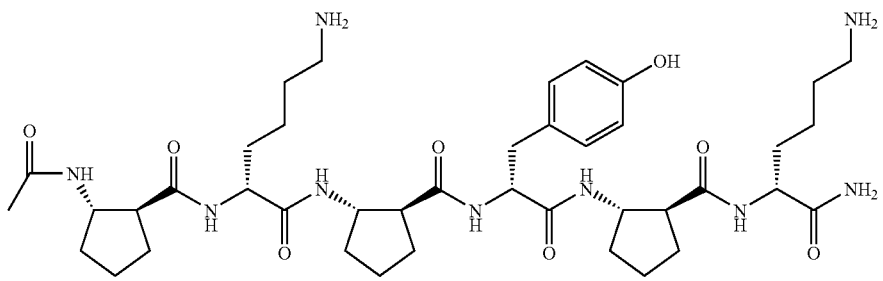

Data collected for ~2-3 mM solution in 9:1 H$_2$O:D$_2$O, buffered to pH 3.8 with deuterated acetic acid at 14° C. Assignment in CD$_3$OH was not possible due to resonance overlap.

Selected Heterogeneous Foldamer Designs:

Representative structures of this class of compounds include examples such as 10a and 10b, which comprise repeating blocks of α, β, β, residues:

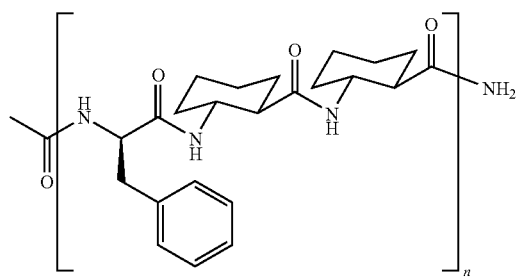

10a

-continued

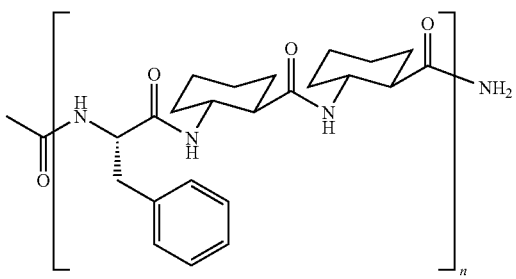

10b

Antiparallel sheet secondary structure among β-peptides is promoted by use of α,β-disubstituted residues with the stereochemistry illustrated below. Sheet formation should occur between α/β-strand segments containing a regular 1:1 alternation of residues in molecules such as 13.

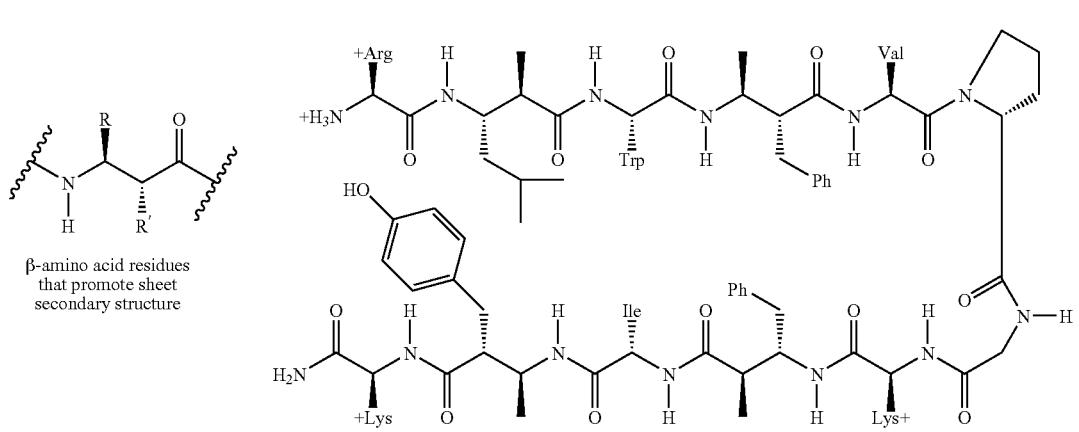

13

β-amino acid residues that promote sheet secondary structure

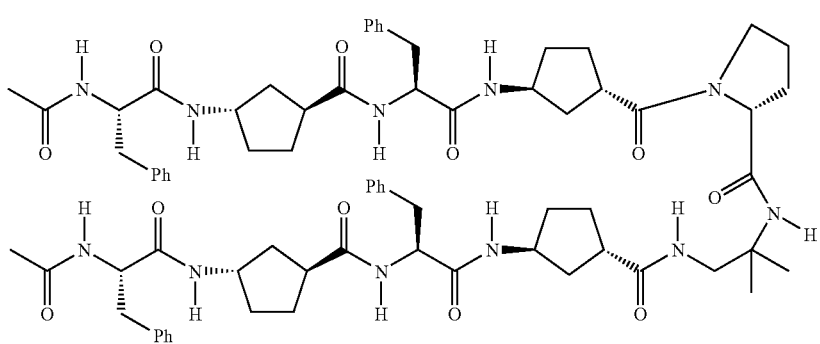

14

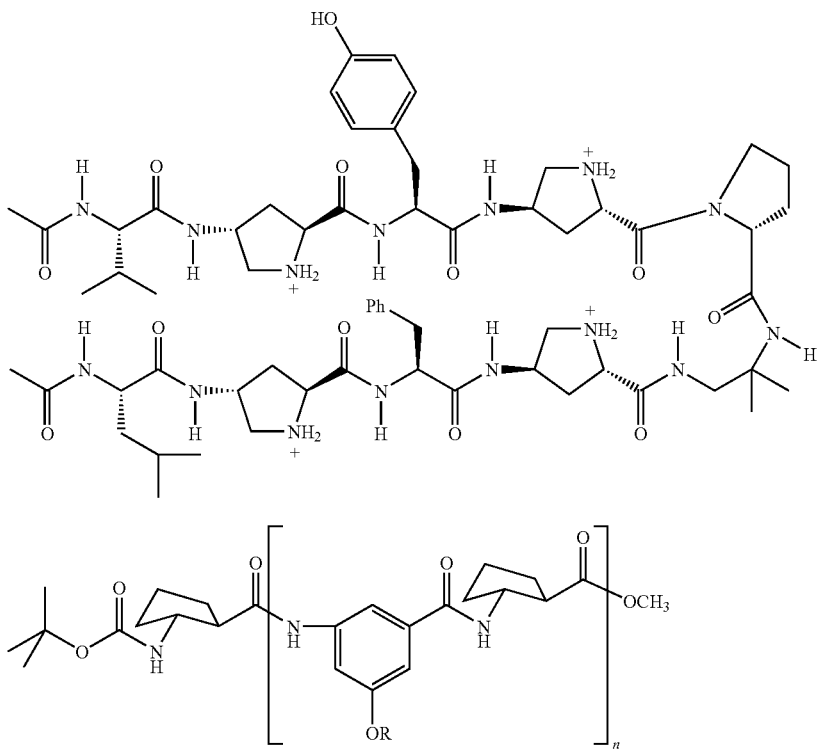

The strands are connected by a D-Pro-Gly linker, a strong promoter of hairpin formation among a-peptides with L-residue strands. (Note: In this case the strands have strict α/β alternation, but these strands are connected by a loop segment that does not happen to conform to this alternating pattern. In this case the loop is two α-residues, but in other hairpin-shaped molecules below the loop can have other compositions. For example, in 14 and 15, the loop is a diamine segment.)

Hetero-oligomer 13 is designed to have a well-defined cluster of hydrophobic sidechains. The net charge of +4 should be sufficient to inhibit self-association.

Compounds like 13 are interesting at a fundamental level because we predict that sheet secondary structure for mixed α,β-residue strands should be much more stable than for pure α-residue strands, based on the intrinsic preorganization of the β-amino acid residues. Backbone-backbone interactions alone between α-peptide strands are not sufficient to allow propagation of sheet structure out from a linker; sidechain-sidechain interstrand contacts are critical for stability of β-hairpins built from α-amino acid residues. We expect, however, that hairpins with heterogeneous α/β-backbones will fold in water even in the absence of favorable interstrand sidechain-sidechain contacts because the preorganized β-amino acid residues will lead to a greater stabilizing contribution from backbone-backbone interactions. We can test this hypothesis with derivatives of 13, if 13 itself folds as proposed. In this case, we would examine analogues with progressively fewer large nonpolar sidechains (e.g., convert Trp to Ala, convert Ile to Ala, convert both of these residues to Ala). Precise quantitative comparison of hairpin populations among 13 and variants might be difficult to achieve; however, comparison of NOE intensities along this series, calibrated against intramolecular NOEs from geminal or vicinal protons (known spatial separation), would allow at least a qualitative comparison.

If the hairpin population of 13 and variants is not significantly affected by loss of interstrand hydrophobic contacts, then we can conclude that backbone contacts constitute the major source of conformational stability in these foldamers. This result would be useful from the perspective of biomedical applications, because the designer could place sidechains along this scaffold without concern for disrupting interstrand contacts required for conformational stability. In this context, it is important to note that the α/β-strands allow side-chain arrangements that are distinctive relative to those of either α- or β-peptide strands.

Oligomers containing both α- and γ-amino acid residues. The α/β-peptide designs described above can be extrapolated directly to α/γ designs once highly preorganized γ-amino acid residues are identified. We will examine oligomers like 14, which should display parallel sheet formation involving α/γ-strands in organic solvents. If 14 folds as planned, we will prepare 15 for study in aqueous solution. The γ-residue in 15 is readily available from 4-hydroxy-proline, and protonation of the ring nitrogen would provide the net positive charge necessary to avoid aggregation. We will use analogous designs, with a D-Pro-Gly or related linker, to examine antiparallel sheet formation between α/γ-strands. Design of other potential α/γ foldamers, e.g., for helix formation, will require appropriately preorganized γ-amino acid residues. Once we have identified the necessary γ-amino acid building blocks we will examine 1:1 and 2:1 α/γ-sequences analogous to those proposed above for α/β-backbones containing trans-2-ACHC and trans-2-ACPC.

Oligomers containing aromatic amino acids. We will evaluate heterogeneous backbones in which aromatic amino acids are combined with α-, β- or γ-amino acid residues for the ability to fold to specific secondary structures. The motivation for this effort is based on three qualities of the aromatic amino acids. (1) These building blocks are relatively rigid; therefore, aromatic amino acid residues may lead to oligomers with intrinsically limited conformational options. (2) The aromatic amino acids we examine will be achiral, and they should therefore be readily available in large quantities. We plan to develop efficient strategies for attachment of diverse sidechains to the aromatic rings (e.g., alkylation of a phenolic substituent), which would allow us to endow heterogeneous foldamers with functional diversity via achiral aromatic residues while promoting a specific chiral folding pattern with one rigid chiral residue that could be prepared on large scale. (3) Incorporating aromatic units into the oligomer backbone raises the possibility of using aromatic-aromatic interactions to stabilize specific folding patterns.

β/aromatic oligomer 20 is another promising design. Related backbones containing other preorganized β- or γ-amino acids and/or other aromatic amino acids may also be envisaged in light of the above-described variations.

For example, the following series of compounds can be fabricated using the above-described methods:

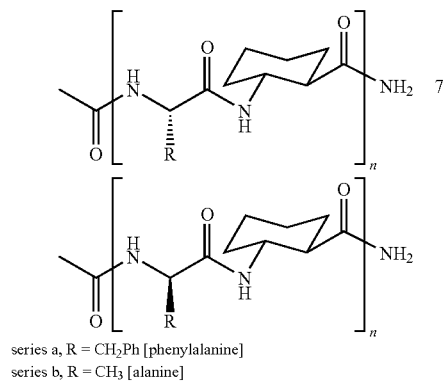

series a, R = CH$_2$Ph [phenylalanine]
series b, R = CH$_3$ [alanine]

See the Examples section for additional derivatives that can be fabricated using the above-described techniques.

EXAMPLES

The following Examples are included solely to provide a more complete and consistent understanding of the invention disclosed and claimed herein. The Examples do not limit the scope of the invention in any fashion.

Solution Phase Synthesis:

General Procedures. Melting points (m.p.) were obtained on a Thomas Hoover Capillary Melting Point Apparatus and are uncorrected. Optical rotations were measured on a Perkin-Elmer 241 digital polarimeter using sodium light (D line, 589.3 nm) and are reported in degrees; concentrations (c) are reported in g/100 mL. Proton nuclear magnetic resonance ($^1$H NMR) were recorded in deuterated solvents on a Bruker AC-300 (300 MHz) spectrometer. Chemical shifts are reported in parts per million (ppm, δ) relative to tetramethysilane (δ 0.00). In the absence of tetramethylsilane in the deuterated solvent, the standard chemical shift of the solvent is referenced (CDCl$_3$, δ 7.26; CD$_3$OD, δ 3.30). For mixed solutions of CDCl$_3$ and CD$_3$OD, CDCl$_3$ is referenced. $^1$H NMR splitting patterns are designated as singlet (s), doublet (d), triplet (t), quartet (q), or quintet (quint). All first order splitting patterns are assigned based on the appearance of the multiplet. For those splitting patterns that could not be easily visualized or interpreted, a designation of multiplet (m) or broad (br) was used. Coupling constants are reported in Hertz (Hz). Carbon nuclear magnetic resonance ($^{13}$C NMR) spectra were recorded on a Bruker AC-300 spectrometer. Chemical shifts are reported in ppm (δ) relative to the central line of the CDCl$_3$ triplet (δ 77.0), or the CD$_3$OD septet (δ 49.0). Carbon NMR data were assigned using distortionless enhancement by polarization transfer (DEPT) spectra obtained with a phase angle of 135°: (C) not observed; (CH) positive; (CH$_2$) negative; (CH$_3$) positive. Electrospray ionization (ESI) mass spectra were determined on a Kratos MS-80 mass spectrometer. Dry ethanol was prepared by distillation from diethyl phthalate and sodium. Dry methanol was prepared by distillation from Mg(OMe)$_2$ (Mg turnings (5 g), I2 (0.5 g), methanol (100 mL)). Benzene was freshly distilled from Na/benzophenone ketyl and stored under N$_2$. Methylene chloride was distilled from CaH$_2$. Hexane was distilled at atmospheric pressure. Diisopropylethylamine (DIEA) was distilled from CaH$_2$. Unless otherwise noted, all other commercially available reagents and solvents were used without further purification. All commercially available reagents and solvents, unless stated otherwise, were purchased from Aldrich, except for 4 N HCl in dioxane, which was purchased from Pierce. Analytical thin-layer chromatography (TLC) was carried out on Whatman TLC plates precoated with silica gel 60 (250 μm layer thickness). Visualization was accomplished using either a UV lamp, potassium permanganate stain (2 g of KMnO$_4$, 13.3 g of K$_2$CO$_3$, 3.3 mL of 5% (w/w) NaOH, 200 mL of H$_2$O), ninhydrin stain (0.5 g of ninhydrin, 150 mL of n-butanol, 5 mL of glacial acetic acid), or phosphomolybdic acid in ethanol. Column chromatography was performed on EM Science silica gel 60 (230-400 mesh). Solvent mixtures used for TLC and column chromatography are reported in v/v ratios. All glassware was dried in an oven at 120° C.

Solid Phase Peptide Synthesis:

Peptide Synthesis:

Solid phase peptide synthesis was carried out using the automated peptide synthesizers Synergy or Pioneer, Applied Biosystems Model 432A (Foster City, Calif.). N-9-Fluorenyl-methyloxycarbonyl amino acids and 2,4-dimethoxybenzhydrylamine resin (Rink Amide) cartridges were obtained from E.I. du Pont de Nemours & Co., Inc. (Boston, Mass.) or Novabiochem (San Diego, Calif.) and advanced Chemtech (Louisville, Ky.). Peptide synthesis reagents such as DMF, piperidine, TFA, 1,2-ethanedithiol, thioanisole, 1-hydroxy-7-azabenzotriazole (HOAT), O-(7-azabenzotriazol-1-yl)-N,N,N',N'-trimethyluronium hexafluorophosphate (HATU), were all purchased from Aldrich Chemical Company (Milwaukee, Wis.) and were used without further purification. HBTU, HOBt, DIEA were purchased from Applied Biosystems (Foster City, Calif.).

Standard solid phase techniques with N$^α$-Fmoc-protected amino acids[1] using 2,4-dimethoxybenzhydrylamine resin (Rink Amide AM) cartridges on a 25 μmole scale were applied. The resins were either preloaded with the C-terminal amino acid or acid-labile amine. Synthesis proceeded from the C-terminal to N-terminal direction. Each coupling reaction was carried out at room temperature in DMF with three equivalents of amino acid. Coupling reactions were monitored by the conductivity of the solution. Reaction times were doubled to ensure that coupling was complete. The coupling reagents used were HBTU, HOBt, and DIEA as the base. In each step of the coupling, the chemicals were delivered at a scale of 75 μmoles which is three fold excess relative to the estimated resin capacity. For amino acids with reactive groups on their side chains, protection of the reactive groups was ensured to prevent unwanted side reactions. Notably the tyrosine and lysine side chains were protected with the tert-butyl and Boc-protected groups respectively.

At the end of each coupling reaction, the N-terminal Fmoc-protected amine was deprotected by applying 20% piperidine in DMF at room temperature for about 60 minutes. Fmoc deprotection reactions were also monitored by the solution conductivity. Upon addition of the last residue, the resin, still in the peptide synthesis column, was rinsed with methanol or methylene chloride and dried under a stream of nitrogen. The dried resin was transferred into a 10 mL round-bottom flask for the cleavage reaction.

To cleave the peptide from the resin, a solution consisting of 2.5% Millipore water and 2.5% ethanedithiol in TFA was used. The solution and resin were stirred at room temperature for approximately 5 to 6 hours. The resin beads were filtered off using a plug of glass wool and rinsed two to three times with additional TFA. TFA was blown off under a gentle stream of nitrogen. The peptide was isolated via precipitation. A minimal amount of MeOH was added to dissolve the peptide, and diethyl ether (10 mL) was added to form a white precipitate. The mixture was cooled in an acetone/dry ice bath for 5 minutes, and centrifuged at 3000-4000 rpm until the precipitate formed a pellet at the bottom of the centrifuge tube. The ether was decanted, and the pellet was resuspended in cold ether (10 mL) and centrifuged again; the process was repeated three times. During the final wash 10 mL of Millipore water was added to 10 mL of cold ether and the mixture was centrifuged again. The ether was decanted and the aqueous layer, containing the crude peptide was transferred to a round bottom flask for lyophilization. Crude yields for peptide synthesis were usually around 90%.

Peptide Purification:

HPLC purification was performed on an Hewlett Packard-1050 HPLC using a semi-preparative $C_{18}$ column (Vydac) with a flow rate of 3 mL/minute. Analytical HPLC was carried out using a $C_{18}$ column (Vydac) with a flow rate of 1 μL/minute. Gradient elution was used with the following solvent systems: solvent A=0.1% TFA in water, solvent B=80:20 $CH_3CN$/0.1% TFA in water. Peptides were purified by reverse phase semipreparative HPLC with a C18-silica column (5 μm, 10×250 mm; Vydac, Hesperia, Calif.). Purity of peptides was monitored by reverse phase analytical HPLC with a C18-silica column (5 gm, 4×250 μm; Vydac, Hesperia, Calif.). Peptide chromatograms were monitored at 220 nm, which corresponds to the absorption of the amide chromophore. Crude peptides were dissolved in Millipore water at a concentration of 0.2 mg/mL and passed through a 0.45 μm polyvinylidene difluoride syringe filter to remove particulate material. Each injection typically contained a ca. 1.5 mg of peptide. The shape of the chromatograph was analyzed to ensure good resolution and peak shape. The injection volume was typically decreased if poor resolution or separation was noticed. Gradient conditions were adjusted to about 0.5% of $CH_3CN/H_2O$/TFA (80:20:0.01) per minute.

Peptide homogeneity was assured by analytical HPLC using a C18-silica analytical column (5 μm, 4×250 mm; Vydac, Hesperia, Calif.) and $CH_3CN/H_2O$/TFA eluents at a flow rate of 1 mL/min. The peptides were generally μ95% pure, based on analytical HFPLC. Peptide identity was initially confirmed by matrix-assisted laser desorption time-of-flight mass spectroscopy (MALDI-TOF-MS), and subsequently by high resolution $^1$H NMR analysis.

Analytical Methods:

CD Spectroscopy:

A 2 mg/mL stock solution of each peptide in Millipore water (concentration determined by mass of freshly lyophilized peptide) was mixed with aqueous Tris-buffered saline to give aqueous solutions of 0.2 mg/mL peptide in 10 mM Tris, 150 mM NaCl, pH 7.2. The final concentration of the peptides in each aqueous Tris-buffered saline solution was calculated from the UV absorbance of the 2 mg/mL stock solution. The extinction coefficient of each peptide was assumed to be 1420 cm$^{-1}$ M$^{-1}$ at 275 nm, the wavelength of α-tyrosine.[2] All CD spectra were obtained on an AVIV 62A-DS CD spectropolarimeter using 1 nm bandwidth, 1 nm resolution, 10 seconds averaging time, 1 scan per second, 0 second delay, and a path length of 0.1 cm or 1 mm. The temperature of the sample was maintained at 25° C., unless otherwise stated. Data were obtained in both methanol and Tris buffer. Data were obtained at high concentration (typically 1-2 mM) and low concentration 0.1 mM. Scans usually ranged from 260 nm to 190 nm but with a high peptide concentration, the increased in dynode voltage prevented the detection of signal below 200 nm. Baseline spectra were subtracted from the raw data to obtain the real CD spectra. Data were converted to ellipticity (deg cm$^2$ dmol$^{-1}$) according to the equation:

$$[\Theta]=\psi \cdot M_r/100 \cdot l \cdot c$$

where ψ is the CD signal in degrees, $M_r$ is the molecular weight divided by the number of chromophores, l is the pathlength in dm, and c is the concentration in g/mL.

MALDI-TOF Mass Spectroscopy:

Mass spectra of all peptides were obtained using Bruker Reflex II MALDI-TOF Mass Spectrometer with a 337 nm laser. Spectra were resolved to the mass unit of the peptides. MALDI-TOF data were obtained for all UPLC purified samples of the peptides. For MALDI experiments, a matrix of α-cyano-4-hydroxycinnamic acid was used. The instrument was calibrated to a standard mixture of leu$^5$-enkephalin (M+H$^+$=556.28), angiotensin I (M+H$^+$=1296.7) and neurotensin (M+H$^+$=1672.9). The mass of the pure peptides matched the theoretical mass of the peptide within a very narrow margin of error.

Abbreviations Used: EDCl.HCl=N,N-Dimethylaminopropyl-3-ethylcarbodiimide hydrochloride salt, DMF=N,N-Dimethylformamide, TFA=Trifluoroacetic acid, DIEA=Diisopropylethylamine, HOAT=1-Hydroxy-7-azabenzotriazole, HOBt=1-Hydroxybenzotriazole hydrate, HBTU=O-Benzotriazolyl-1-yl-N,N,N',N'-tetramethyluronium hexafluorophosphate, HATU=O-(7-azabenzotriazol-1-yl)-N,N,N',N'-trimethyluronium hexafluorophosphate, TFE=Trifluoroethanol, Boc$_2$O=Di-tert-butyl dicarbonate.

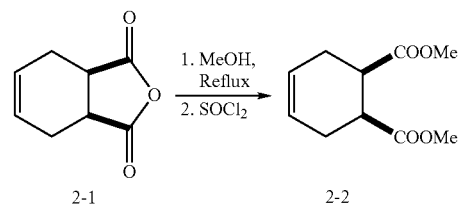

2-1        2-2

(1R, 6S)-Methyl 6-methoxycarbonyl-3-cyclohexenecarboxylate (2-2) was prepared from the phthalic anhydride 2-1 following procedure developed by Appella et al.[3] of the Gellman group. To the anhydride (35.0 g, 230 mmol) was added methanol (200 mL) and the mixture was refluxed for 4.5 hours. The mixture was subsequently cooled to room temperature and then 0° C. in an ice bath followed by drop wise addition of thionyl chloride during a 30 minutes period. The mixture was stirred allowing temperature to rise gradually from 0° C. to room temperature for 8 hours. The reaction mixture was concentrated on a rotary evaporator and dried further under vacuum to obtain 45.1 g (99%) of 2-2 as a pale yellow oil: $R_f$=0.67, 1:1 hexane/ethyl acetate; $^1$H NMR (300 MHz, CDCl$_3$): δ 5.66 (m, 1H, HC=CH), 3.68 (s, 3H, OCH$_3$), 3.04 (m, 1H, C$\underline{H}$COOCH$_3$), 2.60-2.49 (m, 1H, CH$\underline{H}_2$COOCH3), 2.39-2.29 (m, 1H, C$\underline{H}_2$CHCOOCH3); $^{13}$C NMR (75 MHz, CDCl$_3$): δ 177.4 (C), 122.3 (CH), 50.7 (CH$_3$), 39.0 (CH), 24.6 (CH$_2$); MS-ESI m/z 199.2 [M+H]$^+$, 221.2 [M+Na]$^+$, 419.4 [2M+Na]$^+$.

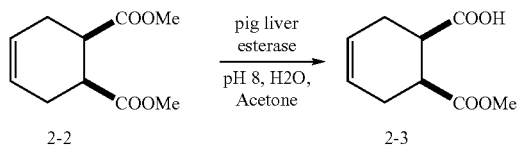

(1R, 6S)-6-Methoxycarbonyl-3-cyclohexene-1-carboxylic acid (2-3) was prepared following the procedure of Ohno and co-workers[4], that had been successfully applied by Appella et al.[3] of the Gellman group. Precaution was taken to make sure all glassware was clean. All glassware was washed in acid bath and rinsed twice with Millipore water. To Millipore water (2.6 L) was added KH$_2$PO$_4$ (61.79 g, 454 mmol) and the pH of the resulting solution adjusted to 8 by adding a prepared solution of 2.5 M NaOH and using a pH meter calibrated at pH 4 and pH 10. The diester 2-2 (45 g, 227 mmol) was dissolved in reagent grade acetone (131 mL) and this solution added to the aqueous KH$_2$PO$_4$ solution. Pig liver esterase (10.5 mL, 48189 units) was added, and the resulting solution was stirred for 24 hours. The reaction was monitored by TLC (1:1 hexane:ethyl acetate, $R_f$ (2-2)=0.67, $R_f$(2-3)= 0.24). After ascertaining that reaction was complete, the enzyme was filtered off through celite in a fritted glass funnel. The resulting solution was then acidified with 1M HCl to a pH about 2 and then extracted three times with ethyl acetate (1200 mL total). The organic extracts were dried over MgSO$_4$, concentrated, and dried under vacuum overnight to afford 38 g (91%) of 2-3 as a thick yellow oil: $^1$H NMR (300 MHz, CDCl$_3$): δ 11.24 (br s, 1H, OH), 5.68 (m, 2H, HC=CH), 3.70 (s, 3H, OCH$_3$), 3.07 (m, 2H, C$\underline{H}$COOCH$_3$ and C$\underline{H}$COOH), 2.62-2.54 (m, 2H, CH$_2$CHCOOCH$_3$ or C H$_2$CHCOOH), 2.41-2.32 (m, 2H, C$\underline{H}_2$CHCOOCH$_3$ or C $\underline{H}_2$CHCOOH); $^{13}$C NMR (75 MHz, CDCl$_3$): δ 179.6 (C), 173.5 (C), 125.0 (CH), 124.8 (CH), 51.7 (CH$_3$), 39.4 (CH), 39.2 (CH), 25.5 (CH$_2$), 25.3 (CH$_2$); MS-ESI m/z 207.1 [M+Na]$^+$.

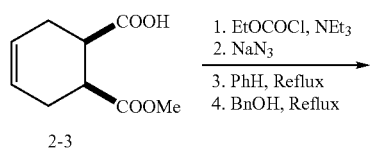

Methyl (1S, 6R)-6-Benzyloxycarbonylaminocyclohex-3-enecarboxylate (2-4) was prepared according to the procedure of Ohno and co-workers[4], that was successfully repeated by Appella et al.[3] of the Gellman group. The monoester 2-3 (7.08 g, 38.4 mmol) was dissolved in acetone (125 mL) and the resulting solution cooled to 0° C. To this solution was added Et$_3$N (7.0 mL, 50.2 mmol), followed by slow addition of ethyl chloroformate (4.77 mL, 49.9 mmol). Mixture was stirred at 0° C. for 15 minutes. In a separate flask, NaN$_3$ (4 g, 61.5 mmol) was dissolved in Millipore water (35 mL), and this solution added to the reaction flask. The temperature was gradually raised to room temperature and stirring continued for 3 hours. The reaction mixture was diluted with water (123 mL) and the resulting solution extracted three times with diethyl ether (900 mL total). The organic extracts were dried over MgSO$_4$, concentrated without heating, and put under vacuum for a few minutes to afford yellow oil. To this oil was added anhydrous benzene (97 mL), and the resulting solution refluxed under a nitrogen atmosphere for 3 hours. The solution was cooled to room temperature followed by the addition of benzyl alcohol (13.9 mL, 133.8 mmol). The resulting solution was refluxed under an atmosphere of nitrogen for 22 hours. A yellow solution containing droplets of another liquid on the bottom of the flask was formed. The solution was cooled to room temperature, and the solvent was then removed on a rotary evaporator to afford 22.1 g (82% yield of 2-4 based on $^1$H NMR) of yellow liquid being a mixture of 2-4 and benzyl alcohol: $^1$H NMR (300 MHz, CDCl$_3$): δ 7.39-7.22 (m, ArH of 2-4 and BnOH), 5.67 (m, 2H, HC=CH), 5.45 (br d, J=9 Hz, 1H, NH), 5.06 (s, 2H, ArC$\underline{H}_2$) 4.64 (s, ArC$\underline{H}_2$ of BnOH), 4.23 (m, 1H, C$\underline{H}$NHCbz), 3.66 (s, 3H, OCH$_3$), 2.80 (m, 1H, C$\underline{H}$COOCH$_3$), 2.57-2.43 (m, 1H), 2.42-2.25 (m, 2H), 2.23-2.10 (m, 1H).

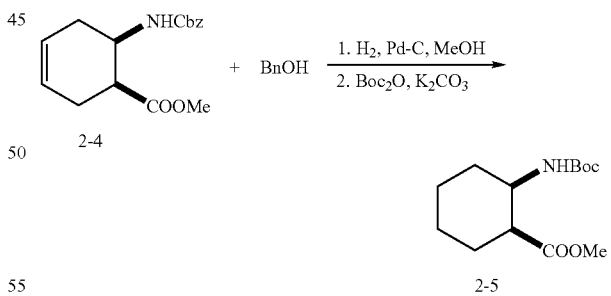

Methyl (1S, 6R)-6-tert-butyloxycarbonylaminocyclohexanecarboxylate (2-5) was prepared by two methods.

Method 1. Methanol (25 mL) was added to a mixture of 2-4 and benzyl alcohol (3.81 g), followed by 10% Pd—C (0.10 g) under nitrogen. The solution was shaken on a Parr apparatus under H$_2$ (50 psi) for 46 hours. The solution was then filtered through a plug of glass wool, concentrated, and dried under vacuum to obtain a yellow liquid. Water (5 mL) was added to the liquid, and then 2 M HCl was added to the solution until a pH of 2 was obtained. The resulting solution was extracted with diethyl ether three times (75 mL total) to remove benzyl alcohol. To the resulting aqueous solution was added 10% $K_2CO_3$ portion wise until a pH of 9 was obtained. Dioxane (10 mL) was added, followed by $Boc_2O$ (1.76 g, 8.1 mmol). The resulting solution was stirred for 33 hours. The solution was then transferred to a separatory funnel, water (10 mL) was added, and the solution extracted three times with ethyl acetate (150 mL total). The combined organic extracts were dried over $MgSO_4$, concentrated, and dried under vacuum overnight to obtain a viscous yellow liquid. The crude product was purified by $SiO_2$ flash column chromatography, eluting with 6:1 hexane:ethyl acetate ($R_f$=0.26) to afford 2-5 as clear oil (2.37 g, 70%).

Method 2. A mixture of 2-4 and benzyl alcohol (4.95 g) was dissolved in methanol (25 mL) and transferred to a hydrogenation flask. This was followed by the addition of 10% Pd—C (0.85 g) and $Boc_2O$ (4.5 g, 20.5 mmol) under $N_2$. The solution was shaken on a Parr apparatus under $H_2$ (50 psi) for 24 hours. The solution was then passed through a plug of silica gel and celite, concentrated, and dried further under vacuum overnight to obtain pale yellow oil. The crude product was purified through a slurry-packed $SiO_2$ column eluting with 4:1 hexane:ethyl acetate ($R_f$=0.41). The product eluted in fractions 8-21 (15 mL fractions collected) to afford 3.5 g (80% yield) of 2-5 as a clear oil: $^1H$ NMR (300 MHz, $CDCl_3$): δ 5.32 (br, 1H, NH), 3.85 (m, 1H, C$\underline{H}$NHBoc), 3.69 (s, 3H, OC$\underline{H}_3$), 2.79 (br q, J=4.5 Hz, 1H, C$\underline{H}$COOC$H_3$), 2.07-1.94 (m, 1H), 1.84-1.55 (m, 4H), 1.51-1.25 (m, 12H), 1.43 (s, $CH_3$); $^{13}C$ NMR (75 MHz, $CDCl_3$): δ 174.2 (C), 155.3 (C), 79.0 (C), 51.5 ($CH_3$), 49.0 (CH), 44.9 ($CH_3$), 29.7 ($CH_2$), 28.2 ($CH_3$), 26.8 ($CH_2$), 23.7 ($CH_2$), 22.5 ($CH_2$); MS-ESI m/z 280.1 $[M+Na]^+$, 537.2 $[2M+Na]^+$.

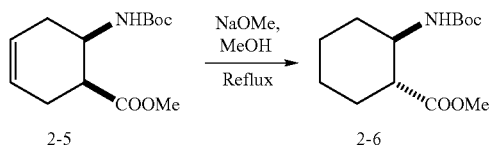

Methyl (1R, 2R)-N-tert-butyloxycarbonyl-trans-2-aminocyclohexanecarboxylate (2-6) was prepared by epimerization of the cis-isomer 2-5. Sodium (0.10 g, 4.34 mmol) was weighed out under hexane, and placed into a flame dried schlenk flask outfitted with a condenser. The flask was placed under vacuum and $N_2$ repeatedly, three times, to dry off hexane. The flask was then cooled to 0° C., and anhydrous methanol (4 mL) was added. The mixture was kept under $N_2$ and vented to remove evolved gases until all the sodium dissolved. In another flame-dried flask containing 2-5 (0.71 g, 2.76 mmol), that had been dried under vacuum overnight, was added anhydrous methanol (8 mL) and the flask was swirled to dissolve the ester. The ester solution 2-5 was then transferred to the Schlenk flask containing NaOMe solution via cannula. The resulting solution was then refluxed for 5 hours. The solution was cooled to room temperature and then 0.5 M $NH_4Cl$ (16 mL) was added. The mixture was stored under $N_2$ overnight and clear needle-like crystals formed during this time. The solvent was mostly removed on a rotary evaporator, and the precipitate collected by suction filtration to obtain white solid after drying under vacuum. The solid was recrystallized from n-heptane to afford 0.44 g (62% yield) of 2-6 as colorless crystals: m.p. 90-91° C.; $^1H$ NMR (300 MHz, $CDCl_3$): δ 4.50 (br, 1H, NH), 3.67 (s and m, 4H, $OCH_3$ and C$\underline{H}$NHBoc), 2.23 (dt, J=11.4, 4.2 Hz, 1H, C$\underline{H}$COOC$H_3$), 2.08-2.00 (m, 1H), 1.95-1.86 (m, 1H), 1.81-1.53 (m, 2H), 1.51-1.29 (m, 11H), 1.42 (s, $CH_3$), 1.26-1.11 (m, 2H); $^{13}C$ NMR (75 MHz, $CDCl_3$): δ 174.3 (C), 154.7 (C), 79.0 (C), 51.5 ($CH_3$), 51.0 (CH), 50.0 (CH), 32.8 ($CH_2$), 28.3 ($CH_2$), 28.1 ($CH_3$), 24.5 ($CH_2$), 24.2 ($CH_2$); MS-ESI m/z 280.1 $[M+Na]^+$, 537.2 $[2M+Na]^+$.

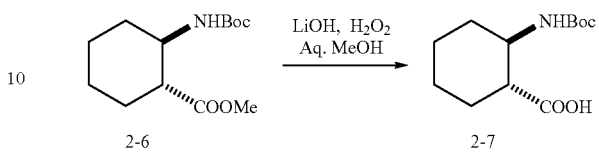

(1R, 2R)-N-tert-butyloxycarbonyl-trans-2-aminocyclohexanecarboxylic acid (2-7) was prepared from the corresponding ester by hydrolysis. Methanol (80 mL) and water (26 mL) were added to 2-6 (1.35 g, 5.25 mmol), followed by $LiOH \cdot H_2O$ (2.64 g, 62.9 mmol) and 30% aqueous $H_2O_2$ (3.72 mL, 29 mmol). The mixture was stirred at room temperature for 50 hours. A solution of $Na_2SO_3$ (8.78 g, 69.7 mmol) in water (52 mL) was then added at 0° C., and the mixture stirred for 25 minutes. The methanol was removed on a rotary evaporator leaving a clear solution. The solution was cooled to 0° C. again followed by addition of 2M HCl until white precipitate formed which did not dissolve on swirling. The mixture was treated with ethyl acetate which caused the white precipitate to dissolve. The aqueous layer was isolated and the pH measured (pH=1). The aqueous layer was extracted with the original ethyl acetate layer once and then four times with fresh portions of ethyl acetate. The combined organic extracts were dried over $MgSO_4$, concentrated on a rotary evaporator and dried further under vacuum to obtain 1.23 g (97% yield) of 2-7 as a shiny white solid that looked pure by NMR. A sample of this white solid was recrystallized in ethyl acetate/hexane but there wasn't any marked improvement in purity: m.p. 154-155° C.; $^1H$ NMR (300 MHz, $CDCl_3$): δ 11.64 (br, 1H, COOH), 4.65 (br, 1H, NH), 3.65 (br m, 1H), 2.25 (td, J=11.4, 3.6 Hz, HOOCC$\underline{H}$), 2.08-1.95 (m, 2H), 1.75-1.14 (m, 6H), 1.43 (s, 9H, $CH_3$); $^{13}C$ NMR (75 MHz, $CDCl_3$): δ 179.0 (C), 154.9 (C), 79.2 (C), 50.9 (CH), 49.5 (CH), 32.6 (CH2), 28.4 (CH2), 28.1 (CH3), 24.4 (CH2), 24.2 (CH2); MS-ESI m/z 266.1 [M+Na], 509.2 $[2M+Na]^+$.

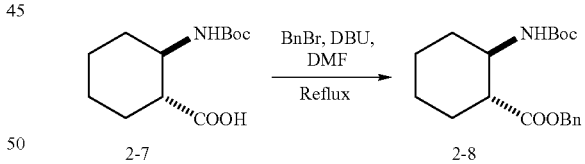

Benzyl (1R, 2R)-N-tert-butyloxycarbonyl-trans-2-aminocyclohexanecarboxylate (2-8) was prepared from the corresponding free acid by benzylation. The acid 2-7 (0.2 g, 0.82 mmol) was dissolved in dry benzene. Benzyl bromide (0.1 mL, 0.82 mmol) was added followed by 1,8-diazabicyclo[5 4 0]unde-7-ene (0.12 mL, 0.82 mmol) and the solution refluxed under $N_2$ for 24 hours. White solid precipitated from the solution in the course of the reaction. The mixture was cooled to room temperature and concentrated to obtain a tan solid. The crude product was purified by $SiO_2$ flash column chromatography eluting with 6:1 hexane:ethyl acetate ($R_f$=0.24). The product eluted in fractions 14-30 (10 mL fractions collected) to afford 0.25 g (90% yield) of 2-8 as a white solid. A sample of this solid was recrystallized from n-heptane: m.p. 103-104° C.; $^1H$ NMR (300 MHz, CDCl3): δ 7.38-7.29 (m, 5H, ArH), 5.12 (s, 2H, ArCH₂), 4.52 (br, 1H, NH), 3.69 (br td, J=10.4, 9 Hz, 1H, BocHNCH), 2.31 (td, J=11.7,3.6 Hz, 1H, BnOCOCH), 2.10-2.05 (m, 1H), 1.98-1.90 (m, 1H), 1.79-1.56 (m, 3H), 1.39 (s, 9H, CH₃), 1.36 (m, 1H), 1.27-1.11 (m, 2H); $^{13}$C NMR (75 MHz, CDCl₃): δ 173.8 (C), 154.8 (C), 136.0 (C), 128.6 (CH), 128.0 (CH), 79.3 (C), 66.2 (CH₂), 51.3 (CH), 50.0 (CH), 33.0 (CH₂), 28.6 (CH₂), 28.3 (CH₃), 24.6 (CH₂), 24.4 (CH₂); MS-ESI m/z 356.1 [M+Na]⁺, 689.3 [2M+Na]⁺.

(1R, 2R)-2-(9H-Fluoren-9-ylmethoxycarbonylamino)-cyclohexanecarboxylic acid (2-9) was prepared from the corresponding Boc-protected free acid by two methods.

Method 1.

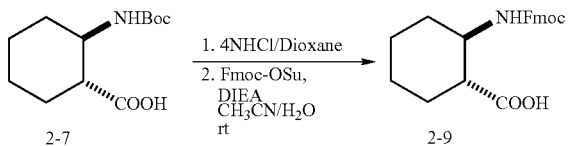

Boc-protected acid (1.39 g, 5.72 mmol) was dissolved in 4N HCl/dioxane (10 mL) and the mixture stirred at room temperature for 4 hours. Progress of reaction was checked by TLC in CH₂Cl₂:MeOH (10:1). Solvent was removed under a stream of nitrogen and resulting white solid dried under vacuum for 5 hours. The free amine was dissolved in CH₃CN/H₂O (4:1, 69 ml), followed by addition of DIEA and Fmoc-OSu. The reaction mixture was then stirred at room temperature for 3.5 hours. Progress of reaction was monitored by TLC in hexane/ethyl acetate (1:1). The reaction mixture was cooled to 0° C. and 1M HCl (approximately 10 mL) added to adjust pH to approximately 7. CH₃CN was removed on a rotary evaporator leaving a white precipitate. Additional 1M HCl was added at 0° C. until more white precipitate formed. Collected white solid by suction filtration and washed with dilute aqueous HCl. Dissolved white solid in large excess of ethyl acetate and filtered to separate undissolved impurities. Filtrate was washed once with 1M HCl and once with brine. Organic extracts were dried in MgSO₄ and concentrated on a rotary evaporator at room temperature to obtain bright white solid which was further dried under vacuum. TLC of white solid in CH₂Cl₂/MeOH (9:1) showed a single spot of R$_f$=0.40. The crude product was purified by crystallization from n-hexane/ethyl acetate to afford 1.68 g (83%) of the Fmoc-protected ACHC as a white solid: mp 207-208° C.; [α]$^{23}$$_D$=−37.8 (c 0.50, acetone); R$_f$=0.43, 10:1 CH₂Cl₂/MeOH; $^1$H NMR (300 MHz, CDCl₃/CD₃OD) δ 7.77 (d, J=7.3 Hz, 2H, ArH), 7.62 (d, J=7.0 Hz, 2H, ArH), 7.42-7.29 (m, 4H, ArH), 4.33-4.19 (m, 3H), 3.73-3.67 (m, 1H), 2.35-2.28 (m, 1H), 2.02-1.98 (m, 2H), 1.78-1.73 (m, 2H), 1.63-1.51 (m, 1H), 1.41-1.22 (m, 3H); $^{13}$C NMR (75 MHz, CDCl₃/CD₃OD) δ 180.61 (C), 160.16 (C), 147.69 (C), 147.53 (C), 144.92 (C), 131.26 (CH), 130.67 (CH), 128.69 (CH), 123.47 (CH), 70.23 (CH₂), 55.12 (CH), 52.45 (CH), 50.84 (CH), 36.27 (CH₂), 32.73 (CH₂), 28.35 (CH₂), 28.11 (CH₂); MS-ESI m/z 388.1 [M+Na]⁺, 753.2 [2M+Na]⁺.

Method 2.

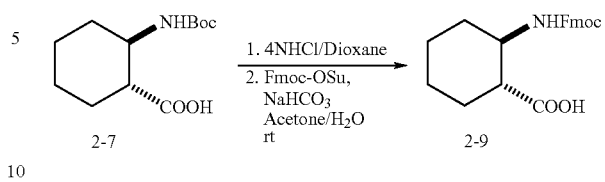

Boc-protected acid (0.63 g, 2.59 mmol) was dissolved in 4N HCl/dioxane (10 mL) and the mixture stirred at room temperature for 4 hours. Progress of reaction was checked by TLC in CH₂Cl₂:MeOH (10:1). Solvent was removed under a stream of nitrogen and resulting white solid dried under vacuum for 2 hours. This solid was dissolved in acetone/H₂O (2:1, 81 mL), cooled to 0° C. and Fmoc-OSu (1.04 g, 3.08 mmol) and NaHCO₃ (1.99 g, 23.7 mmol) were added. The turbid reaction mixture was stirred at 0° C. for 1 hour and was then allowed to stir at room temperature overnight. The acetone was removed under reduced pressure. The aqueous residue was diluted with H₂O (27 mL), stirred for 1 hour at room temperature with diethyl ether (109 mL), and the layers were separated. Separation by extraction was not possible because the bottom layer contained white solid which could not easily come off a separatory funnel. The solid was isolated by suction filtration and washed subsequently with NaHCO₃, 1N HCl and water. The solid was diluted with HCl and a large volume of ethyl acetate used for extraction. The combined ethyl acetate layers were dried in MgSO4, concentrated on a rotary evaporator, and dried under vacuum to obtain a white solid. The crude product was purified by crystallization from n-hexane/ethyl acetate to afford 0.68 g (72%) of 2-9 as a white solid: mp 206-207° C.; [α]$^{23}$$_D$=−37.6 (c 0.50, acetone); R$_f$=0.45, 10:1 CH₂Cl₂/MeOH;

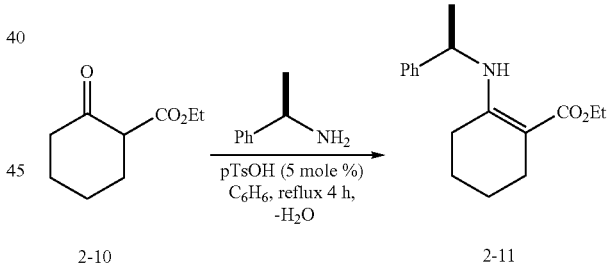

Compound 2-11. To a solution of ketoester 2-10 (11.0 g, 64.7 mmol) in 100 mL of dry benzene was added the chiral amine (R)-(+)-α-methylbenzylamine (8.01 g, 66.1 mmol), and a catalytic amount of p-toluenesulfonic acid (0.618 g, 3.25 mmol, 5 mole %). The mixture was refluxed under N₂ with continuous removal of water using a Dean-Stark trap within 4 hours. After the solution was cooled to room temperature, it was washed twice with saturated aqueous NaHCO₃. The organic extracts were dried over MgSO₄, concentrated, and dried under vacuum to obtain a yellow oily residue. The resulting yellow oily residue was fractionally distilled to give 15.8 g (89%) of 2-11 as a pale yellow oil: bp 160-165, 2 mm Hg; R$_f$=0.32, 20:1 hexane/ethyl acetate; $^1$H NMR (300 MHz, CDCl₃) δ 9.40 (d, J=7.5 Hz, 1H, NH), 7.35-7.20 (m, 5H, ArH), 4.63 (quint, J=7.2 Hz, 1H), 4.17 (dq, J=7.2, 1.2 Hz, 2H), 2.36-2.24 (m, 3H), 1.99-1.89 (m, 1H), 1.54-1.47 (m, 7H), 1.30 (t, J=7.2 Hz, 3H); $^{13}$C NMR (75

MHz, CDCl₃) δ 170.74 (C), 158.86 (C), 145.65 (C), 128.47 (CH), 126.58 (CH), 125.23 (CH), 90.34 (C), 58.50 (CH$_2$), 51.79 (CH), 26.43 (CH$_2$), 25.16 (CH$_3$), 23.60 (CH$_2$), 22.40 (CH$_2$), 22.22 (CH$_2$), 14.48 (CH$_3$); MS-ESI m/z 274.2 [M+H]$^+$, 296.1 [M+Na]$^+$, 569.3 [2M+Na]$^+$.

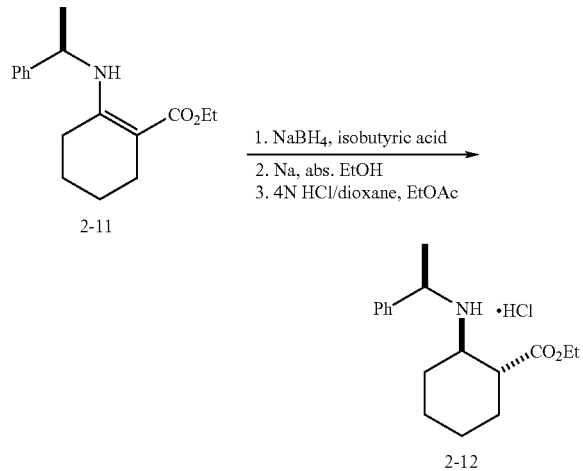

Compound 2-12. Sodium borohydride (3.14 g, 83.0 mmol) was added to isobutyric acid (44 mL, 474.0 mmol) portion wise under N$_2$ at 0° C. This mixture was stirred at room temperature for 30 minutes and then cooled to 0° C. A solution of 2-11 (6.48 g, 23.7 mmol) dissolved in dry toluene (26.4 mL) was added drop wise under N$_2$ at 0° C. The mixture was stirred at 0° C. for 6 hours, followed by addition of a second portion of sodium borohydride (0.20 g, 5.29 mmol). The reaction mixture was then stirred at 0° C. overnight. The reaction mixture was quenched by addition of aqueous solution of 1N HCl to obtain a pH of approximately 1. The mixture was further basified to a pH of about 10 using an aqueous solution of 1 N NaOH followed by extraction with four equal portions of CH$_2$Cl$_2$ (100 ml each). The combined organic extracts were dried over MgSO$_4$ and concentrated under reduced pressure. The resulting oil was applied to a plug of silica gel and washed with 1:1 hexane/ethyl acetate. The filtrate was concentrated to obtain a pale yellow oil (6.01 g, 92%; R$_f$=0.22, 4:1 hexane/ethyl acetate). The resultant oil was dried under vacuum overnight. To this oil (dried under vacuum, 3.11 g, 11.29 mmol), was added freshly distilled ethanol (50 mL) under N$_2$. In a separate flame-dried Schlenk flask outfitted with a condenser was placed sodium (1.3 g, 56.52 mmol). The flask was cooled to 0° C., and dry ethanol (100 mL) was added. The mixture was kept under N$_2$ and vented to remove evolved gases until all of the sodium dissolved. The clear solution of the carboxylate was then transferred to the NaOEt solution via cannula. The resulting solution was refluxed at 80° C. under N$_2$ for 15 h. The solvent was removed on a rotary evaporator followed by addition of brine (100 mL). The resulting mixture was basified to a pH of approximately 10 by addition of aqueous 1 N NaOH and then extracted four times with ethyl acetate (100 mL each). The combined organic extracts were dried over MgSO$_4$ and concentrated under reduced pressure. The resulting oil was applied to a plug of silica gel and washed with 3:1 hexane/ethyl acetate. The filtrate was then concentrated to obtain pale yellow oil (2.62 g, 84%). To this oil was added ethyl acetate (19 ml), followed by drop wise addition of 4 N HCl in dioxane (2.8 mL, 11.2 mmol) at room temperature. The resulting solution was cooled to 0° C. and allowed to stand at 0° C. overnight. A white precipitate was formed during this time. The white solid was filtered and washed three times with 20 ml portions of cold ethyl acetate to afford the desired crude material in 84% yield from 2-11. This crude product was purified by recrystallization from acetonitrile. The solid was suspended in acetonitrile (36 ml) and heated to reflux for 1 h. The mixture was filtered through cotton wool and cooled to 0° C. over night. The resulting precipitate was isolated by filtration and washed three times with 10 ml portions of cold acetonitrile. The mother liquor and washings were combined and condensed to about half the original volume to get a second crop. The combined crops were dried under vacuum to give 1.28 g of 2-12 as a white crystalline solid (51% yield). $^1$H NMR of the corresponding free amine 2-13 indicated the diastereomeric excess to be μ99%: mp 210-211° C.; R$_f$=0.39, 4:1 hexane/ethyl acetate; $^1$H NMR (300 MHz, CDCl$_3$) δ 9.97 (br s, 1H, NH$_2$), 9.70 (br s, 1H, NH$_2$), 7.84-7.80 (m, 2H, ArH), 7.47-7.30 (m, 3H, ArH), 4.64-4.60 (m, 1H), 4.34-4.23 (m, 2H), 3.15-3.12 (m, 2H), 2.21-2.17 (m, 1H), 1.96-1.59 (m, 8H), 1.36-1.20 (m, 5H), 0.97-0.93 (m, 1H); $^{13}$C NMR (75 MHz, CDCl$_3$) δ 174.14 (C), 136.62 (C), 128.93 (CH), 128.84 (CH), 128.40 (CH), 61.14 (CH$_2$), 59.39 (CH), 56.49 (CH), 45.85 (CH$_3$), 29.92 (CH$_2$), 29.26 (CH$_2$), 23.92 (CH$_2$), 23.72 (CH$_2$), 20.47 (CH), 13.94 (CH$_3$); MS-ESI m/z 276.2 [(M−HCl)+H]$^+$, 298.2 [(M−HCl)+Na]$^+$, 573.3 [2(M−HCl)+Na]$^+$.

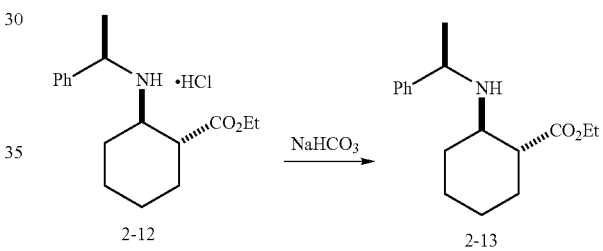

Compound 2-13. A small sample of 2-12 was mixed with an excess of saturated NaHCO$_3$ solution and then extracted into diethyl ether. After drying over MgSO$_4$, the organic extract was concentrated under reduced pressure to give 2-13 as a clear oil: R$_f$=0.40, 4:1 hexane/ethyl acetate; $^1$H NMR (300 Mz, CDCl$_3$) δ 7.30-7.21 (m, 5H, ArH), 4.24-4.13 (m, 2H, CH$_3$CH$_2$OCO), 3.82 (q, J=6.6 Hz, 1H, ArCHNH), 2.72 (td, J=10.7, 3.8 Hz, 1H, HNCHCH$_2$), 2.19-2.10 (m, 1H, OCOCH), 1.91-1.82 (m, 2H), 1.68-1.63 (m, 2H), 1.32-1.11 (m, 10H); $^{13}$C NMR (75 MHz, CDCl$_3$) δ 175.50 (C), 146.86 (C), 128.0 (CH), 126.42 (CH), 126.20 (CH), 59.86 (CH$_2$), 55.88 (CH), 55.44 (CH), 51.58 (CH), 32.99 (CH$_2$), 30.03 (CH$_2$), 28.95 (CH$_2$), 24.72 (CH$_2$), 23.64 (CH$_3$), 14.06 (CH$_3$); MS-ESI m/z 276.2 [M+H]$^+$, 298.2 [M+Na]$^+$, 573.4 [2M+Na]$^+$.

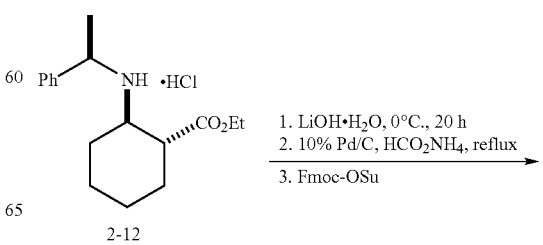

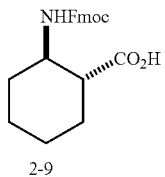

2-9

Compound 2-9 (Fmoc-ACHC). Compound 2-12 (1.23 g, 3.94 mmol) was dissolved in TBF/MeOH/H20 (2:1:1, 44 mL), and the solution was cooled to 0° C. LiOH.H2O (0.83 g, 19.8 mmol) dissolved in 4.5 mL H$_2$O was added. The mixture was stirred at 0° C. for 20 hours. The solvent was removed under reduced pressure and the residue was applied to a plug of silica gel and washed with CH$_2$Cl$_2$/MeOH 6:1. The filtrate was concentrated to obtain a white solid (R$_f$ 0.26, 8:1 CH$_2$Cl$_2$MeOH). To a clear solution of this white solid in 88 mL MeOH, Pd/C (10%, 0.92 g) and ammonium formate (1.24 g, 19.7 mmol) were added under N$_2$ at room temperature. The mixture was refluxed for 4 hours. After the reaction was complete (disappearance of starting material, as monitored by TLC), the cool reaction mixture was filtered through celite, and the filtrate concentrated to obtain a white solid. This solid was dissolved in acetone/H$_2$O (2:1, 45 mL), cooled to 0° C. and Fmoc-OSu (1.29 g, 3.82 mmol) and NaHCO$_3$ (3.31 g, 39.4 mmol) were added. The turbid reaction mixture was stirred at 0° C. for 1 hour and was then allowed to stir at room temperature overnight. The acetone was removed under reduced pressure. The aqueous residue was diluted with H$_2$O (45 mL), stirred for 1 hour at room temperature with diethyl ether (200 mL), and the layers were separated. The ether phase was washed three times with saturated NaHCO$_3$ (100 mL each). The combined aqueous phase was acidified with 1 N aqueous HCl and extracted three times with ethyl acetate (100 mL each). The organic extracts were dried over MgSO4 and concentrated to give a white solid. The crude product was purified by crystallization from n-hexane/chloroform to afford 1.09 g (76%) of 2-9 as a white solid: mp 205-206° C.; [α]$^{23}_D$=–37.6 (c 0.50, acetone); R$_f$=0.43, 10:1 CH$_2$Cl$_2$/MeOH; $^1$H NMR (300 MHz, CDCl$_3$/CD$_3$OD) δ 7.77 (d, J=7.3 Hz, 2H), 7.62 (d, J=7.0 Hz, 2H), 7.42-7.29 (m, 4H), 4.33-4.19 (m, 3H), 3.73-3.67 (m, 1H), 2.35-2.28 (m, 1H), 2.02-1.98 (m, 2H), 1.78-1.73 (m, 2H), 1.63-1.51 (m, 1H), 1.41-1.22 (m, 3H; $^{13}$C NMR (75 MHz, CDCl$_3$/CD$_3$OD) δ 180.61 (C), 160.16 (C), 147.69 (C), 147.53 (C), 144.92 (C), 131.26 (CH), 130.67 (CH), 128.69 (CH), 123.47 (CH), 70.23 (CH$_2$), 55.12 (CH), 52.45 (CH), 50.84 (CH), 36.27 (CH$_2$), 32.73 (CH$_2$), 28.35 (CH$_2$), 28.11 (CH$_2$); MS-ESI m/z 364.2 [M–H]$^-$, 753.2 [2M–H]$^-$.

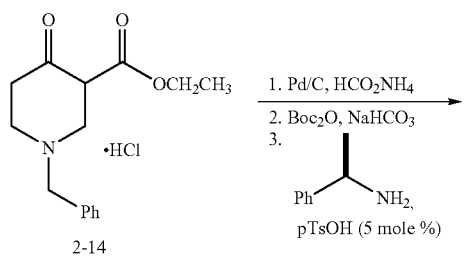

2-14

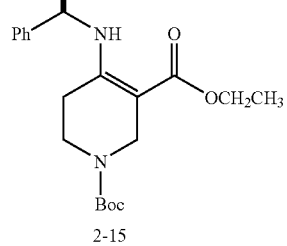

2-15

Pip-Enamine (2-15). The piperidine carboxylate salt 2-14 (15.3 g, 50.5 mmol) was dissolved in absolute ethanol (480 mL) and ammonium formate (15.7 g, 249 mmol) added. The mixture was then flushed with N$_2$ continuously while adding Pd/C (10%, 2.40 g). The mixture was refluxed for 2 hours. The reaction mixture was cooled to room temperature, filtered through celite and through a syringe filter. The filtrate was concentrated on a rotary evaporator and dried under vacuum to afford 10.03 g (96% yield) of a yellowish-white solid. The amine salt was dissolved in chloroform (85 mL) and sonicated followed by addition of a solution of NaHCO$_3$ (4.17 g, 49.6 mmol) in water (80 mL) and NaCl (8.33 g, 143 mmol). A solution of Boc$_2$O (10.4 g, 47.5 mmol) dissolved in chloroform (30 mL) was slowly added during a 15 minutes period and the mixture refluxed for 15 hours. The organic layer was separated and the aqueous layer extracted three times with chloroform (150 mL total volume). The organic extracts were dried over MgSO$_4$, concentrated and dried under vacuum to obtain reddish-yellow oil (13.2 g, 95%). The oil was dissolved in dry benzene (150 mL) followed by addition of a catalytic amount of p-toluenesulfonic acid (451 mg, 2.37 mmol, 5 mole %), and the chiral amine (R)-(+)-α-methylbenzylamine (6.44 mL, 49.9 mmol). The mixture was refluxed under N$_2$ with continuous removal of water using a Dean-Stark trap during 12 hours. The reaction mixture was cooled and then washed twice with saturated aqueous NaHCO$_3$ (150 mL). The organic extract was dried over anhydrous MgSO$_4$ and concentrated on a rotary evaporator. The resulting yellow oily residue was filtered through a pad of silica gel and washed with CH$_2$Cl$_2$ until filtrate was colorless. The filtrate was concentrated to obtain yellow oil. The crude product was purified by SiO$_2$ flash column chromatography eluting with hexane:ethyl acetate 4:1 (R$_f$=0.44) to afford 13.12 g (72%) of 2-15 as a pale yellow oil: $^1$H NMR (300 MHz, CDCl$_3$) δ 9.27 (d, J=7.2 Hz, 1H, NH), 7.36-7.21 (m, 5H, ArH), 4.61 (quint, J=6.9 Hz, 1H, ArCHNH), 4.18 (q, J=7.0 Hz, 2H, CH$_3$CH$_2$OCO), 4.08 (s, 2H, CCH$_2$NBoc), 3.45-3.39 (m, 1H, CH$_2$CH$_2$NBoc), 3.35-3.28 (m, 1H, CH$_2$CH$_2$NBoc), 2.42-2.36 (m, 1H, NHCCH$_2$), 2.07-2.02 (m, 1H, NHCCH$_2$), 1.53 (d, J=6.9 Hz, 3H, ArCHCH$_3$), 1.44 (s, 9H), 1.29 (t, J=7.0 Hz, 3H, OCOCH$_2$CH$_3$); $^{13}$C NMR (75 MHz, CDCl$_3$) δ 168.78 (C), 156.89 (C), 154.35 (C), 145.00 (C), 128.45 (CH), 126.85 (CH), 125.38 (CH), 88.33 (C), 79.38 (C), 58.75 (CH$_2$), 52.02 (CH), 41.17 (CH$_2$), 39.40 (CH$_2$), 28.17 (CH$_3$), 26.02 (CH$_2$), 24.99 (CH$_3$), 14.34 (CH$_3$); MS-ESI m/z 375.2 [M+H]$^+$, 397.2 [M+Na]$^+$, 771.3 [2M+Na]$^+$.

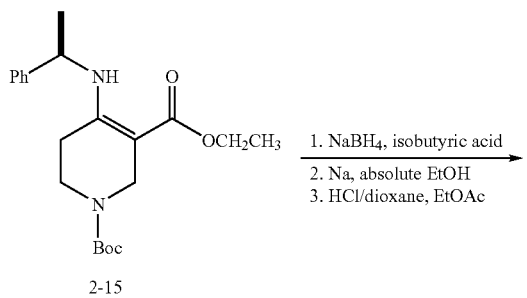

2-15

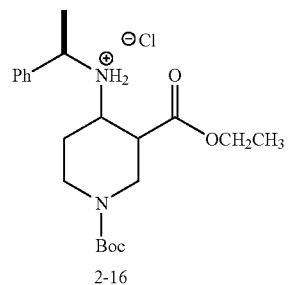

2-16

Pip-Hydrochloride salt (2-16). To isobutyric acid (27.1 mL, 291.7 mmol) in an oven-dried round bottom flask was added sodium borohydride (1.62 g, 42.8 mmol) portion wise under $N_2$ at 0° C. The mixture was stirred at room temperature for 30 minutes followed by the addition of 5 mL of freshly distilled toluene and the mixture cooled to 0° C. again. A solution of the enamine 2-15 (5.32 g, 14.2 mmol) in dry toluene (13 mL) was added drop wise under $N_2$ at 0° C. The mixture was stirred at 0° C. for 2 hours followed by the addition of more sodium borohydride (0.12 g, 3.17 mmol). After 8 hours, the reaction was incomplete as judged by TLC and so more sodium borohydride (0.12 g, 3.17 mmol) was added and mixture stirred overnight. Upon completion of the reaction (24 h), 50 mL of water was added and the mixture stirred at room temperature for 10 minutes. The mixture was then basified to a pH of 10 with 1N NaOH and extracted three times with ethyl acetate (300 mL total volume). The organic extracts were dried over $MgSO_4$ and concentrated under reduced pressure. The resulting yellow oil was dried under vacuum and then applied to a plug of silica gel washing with 2:1 hexane:ethyl acetate. The filtrate was concentrated to obtain pale yellow oil. The crude product was purified by $SiO_2$ flash column chromatography eluting with 2:1 hexane:ethyl acetate ($R_f$=0.38). The product eluted in fractions 10-18 (50 mL fractions collected) to afford 4.126 g (77% yield) of colorless oil. The oil (3.997 g, 10.6 mmol, dried over vacuum overnight) was dissolved in freshly distilled dry ethanol (36 mL). In a flame-dried Schlenk flask was added freshly distilled dry ethanol (70 mL), and sodium (0.73 g, 31.8 mmol) and the mixture was stirred under $N_2$ while venting to remove evolved gases until the sodium completely dissolved. The solution of carboxylate was then transferred to the NaOEt solution and the mixture was stirred at 50° C. under $N_2$ for 21 hours. The mixture was concentrated under reduced pressure followed by the addition of NaCl and 1N NaOH to obtain a pH of 10. The mixture was then extracted three times with ethyl acetate (300 mL total volume). The combined organic extracts were dried over $MgSO_4$ and concentrated on a rotary evaporator. The resulting oil was applied to a plug of silica gel and washed with 2:1 hexane:ethyl acetate. The filtrate was concentrated and dried under vacuum to obtain pale yellow oil (2.943 g, 74% yield from the carboxylate). The oil was then dissolved in ethyl acetate (31.05 mL), and 4 N HCl in dioxane (1.92 mL) was added drop wise while swirling at room temperature. The resulting solution was cooled to 0° C. and allowed to stand at this temperature overnight during which a white precipitate formed. The white solid was filtered and washed three times with cold ethyl acetate to provide the crude material. The crude product was purified by recrystallization from acetonitrile. The solid was suspended in acetonitrile (40 mL) and heated under reflux for 1 hour. The mixture was then filtered through glass wool and cooled to 0° C. overnight. The resulting white crystalline solid was isolated by filtration, and washed three times with fresh portions of cold acetonitrile. The mother liquor and washings were combined and condensed to get a second and third crop. The combined crops were dried under vacuum to afford 1.29 g (22% yield from 2-15) of 2-16 as a white crystalline solid: m.p. 197-199° C.; $R_f$=0.37, 4:1 hexane:ethyl acetate; $^1$H NMR (300 MHz, $CDCl_3$) δ 10.24 (br s, 1H, $NH_2$), 9.89 (br s, 1H, $NH_2$), 7.81-7.78 (m, 2H, ArH), 7.48-7.40 (m, 3H, ArH), 4.60 (br s, 1H, ArCHNH), 4.28 (q, J=6.9 Hz, 2H, $CH_3C$$H_2OCO$), 3.88 (br d, J=13.2 Hz, 1H, $CH_2C$HNH$_2$), 3.26-3.20 (m, 2H, CHCH$_2$NBoc), 3.00-2.78 (m, 1H, OCOCH), 2.55 (br s, 1H,), 2.06-1.93 (m, 4H), 1.74-1.60 (m, 1H), 1.44-1.30 (m, 13H); $^{13}$C NMR (75 MHz, $CDCl_3$) δ 170.75 (C), 158.89 (C), 145.65 (C), 128.47 (CH), 126.59 (CH), 125.22 (CH), 90.33 (C), 58.50 ($CH_2$), 51.78 (CH), 46.44 ($CH_2$), 25.18 ($CH_3$), 23.61 ($CH_2$), 22.39($CH_2$), 22.00 ($CH_2$), 14.49 ($CH_3$); MS-ESI m/z 377.1 $[M-HCl+H]^+$, 753.3 $[2(M-HCl)+H]^+$.

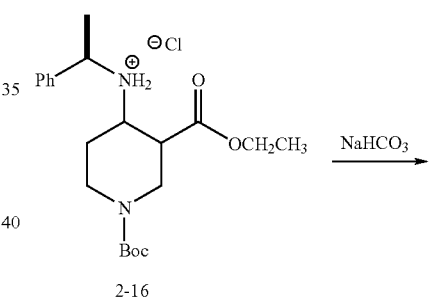

2-16

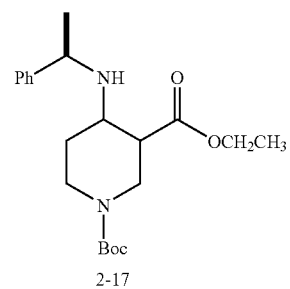

2-17

Pip-Methyl benzylamine ester (2-17). A sample of the carboxylate salt 2-16 was mixed with excess saturated $NaHCO_3$ solution and the mixture was extracted with diethyl ether. The extracts were dried over MgSO4, concentrated under reduced pressure and dried under vacuum to afford 2-17 as clear oil ($R_f$=0.31, hexane:ethyl acetate 3:1). The diastereomeric excess was shown to be μ99%: $^1$H NMR (300 MHz, $CDCl_3$) δ 7.33-7.19 (m, 5H, ArH), 4.24-4.13 (m, 3H), 3.95 (br, 1H), 3.81 (q, J=6.6 Hz, 1H), 2.88 (td, J=10.6, 4.2 Hz, 2H), 2.66 (td, J=12.9, 2.4 Hz, 1H), 2.29 (td, J=10.8, 4.2 Hz, 1H), 1.76-1.72 (m, 1H), 1.43 (s, 1H), 1.33-1.27 (m, 7H), 1.16-1.04 (m, 1H); $^{13}$C NMR (75 MHz, $CDCl_3$) δ 172.89 (C), 154.22 (C), 146.45

(C), 128.19 (CH), 126.71 (CH), 126.24 (CH), 79.63 (C), 60.46 (CH$_2$), 55.77 (CH), 55.19 (CH), 49.66 (CH), 44.91 (CH$_2$), 42.48 (CH$_2$), 32.00 (CH$_2$), 28.16(CH$_3$), 23.91 (CH$_3$), 14.08 (CH$_3$); MS-ESI m/z 377.2 [M+H]$^+$, 399.2 [M+Na]$^+$, 753.4 [2M+H]$^+$, 775.4 [2M+Na]$^+$.

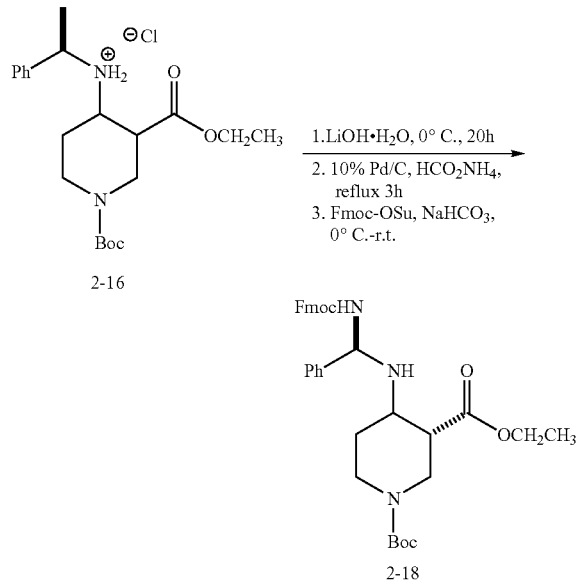

Fmoc-Pip (2-18). The carboxylate salt 2-16 (0.084 g, 0.204 mmol) was dissolved in THF/MeOH/H$_2$O (6:3:1, 9 mL) and the solution cooled to 0° C. LiOH.H$_2$O (0.045 g, 1.07 mmol) dissolved in 0.4 mL H$_2$O was added. The mixture was stirred at 0° C. for 20 hours. The solvent was removed under reduced pressure to give a white solid (R$_f$=0.31, CH$_2$Cl$_2$:MeOH 10:1). The white solid was dissolved in MeOH followed by addition of ammonium formate (0.106 g, 1.68 mmol) and Pd/C (10%, 0.049 g) under N$_2$. The mixture was refluxed for 3 hours. The solution was then cooled, filtered through celite and syringe filter and the filtrate concentrated on a rotary evaporator to afford a white solid. The solid was dissolved in acetone/H$_2$O (2:1, 9 mL) and cooled to 0° C., followed by the addition of Fmoc-OSu (0.067 g, 0.199 mmol) and NaHCO$_3$ (0.16 g, 1.90 mmol). The turbid reaction mixture was stirred at 0° C. for 1 hour and was then allowed to stir at room temperature overnight. Acetone was mostly removed under reduced pressure. The aqueous residue was diluted with H$_2$O (2 mL), diethyl ether (9 mL) added and the mixture stirred at room temperature for 1 hour. The layers were separated and the ether layer was washed three times with saturated NaHCO$_3$. The aqueous phases were combined, acidified with 1N HCl and extracted three times with ethyl acetate (75 mL total volume). The combined organic extracts were dried over MgSO$_4$, concentrated on a rotary evaporator, and dried under vacuum to afford a white solid. The crude product was purified by three crystallizations from n-hexane/chloroform to afford 0.05 g (53% yield) of 2-18 as white fluffy crystals: m.p. 206-208° C.; R$_f$=0.44, 10:1 CH$_2$Cl$_2$:MeOH; [α]$^{23}_D$=−36.0 (c 0.50, acetone); $^1$H NMR (300 MHz, CDCl$_3$/CD$_3$OD) δ 7.77 (d, J=7.5 Hz, 2H, ArH), 7.62 (d, J=6.9 Hz, 2H, ArH), 7.43-7.29 (m, 4H, ArH), 4.36-4.22 (m, 3H), 4.07-4.02 (m, 1H), 3.93-3.86 (m, 2H), 3.09-2.82 (m, 2H), 2.44-2.38 (m, 1H), 2.02-1.97 (m, 1H), 1.50-1.43 (m, 1H), 1.47 (s, 9H); $^{13}$C NMR (75 MHz, CDCl$_3$/CD$_3$OD) δ 173.38 (C), 155.83 (C), 154.21 (C), 143.23 (C), 140.69 (C), 127.07 (CH), 126.46 (CH), 124.42 (CH), 119.27 (CH), 80.00 (C), 66.35 (CH$_2$), 49.73 (CH), 47.77 (CH), 46.57 (CH), 44.33 (CH$_2$), 41.68 (CH$_2$), 30.63 (CH$_2$), 27.51 (CH$_3$); MS-ESI m/z 243.1 [M−Fmoc]$^−$, 465.1 [M−H]$^−$, 931.2 [2M−H]$^−$.

Boc-D-Ala-ACHC-OBn (2-19). In an oven-dried round bottom flask, Boc-ACHC-OBn (0.25 g, 0.75 mmol) was dissolved in 5 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 6 mL of anhydrous DMF and cooled to 0° C. After stirring for 5 minutes, HOBt (0.22 g, 1.63 mmol), EDCl.HCl (0.31 g, 1.63 mmol), DIEA (0.15 mL, 0.86 mmol), and a solution of Boc-D-Ala-OH (0.14 g, 0.75 mmol) in 4 mL of anhydrous DMF were added. The mixture was allowed to warm to room temperature and stirred for 48 hours under N$_2$. The mixture was diluted with 20 mL CH$_2$Cl$_2$ and solvent evaporated under reduced pressure. The solid residue was dissolved in 25 mL CH$_2$Cl$_2$ and washed with 50 mL of 1N HCl solution three times followed by 50 mL of saturated NaHCO$_3$ and 50 mL of saturated NaCl solution. The combined organic phase was dried over anhydrous MgSO$_4$ and the solvent was evaporated under reduced pressure to obtain yellow oil which was dried further under vacuum. The crude product was purified by SiO2 flash column chromatography eluting beginning with CH$_2$Cl$_2$ and increased polarity to 10:1 CH$_2$Cl$_2$:MeOH (R$_f$=0.38). The product eluted in fractions 7-11 (10 mL fractions collected) to afford 0.278 g (92% yield) of 2-19 as a yellowish-white solid. Crystals were grown by slow vapor diffusion of n-heptane into a solution of 2-19 in 1,2-dichloroethane: m.p. 92-93° C.; $^1$H NMR (300 MHz, CDCl$_3$) δ 7.30-7.36 (m, 5H, ArH), 5.97 (br d, J=9 Hz, 1H, NH), 5.09 (s, 2H, ArCH$_2$), 4.92 (br d, J=11 Hz, 1H, NH), 4.03-3.93 (m, 2H, BocHNCH and CONHCH), 2.37 (td, J=13, 4.5 Hz, 1H, BnO-COCH), 2.08-1.90 (m, 2H), 1.80-1.62 (m, 3H), 1.50-1.10 (m, 3H), 1.44 (s, 9H), 1.21 (d, J=8 Hz, 3H, CH$_3$); MS-ESI m/z 427.2 [M+Na]$^+$, 831.4 [2M+Na]$^+$.

Boc-D-Phe-ACHC-OBn (2-20). In an oven-dried round bottom flask, Boc-ACHC-OBn (0.20 g, 0.60 mmol) was dissolved in 4 mL of HCL/dioxane (4 M) at 0° C. The mixture was allowed to warm to room temperature and stirred for 2.5 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 5 mL of anhydrous DMF and cooled to 0° C. After stirring for 5 minutes, HOBt (0.18 g, 1.30 mmol), EDCl.HCl (0.25 g, 1.30 mmol), DIEA (0.12 mL, 0.69 mmol), and a solution of Boc-D-Phe-OH (0.16 g, 0.60 mmol) in 3 mL of anhydrous DMF were added. The mixture was allowed to warm to room temperature and stirred for 60 hours under N$_2$. Solvent was removed under reduced pressure and the solid residue dissolved in 20 mL CH$_2$Cl$_2$. The resulting solution was washed with 40 mL of 1N HCl solution three times followed by 40 mL of saturated NaHCO$_3$ and 40 mL of saturated NaCl solution. The combined organic phase was dried over anhydrous MgSO$_4$ and the solvent was evaporated under reduced pressure to obtain a white solid which was dried further under vacuum. The crude product was purified by SiO2 flash column chromatography eluting with 70:1 CH$_2$Cl$_2$:MeOH (R$_f$=0.29). The product eluted in fractions 9-13 (10 mL fractions collected) to afford 0.270 g (94% yield) of 2-20 as a white solid. Crystals were grown by slow vapor diffusion of n-heptane into a solution of 2-20 in 1,2-dichloroethane: m.p. 181-182° C.; $^1$H NMR (300 MHz, CDCl$_3$) δ 7.37-7.18 (m, 10H, ArH), 5.87 (br d, J=8.7 Hz, 1H, NH), 5.04 (app q, J$_{app}$=8 Hz, 2H, ArC$\underline{H}_2$OCO), 4.90 (br s, 1H, NH), 4.24-4.17 (m, 1H, BocHNC$\underline{H}$), 4.00 (tdd, J=11.1, 8.7, 4.2, 1H, CONHC$\underline{H}$), 2.98 (d, J=6.6, 2H, ArC$\underline{H}_2$CH), 2.34 (td, J=11.1, 3.9 Hz, 1H, BnOCOC$\underline{H}$), 2.01-1.87 (m, 2H), 1.72-1.33 (m, 4H), 1.41 (s, 9H), 1.27-1.11 (m, 2H); MS-ESI m/z 503.2 [M+Na]$^+$, 983.4 [2M+Na]$^+$.

Boc-D-Val-ACHC-OBn (2-21). In an oven-dried round bottom flask, Boc-ACHC-OBn (0.53 g, 1.58 mmol) was dissolved in 3 mL of HCL/dioxane (4 M) at 0° C. The mixture was allowed to warm to room temperature and stirred for 3.5 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 10 mL of anhydrous DMF and cooled to 0° C. After stirring for 5 minutes, HOBt (0.47 g, 3.47 mmol), EDCI.HCl (0.67 g, 3.47 mmol), DIEA (0.41 mL, 2.37 mmol), and a solution of Boc-D-Val-OH (0.34 g, 1.58 mmol) in 6 mL of anhydrous DMF were added. The mixture was allowed to warm to room temperature and stirred for 48 hours under N$_2$. Diluted mixture with 25 mL CH$_2$Cl$_2$ and transferred to a larger flask. Solvent was removed under reduced pressure and the solid residue dissolved in 30 mL CH$_2$Cl$_2$. The resulting solution was washed with 50 mL of 1N HCl solution three times followed by 50 mL of saturated NaHCO$_3$ and 50 mL of saturated NaCl solution. The combined organic phase was dried over anhydrous MgSO$_4$ and the solvent was evaporated under reduced pressure to obtain a white solid which was dried further under vacuum. The crude product was purified by SiO2 flash column chromatography eluting with 30:1 CH$_2$Cl$_2$:MeOH (R$_f$=0.28). The product eluted in fractions 8-12 (10 mL fractions collected) to afford 0.55 g (80% yield) of 2-21 as a white solid. Crystals were grown by slow vapor diffusion of n-heptane into a solution of 2-21 in 1,2-dichloroethane: m.p. 138-140° C.; $^1$H NMR (300 MHz, CDCl$_3$) δ 7.40-7.28 (m, 5H, ArH), 5.80 (br d, J=8.4 Hz, 1H, NH), 5.14-5.09 (m, 3H, ArC$\underline{H}_2$ & NH), 4.07 (ddd, J=14.7, 8.4, 3.9, 1H, BocHNC$\underline{H}$), 3.75 (app q, J$_{app}$=6.3, 1H, CONHC$\underline{H}$), 2.39 (td, J=11.4, 3.9 Hz, 1H, BnOCOC$\underline{H}$), 2.09-1.94 (m, 3H), 1.76-1.52 (m, 4H), 1.45 (s, 9H), 1.40-1.15 (m, 2H) 0.89 (t, J=6.9, 6H, 2CH$_3$); MS-ESI m/z 455.2 [M+Na]$^+$, 887.4 [2M+Na]$^+$.

Boc-D-Val-D-Phe-ACHC-OBn (2-22). In an oven-dried round bottom flask, Boc-D-Phe-ACHC-OBn (0.227 g, 0.47 mmol) was dissolved in 2 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 3 mL of anhydrous DMF and cooled to 0° C. After stirring for 5 minutes, 1.42 mmol of DIEA was added via syringe and the mixture was stirred for 10 minutes. In another oven-dried round bottom flask, Boc-D-Val-OH (0.102 g, 0.47 mmol) was dissolved in 3 mL of DMF followed by addition of HOBt (0.141 g, 1.04 mmol), and EDC.HCl (0.199 g, 1.04 mmol) and the mixture cooled to 0° C. The solution of amine and DIEA was then transferred to the flask containing Boc-Val-OH, HOBt and EDC.HCl. The mixture was allowed to warm to room temperature and stirred for 72 hours under N$_2$. Diluted mixture with 20 mL CH$_2$Cl$_2$ and transferred to a larger flask. Solvent was removed under reduced pressure and the solid residue dissolved in 25 mL CH$_2$Cl$_2$. The resulting solution was washed with 30 mL of 1N HCl solution three times followed by 30 mL of saturated NaHCO$_3$ and 30 mL of saturated NaCl solution. The combined organic phase was dried over anhydrous MgSO$_4$ and the solvent was evaporated under reduced pressure to obtain a white solid which was dried further under vacuum. The crude product was purified by SiO2 flash column chromatography eluting with 30:1 CH$_2$Cl$_2$:MeOH (R$_f$=0.21). The product eluted in fractions 9-13 (10 mL fractions collected) to afford 0.233 g (85% yield) of 2-22 as a tan solid. Crystals were grown by slow vapor diffusion of 1:1 1,2-dichloroethane:hexane into a solution of 2-22 in 1,2-dichloroethane and methanol: m.p. 187-189° C.; $^1$H NMR (300 Mz, CDCl$_3$) δ 7.37-7.14 (m, 10H, ArH), 6.34 (br d, J=7.2 Hz, 1H, NH), 6.20 (br d, J=7.2 Hz, 1H, NH), 5.07 (app q, J$_{app}$=6.3 Hz, 2H, ArC$\underline{H}_2$OCO), 4.76 (br d, J=4.2 Hz, 1H, NH), 4.59-4.52 (m, 1H, ArCH$_2$C$\underline{H}$), 4.03 (ddd, J=12.6, 10.8, 3.9, 1H, BocHNC$\underline{H}$), 3.81 (app q, J$_{app}$=5.1, 1H, CONHC$\underline{H}$), 3.13-3.04 (m, 1H, ArC$\underline{H}_2$), 2.98-2.88 (m, 1H, ArC$\underline{H}_2$), 2.36 (td, J=11.4, 3.9 Hz, 1H, BnOCOC$\underline{H}$), 2.20-2.09 (m, 1H), 1.94-1.87 (m, 2H), 1.69-1.43 (m, 4H), 1.44-1.00 (m, 2H), 1.39 (s, 9H), 0.89 (d, J=6.9 Hz, 3H, CH$_3$) 0.77 (d, J=6.9 Hz, 3H, CH$_3$); MS-ESI m/z 602.3 [M+Na]$^+$, 1181.6 [2M+Na]$^+$.

Boc-ACUC-D-Phe-ACHC-OBn (2-23). In an oven-dried round bottom flask, Boc-D-Phe-ACHC-OBn (0.047 g, 0.097 mmol) was dissolved in 1 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 3 mL of anhydrous DMF and cooled to 0° C. After stirring for 5 minutes, 0.388 mmol of DIEA was added via syringe and the mixture was stirred for 10 minutes. In another oven-dried round bottom flask, Boc-ACHC-OH (0.0236 g, 0.097 mmol) was dissolved in 3 mL of DMF followed by addition of HOBt (0.016 g, 0.117 mmol), and EDCI.HCl (0.022 g, 0.117 mmol) and the mixture cooled to 0° C. The solution of amine and DIEA was then transferred to the flask containing Boc-ACHC-OH, HOBt and EDCI.HCl. The mixture was allowed to warm to room temperature and stirred for 38 hours under N$_2$. The solvent was removed under a stream of N$_2$ and reduced pressure and the residue was dried under vacuum. This residue was washed with IN HCl solution and saturated NaHCO$_3$ solution. The solid that did not dissolve was collected by suction filtration and dried under vacuum to obtain a brownish-white solid. The crude product was purified by SiO$_2$ flash column chromatography eluting with 30:1 CHCl$_3$: MeOH (R$_f$=0.30). The product eluted in fractions 7-10 (10 mL fractions collected) to afford 0.031 g (52% yield) of 2-23 as a white solid. Crystals were grown by slow vapor diffusion of 1:1 1,2-dichloroethane:hexane into a solution of 2-23 in 1,2-dichloroethane and methanol: m.p. 232-235° C.; $^1$H NMR (300 MHz, CDCl$_3$/CD$_3$OD) δ 7.46-7.13 (m, 10H, ArH), 5.05 (br s, 2H, ArC$\underline{H}_2$OCO), 4.53-4.48 (m, 1H, ArCH$_2$C$\underline{H}$), 4.00-3.98 (m, 1H, BocHNC$\underline{H}$), 3.49-3.40 (m, 1H, CONHC$\underline{H}$), 3.00-2.94 (m, 1H, ArC$\underline{H}_2$), 2.80-2.72 (m, 1H, ArC$\underline{H}_2$), 2.39 (td, J=11.4, 3.6 Hz, 1H, BnOCOC$\underline{H}$), 2.09-1.90 (m, 4H), 1.77-1.53 (m, 7H), 1.45-1.14 (m, 5H), 1.40 (s, 9H); MS-ESI m/z 628.3 [M+Na]$^+$, 1234.6 [2M+Na]$^+$.

Boc-ACHC-D-Val-ACHC-OBn (2-24). In an oven-dried round bottom flask, Boc-D-Val-ACHC-OBn (0.118 g, 0.272 mmol) was dissolved in 2 mL of HCL/dioxane (4 M) at 0° C. The mixture was allowed to warm to room temperature and stirred for 1.5 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 3 mL of anhydrous DMF and cooled to 0° C. After stirring for 5 minutes, 1.085 mmol of DIEA was added via syringe and the mixture was stirred for 10 minutes. In another oven-dried round bottom flask, Boc-ACHC-OH (0.0661 g, 0.272 mmol) was dissolved in 3 mL of DMF followed by addition of HOBt (0.0441 g, 0.326 mmol), and EDCI.HCl (0.0625 g, 0.326 mmol) and the mixture cooled to 0° C. The solution of amine and DIEA was then transferred to the flask containing Boc-ACHC-OH, HOBt and EDCI.HCl. The mixture was allowed to warm to room temperature and stirred for 40 hours under $N_2$. The solvent was removed under a stream of $N_2$ and reduced pressure and the residue was dried under vacuum. This residue was washed with 1N HCl solution and saturated $NaHCO_3$ solution. The solid that did not dissolve was collected by suction filtration and dried under vacuum to obtain a white solid. The crude product was purified by $SiO_2$ flash column chromatography eluting with 30:1 $CHCl_3$:MeOH ($R_f$=0.36). The product eluted in fractions 6-11 (10 mL fractions collected) to afford 0.094 g (62% yield) of 2-24 as a white solid. Crystals were grown by slow vapor diffusion of 1:1 1,2-dichloroethane:hexane into a solution of 2-24 in 1,2-dichloroethane and methanol: m.p. 245-247° C.; $^1$H NMR (300 MHz, $CDCl_3/CD_3OD$) δ 7.48-7.30 (m, 5H, ArH), 5.09 (s, 2H, ArC$\underline{H}_2$OCO), 4.09-4.00 (m, 2H, BocHNC$\underline{H}$ & $(CH_3)_2$CHC$\underline{H}$), 3.58-3.49 (m, 1H, CONHC$\underline{H}$), 2.43 (td, J=11.7, 4.0 Hz, 1H, BnOCOC$\underline{H}$), 2.18 (td, J=11.7, 4.0 Hz, 1H, NHCOC$\underline{H}$), 2.10-1.86 (m, 5H), 1.82-1.73 (m, 4H), 1.61-1.54 (m, 3H), 1.44-1.13 (m, 5H), 1.41 (s, 9H); MS-ESI m/z 580.3 [M+Na]$^+$, 1138.7 [2M+Na]$^+$.

Boc-D-Lys(2-Cl-Z)-D-Val-ACHC-OBn (2-25). In an oven-dried round bottom flask, Boc-D-Val-ACHC-OBn (0.186 g, 0.430 mmol) was dissolved in 2 mL of HCL/dioxane (4 M) at 0° C. The mixture was allowed to warm to room temperature and stirred for 2 hours. The solvent was then removed under a stream of $N_2$ and under reduced pressure to obtain a white solid. The residue was dried under vacuum for 1 hour. The HCl salts were used without further purification. In an oven-dried round bottom flask, the resulting HCl salt was dissolved in 3 mL of anhydrous DMF and cooled to 0° C. After stirring for 5 minutes, 0.642 mmol of DIEA was added via syringe and the mixture was stirred for 10 minutes. In another oven-dried round bottom flask, Boc-D-Lys(2-Cl—Z)—OH (0.178 g, 0.430 mmol) was dissolved in 3 mL of DMF followed by addition of HOBt (0.128 g, 0.950 mmol), and EDCI.HCl (0.181 g, 0.950 mmol) and the mixture cooled to 0° C. The solution of amine and DIEA was then transferred to the flask containing Boc-D-Lys(2-Cl—Z)—OH, HOBt and EDCI.HCl. The mixture was allowed to warm to room temperature and stirred for 48 hours under $N_2$. The solvent was removed under a stream of $N_2$ and reduced pressure and the residue was dried under vacuum. This residue was washed with 1N HCl solution and saturated $NaHCO_3$ solution. The solid that did not dissolve was collected by suction filtration and dried under vacuum to obtain a white solid. The crude product was purified by $SiO_2$ flash column chromatography eluting with 30:1 $CHCl_3$:MeOH ($R_f$=0.20). The product eluted after increasing solvent polarity to $CHCl_3$:MeOH 1:1. Product was dried under vacuum to afford 0.263 g (84% yield) of 2-25 as a white solid. Crystals were grown by slow vapor diffusion of 1:1 1,2-dichloroethane:hexane into a solution of 2-25 in 1,2-dichloroethane and methanol:

m.p. 210-212° C.; $^1$H NMR (300 Mz, $CDCl_3/CD_3OD$) δ 7.70 (br d, J=4.2, 1H, NH) 7.44-7.24 (m, 9H, ArH), 5.20 (s, 2H, ArClC$\underline{H}_2$), 5.06 (s, 2H, ArC$\underline{H}_2$OCO), 4.06-3.96 (m, 3H), 3.39-3.37 (m, 1H), 3.16 (t, J=6.3 Hz, 2H), 2.39 (td, J=12.0, 3.6 Hz, 1H, BnOCOC$\underline{H}$), 2.10-1.90 (m, 3H), 1.76-1.68 (m, 3H), 1.60-1.09 (m, 9H), 1.43 (s, 9H), 0.87 (d, J=3.6 Hz, 3H, $CH_3$), 0.84 (d, J=3.6 Hz, 3H, $CH_3$); MS-ESI m/z 751.3 [M+Na]$^+$, 1481.6 [2M+Na]$^+$.

Boc-D-Ala-ACHC-D-Ala-ACHC-OBn (2-26). In an oven-dried round bottom flask, Boc-D-Ala-ACHC-OBn (0.056 g, 0.139 mmol) was dissolved in 1 mL of HCl/dioxane (4 M) at 0° C. The mixture was allowed to warm to room temperature and stirred for 2 hours. The solvent was then removed under a stream of $N_2$ and under reduced pressure to obtain a tan solid. The residue was dried under vacuum for 1 hour. The HCl salts were used without further purification. In an oven-dried round bottom flask, the resulting HCl salt was dissolved in 2 mL of anhydrous DMF and cooled to 0° C. After stirring for 5 minutes, 0.208 mmol of DIEA was added via syringe and the mixture was stirred for 10 minutes. In another oven-dried round bottom flask, Boc-D-Ala-ACHC-OH (0.0435 g, 0.139 mmol) was dissolved in 2 mL of DMF followed by addition of HOBt (0.041 g, 0.305 mmol), and EDCI.HCl (0.058 g, 0.305 mmol) and the mixture cooled to 0° C. The solution of amine and DIEA was then transferred to the flask containing Boc-D-Ala-ACHC-OH, HOBt and EDCI.HCl. The mixture was allowed to warm to room temperature and stirred for 76 hours under $N_2$. The solvent was removed under a stream of $N_2$ and reduced pressure and the residue was dried under vacuum. This residue was diluted with $CH_2Cl_2$ and washed three times with 20 mL 1N HCl solution, three times with 20 mL saturated $NaHCO_3$ solution and once with 20 mL aqueous NaCl solution. The organic phase was dried in anhydrous $MgSO_4$ and concentrated on a rotary evaporator. The residue was dried under vacuum to obtain a pale yellow solid. The crude product was purified by $SiO_2$ flash column chromatography eluting with 20:1 $CH_2Cl_2$:MeOH ($R_f$=0.30). The product eluted in fractions 6-11 (10 mL fractions collected). The product was then dried under vacuum to afford 0.062 g (75% yield) of 2-26 as a white solid. Crystals were grown by slow vapor diffusion of 1:1 1,2-dichloroethane:hexane into a solution of 2-26 in 1,2-dichloroethane and methanol: m.p. 202-203° C.; 1H NMR (300 MHz, $CDCl_3/CD_3OH$) δ 7.70 (br d, J=8.7, 1H, NH), 7.57 (br d, J=8.1, 1H, NH), 7.36-7.28 (m, 5H, ArH), 6.00 (br d, J=6.9, 1H, NH), 5.08 (s, 2H, ArC$\underline{H}_2$OCO), 4.18-4.14 (m, 2H, NHC$\underline{H}$CO), 4.08-3.96 (m, 2H, CONHC$\underline{H}$), 2.36 (td, J=11.7, 3.6 Hz, 1H, HNCOC$\underline{H}$), 2.30-2.22 (m, 1H, BnOCOC$\underline{H}$), 2.01-1.74 (m, 7H), 1.64-1.25 (m, 9H), 1.44 (s, 9H), 1.20 (d, J=6.9 Hz, 3H, $CH_3$), 1.16 (d, J=6.9 Hz, 3H, $CH_3$); MS-ESI m/z 623.3 [M+Na]$^+$, 1223.6 [2M+Na]$^+$.

Boc-D-PheACHC-D-Phe-ACHC-OBn (2-27). In an oven-dried round bottom flask, Boc-D-Phe-ACHC-OBn (0.0167 g, 0.035 mmol) was dissolved in 1 mL of HCL/dioxane (4 M) at 0° C. The mixture was allowed to warm to room temperature and stirred for 2 hours. The solvent was then removed under a stream of $N_2$ and under reduced pressure to obtain a white solid. The residue was dried under vacuum for 1 hour. The HCl salts were used without further purification. In an oven-dried round bottom flask, the resulting HCl salt was dissolved in 1 mL of anhydrous DMF and cooled to 0° C. After stirring for 5 minutes, 0.052 mmol of DIEA was added via syringe and the mixture was stirred for 10 minutes. Boc-D-Phe-ACHC-OH (0.0134 g, 0.035 mmol), HOBt (0.0103 g, 0.076 mmol), and EDCI.HCl (0.0147 g, 0.076 mmol) were added at 0° C. The mixture was allowed to warm to room temperature and stirred for 53 hours under $N_2$. The solvent was removed under a stream of $N_2$ and reduced pressure and the residue was dried under vacuum. This residue was diluted with $CH_2Cl_2$ and washed three times with 20 mL 1N HCl solution, three times with 20 mL saturated NaHCO$_3$ solution and once with 20 mL aqueous NaCl solution. The organic phase was dried in anhydrous MgSO$_4$ and concentrated on a rotary evaporator. The residue was dried under vacuum to obtain a brown solid. The crude product was purified by SiO$_2$ flash column chromatography eluting with 30:1 CHCl$_3$:MeOH (R$_f$=0.29). The product eluted in fractions 7-11 (10 mL fractions collected). The product was dried under vacuum to afford 0.0187 g (72% yield) of 2-27 as a white solid. Crystals were grown by slow vapor diffusion of 1:1 1,2-dichloroethane:hexane into a solution of 2-27 in 1,2-dichloroethane and methanol: m.p. 244-245° C.; 1H NMR (300 MHz, CDCl$_3$/CD$_3$OD) 7.36-7.15 (m, 15H, ArH), 5.06 (s, 2H, ArCH$_2$OCO), 4.59-4.55 (m, 1H, NHCHCO), 4.25-4.22 (m, 1H, NHCHCO), 3.87-3.77 (m, 2H), 2.94-2.88 (m, 2H, ArCH$_2$), 2.70-2.59 (m, 2H, ArCH$_2$), 2.30-2.17(m, 2H), 1.99-1.85 (m, 2H), 1.74-1.05 (m, 12H), 1.32 (s, 9H), 0.9-0.85(m, 2H); MS-ESI m/z 775.4 [M+Na]$^+$.

Boc-D-Val-ACHC-D-Val-ACHC-OBn (2-28). In an oven-dried round bottom flask, Boc-D-Val-ACHC-OBn (0.111 g, 0.257 mmol) was dissolved in 3 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 3 mL of anhydrous DMF and cooled to 0° C. After stirring for 5 minutes, 1.03 mmol of DIEA was added via syringe and the mixture was stirred for 10 minutes. In another oven-dried round bottom flask, Boc-D-Val-ACHC-OH (0.088 g, 0.257 mmol) was dissolved in 3 mL of DMF followed by addition of HOBt (0.042 g, 0.311 mmol), and EDCl-HCl (0.059 g, 0.311 mmol) and the mixture cooled to 0° C. The solution of amine and DIEA was then transferred to the flask containing Boc-D-Val-ACHC-OH, HOBt and EDCl.HCl. The mixture was allowed to warm to room temperature and stirred for 48 hours under N$_2$ during which time a white solid precipitated. The solvent was removed under a stream of N$_2$ and reduced pressure and the residue was dried under vacuum. This residue was diluted with CH$_2$Cl$_2$ (sparingly soluble) and washed three times with 25 mL 1N HCl solution, three times with 25 mL saturated NaHCO$_3$ solution and once with 25 mL aqueous NaCl solution. The organic phase was dried in anhydrous MgSO$_4$ and concentrated on a rotary evaporator. The residue was dried under vacuum to obtain a white solid. The crude product could not be purified by SiO$_2$ flash column chromatography because of poor solubility in organic solvents. The crude product was purified by washing with acetone and filtering to obtain 0.135 g (80%) of white solid. A mini workup for NMR purpose involved taking a sample of the product and reacting with CF$_3$COOH to obtain the trifluoroacetate and then dissolving in acetone and filtered to obtain a white solid. This white solid could then be dissolved in CDCl$_3$/CD$_3$OD for NMR. Crystals were grown by slow vapor diffusion of 1:1 1,2-dichloroethane:hexane into a solution of 2-28 in 1,2-dichloroethane and methanol: m.p. 254-256° C. (free amine); $^1$H NMR (300 MHz, CDCl$_3$/CD$_3$OD) (Free amine) δ 7.39-7.32 (m, 5H, ArH), 5.08 (app q, J=12.6 Hz, ArCH$_2$), 4.06-3.95 (m, 2H), 3.61 (td, J=10.8, 3.3 Hz, 1H, CONHCH), 3.40-3.35 (m, 1H, CONHCH), 2.69 (td, J=11.1, 3.0 Hz, 1H, HNCOCH), 2.44 (td, J=11.7, 3.9 Hz, 1H) BnOCOCH), 2.13-1.81 (m, 10H), 1.62-1.18 (m, 8H), 0.99 (app q, J=3.3 Hz, 6H, 2CH$_3$), d, J=6 Hz, 6H, 2CH$_3$); MS-ESI m/z (Free amine) 557.3 [M+H]+, 579.3 [M+Na]$^+$, 1135.6 [2M+Na]$^+$; (Boc-product) 679.4 [M+Na]$^+$, 1335.7 [2M+Na]$^+$.

Boc-D-(Lys2-Cl-Z)-D-Val-D-Phe-ACHC-OBn (2-29). In an oven-dried round bottom flask, Boc-D-Val-D-Phe-ACHC-OBn (0.274 g, 0.473 mmol) was dissolved in 2 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 2 mL of anhydrous DMF and cooled to 0° C. After stirring for 5 minutes, 0.712 mmol of DIEA was added via syringe and the mixture was stirred for 10 minutes. In another oven-dried round bottom flask, Boc-D-Lys(2-Cl-Z)-OH (0.196 g, 0.473 mmol) was dissolved in 3 mL of DMF followed by addition of HOBt (0.141 g, 1.04 mmol), and EDCI.HCl (0.199 g, 1.04 mmol) and the mixture cooled to 0° C. The solution of amine and DIEA was then transferred to the flask containing Boc-D-Lys(2-Cl-Z)-OH, HOBt and EDCl.HCl. The mixture was allowed to warm to room temperature and stirred for 48 hours under N$_2$. The solvent was removed under a stream of N$_2$ and reduced pressure and the residue was dried under vacuum. This residue was washed with 1N HCl solution and saturated NaHCO$_3$ solution. The solid that did not dissolve was collected by suction filtration and dried under vacuum to obtain a tan solid. The crude product was purified by SiO$_2$ flash column chromatography eluting with 2:1 CH$_2$Cl$_2$:MeOH (R$_f$=0.40). The product eluted in fractions 5-9. Product was dried under vacuum to afford 0.249 g (60% yield) of 2-29 as a white solid. Crystals were grown by slow vapor diffusion of 1:1 1,2-dichloroethane:hexane into a solution of 2-29 in 1,2-dichloroethane and methanol: m.p. 192-194° C.; $^1$H NMR (300 MHz, CDCl$_3$/CD$_3$OD) δ 7.54 (br d, J=6.3, 1H, NH), 7.45-7.14 (m, 14H, ArH), 6.50(t, J=5.4 Hz, 1H, NH), 5.21 (s, 2H, ArClCH$_2$), 5.03 (app q, J$_{app}$=12.3 Hz, 2H, ArCH$_2$OCO), 4.09 (br d, J=6.0, 1H), 4.02-3.99 (m, 2H), 3.78-3.72 (m, 1H), 3.19-3.13 (m, 2H), 2.82 (app q, J$_{app}$=8.7 Hz, 1H), 2.49-2.42 (m, 1H, BnOCOCH), 2.05-1.88 (m, 3H), 1.75-1.16 (m, 14H), 1.44 (s, 9H), 0.84 (d, J=6.9 Hz, 3H, CH$_3$), 0.80 (d, J=6.9 Hz, 3H, CH$_3$); MS-ESI m/z 898.4 [M+Na]$^+$.

Boc-D-Lys(2-Cl-Z)-ACHC-D-Val-ACHC-OBn (2-30). In an oven-dried round bottom flask, Boc-D-ACHC-D-Val-ACHC-OBn (0.068 g, 0.122 mmol) was dissolved in 1 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 2 mL of anhydrous DMF and cooled to 0° C. After stirring for 5 minutes, 0.183 mmol of DIEA was added via syringe and the mixture was stirred for 10 minutes. In another oven-dried round bottom flask, Boc-D-Lys(2-Cl-Z)-OH (0.0506 g, 0.122 mmol) was dissolved in 1 mL of DMF followed by addition of HOBt (0.036 g, 0.266 mmol), and EDCI.HCl (0.051 g, 0.266 mmol) and the mixture cooled to 0° C. The solution of amine and DIEA was then transferred to the flask containing Boc-D-Lys(2-Cl-Z)-OH, HOBt and EDCl.HCl. The mixture was allowed to warm to room temperature and stirred for 48 hours under N$_2$. The solvent was removed under a stream of N$_2$ and reduced pressure and the residue was dried under vacuum. This residue was washed with 1N HCl solution and saturated NaHCO$_3$ solution. The solid that did not dissolve was collected by suction filtration and dried under vacuum to obtain a white solid. The crude product was purified by precipitation. Purification involved dissolving the white solid in minimum amount of MeOH/TFE/CHCl$_3$ and sonicating. Excess diethyl ether was added and mixture kept at 0° C. for 5 minutes and after centrifuging, the ether layer was decanted. The process was repeated three times with fresh portions of diethyl ether. The product was dried under vacuum to afford 0.094 g (90% yield) of 2-30 as a white solid: m.p. 217-219° C.; $^1$H NMR (300 MHz, CDCl$_3$/CD$_3$OD) δ 7.53 (br d, J=4.2, 1H, NH), 7.41 (br d, J=5.1, 1H, NH), 7.36-7.24 (m, 9H, ArH), 5.20 (app q, $J_{app}$=11.7 Hz, 2H, ArC$\underline{H}_2$OCO), 5.07 (s, 2H, ArClC$\underline{H}_2$), 4.12-3.99 (m, 3H), 3.86-3.80 (m, 1H, CONHC$\underline{H}$), 3.18-3.12 (m, 2H), 2.99-2.88 (m, 1H), 2.44-2.26 (m, 2H), 2.05-1.15 (m, 23H), 1.43 (s, 9H), 0.85 (br d, J=6.3 Hz, 6H, 2CH$_3$); MS-ESI m/z 876.4 [M+Na]$^+$.

Boc-ACHC-D-Lys(2-Cl-Z)-D-Val-ACHC-OBn (2-31). In an oven-dried round bottom flask, Boc-D-Lys(2-Cl-Z)-D-Val-ACHC-OBn (0.239 g, 0.328 mmol) was dissolved in 2 mL of HCL/dioxane (4 M) at 0° C. The mixture was allowed to warm to room temperature and stirred for 2 hours. The solvent was then removed under a stream of N$_2$ and under reduced pressure to obtain a white solid. The residue was dried under vacuum for 1 hour. The HCl salts were used without further purification. In an oven-dried round bottom flask, the resulting HCl salt was dissolved in 1 mL of anhydrous DM and cooled to 0° C. After stirring for 5 minutes, 0.492 mmol of DIEA was added via syringe and the mixture was stirred for 10 minutes. In another oven-dried round bottom flask, Boc-ACHC-OH (0.08 g, 0.328 mmol) was dissolved in 2 mL of DMF followed by addition of HOBt (0.097 g, 0.721 mmol), and EDCI.HCl (0.138 g, 0.721 mmol) and the mixture cooled to 0° C. The solution of amine and DIEA was then transferred to the flask containing Boc-ACHC-OH, HOBt and EDCI.HCl. The mixture was allowed to warm to room temperature and stirred for 48 hours under N$_2$. The solvent was removed under a stream of N$_2$ and reduced pressure and the residue was dried under vacuum. This residue was washed with 1N HCl solution and saturated NaHCO$_3$ solution. The solid that did not dissolve was collected by suction filtration and dried under vacuum to obtain a white solid. The crude product was purified by precipitation. Purification involved dissolving the white solid in minimum amount of MeOH/TFE/CHCl$_3$ and sonicating. Excess diethyl ether was added and mixture kept at 0° C. for 5 minutes and after centrifuging, the ether layer was decanted. The process was repeated three times with fresh portions of diethyl ether. The product was dried under vacuum to afford 0.210 g (75% yield) of 2-31 as a white solid:m.p. 288-290° C.; $^1$H NMR (300 MHz, CDCl$_3$/CD$_3$OD/TFE) δ 7.47-7.23 (m, 9H, ArH), 5.19 (s, 2H, ArClC$\underline{H}_2$), 5.06 (s, 2H, ArC$\underline{H}_2$OCO), 3.66-3.57 (m, 2H), 3.52-3.41 (m, 1H), 3.17-3.10 (m, 3H), 2.46-2.37 (m, 1H, NHCOC$\underline{H}$), 2.27-2.15 (m, 1H, BnOCOC$\underline{H}$), 1.97-1.17 (m, 23H), 1.40 (s, 9H), 0.87 (d, J=5.0 Hz, 3H, CH$_3$), 0.85 (d, J=5.0 Hz, 3H, CH$_3$); MS-ESI m/z 876.4 [M+Na]$^+$.

Ac-ACHC-D-Lys-ACHC-D-Tyr-ACHC-D-Lys-NH$_2$ (2-32). The synthesis was performed as described under the General Procedures for Solid Phase Peptide Synthesis on the automated peptide synthesizer. A 75 µmol scale for each residue was used for coupling. Cleavage of the peptide and simultaneous side chain deprotection was performed as described under the General Procedures. Extended deprotection and extended coupling (2 hour) were employed. The crude peptide was dissolved in the HPLC A solvent and purified by reverse phase HPLC employing a linear gradient from 15% to 75% solvent B over 40 minutes. MALDI-TOF-MS m/z calcd for (C$_{44}$H$_{71}$N$_9$O$_8$) [M] 854.09, found 854.0 [M], 855.0 [M+H]$^+$, 877.0 [M+Na]$^+$, 892.9 [M+K]$^+$.

Ac-ACHC-L-Lys-ACHC-L-Tyr-ACHC-L-Lys-NH$_2$ (2-33). The synthesis was performed as described under the General Procedures for Solid Phase Peptide Synthesis on the automated peptide synthesizer. A 75 µmol scale for each residue was used for coupling. Cleavage of the peptide and simultaneous side chain deprotection was performed as described under the General Procedures. Extended deprotection and extended coupling (2 hour) were employed. The crude peptide was dissolved in the HPLC A solvent and purified by reverse phase HPLC employing a linear gradient from 17% to 47% solvent B over 60 minutes. MALDI-TOF-MS m/z calcd for (C$_{44}$H$_{71}$N$_9$O$_8$) [M] 854.09, found 854.0 [M], 855.0 [M+H]$^+$, 877.0 [M+Na]$^+$, 893.0 [M+K]$^+$.

Ac-ACHC-D-Lys-ACHC-D-Tyr-ACHC-D-Lys-ACHC-D-Tyr-NH$_2$ (2-34). The synthesis was performed as described under the General Procedures for Solid Phase Peptide Synthesis on the automated peptide synthesizer. A 75 µmol scale for each residue was used for coupling. Cleavage of the peptide and simultaneous side chain deprotection was performed as described under the General Procedures. Extended deprotection and extended coupling (2 hour) were employed. The crude peptide was dissolved in the HPLC A solvent and purified by reverse phase HPLC employing a linear gradient from 35% to 95% solvent B over 40 minutes and 20% to 45% solvent B over 30 minutes. MALDI-TOF-MS m/z calcd for (C$_{60}$H$_{91}$N$_{11}$O$_{11}$) [M] 1142.43, found 1142.1 [M], 1180.1 [(M-H)+K]$^+$.

Ac-ACHC-L-Lys-ACHC-L-Tyr-ACHC-L-Lys-ACHC-L-Tyr-NH$_2$ (2-35). The synthesis was performed as described under the General Procedures for Solid Phase Peptide Synthesis on the automated peptide synthesizer. A 75 µmol scale for each residue was used for coupling. Cleavage of the peptide and simultaneous side chain deprotection was performed as described under the General Procedures. Extended deprotection and extended coupling (2 hour) were employed. The crude peptide was dissolved in the HPLC A solvent and purified by reverse phase HPLC employing a linear gradient from 25% to 40% solvent B over 30 minutes. MALDI-TOF-MS m/z calcd for (C$_{60}$H$_{91}$N$_{11}$O$_{11}$) [M] 1142.43, found 1142.3 [M], 1143. 1 [M+H]$^+$, 1165.4 [M+Na]$^+$, 1181.4 [M+K]$^+$.

Heterogeneous oligomers built from cyclic β-amino acids and aromatic γ-amino acid monomers in an alternating fashion: The goal of this Example was to design and synthesize oligomers of alternating cyclic β-amino acids and aromatic γ-amino acids. The β-amino acid monomers were thought to provide conformational stability while the aromatic monomers should easily allow backbone diversification through derivatization.

The monomers that were made are as follows:

β-amino acids:

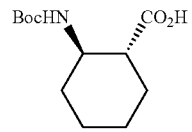
(R,R)-Boc-ACHC-OH

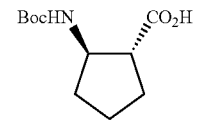
(R,R)-Boc-ACPC-OH

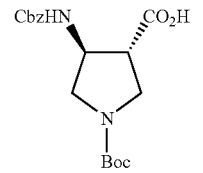
(S,R)-Cbz(Boc)-APC-OH

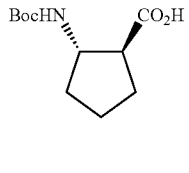
(S,S)-Boc-ACPC-OH

-continued

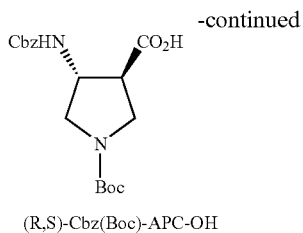

(R,S)-Cbz(Boc)-APC-OH

γ-aromatic compounds:

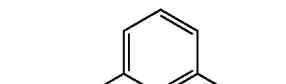
1b

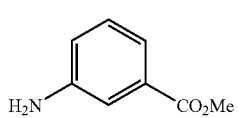
2

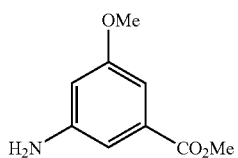
2b

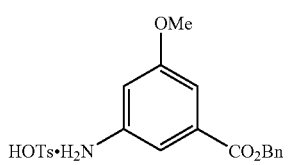
3

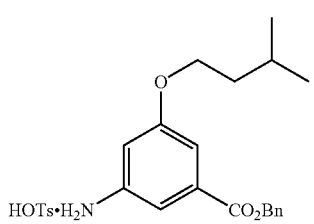
4

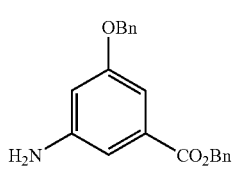
5

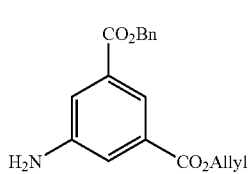

Synthesis of Monomers:

All β-amino acids were synthesized following LePlae et al. (2001) *J. Org. Chem.* 66:5629-5632.

In Scheme 4a, a general route to 5-alkyloxy-substituted aminobenzoates ("ABA"-derivatives), starting from commercially available methyl 3,5-dinitrobenzoate (6) is exemplified for compound 3. Compound 8 has been described in the literature. See Herlt, Kibby & Rickards (1981) Aust. J. Chem. 34:1319-1324.

A double alkylation of hydroxy acid 8 was found to be best accomplished by using K2CO3 as base in combination with an alkyl bromide in DMF at elevated temperature. After saponification of the ester moiety of the resulting alkoxy ester, the remaining nitro group is reduced by hydrogenation, which is followed by re-esterification as the final step. The benzylester product is obtained as p-tosyl salt. See Arai & Muramatsu (1983) J. Org. Chem. 48:121-123; and Kubik (1999) J. Am. Chem. Soc. 121:3840-3855.

In scheme 4b and 4c the synthesis of methoxy- and benzyloxy-substituted derivatives 2 and 4 is depicted. See Ragan, Makowski, Castaldi, & Hill (1998) *Synthesis* 11:1599-1603. In the case of benzyloxy compound 12, selective reduction of the nitro group is achieved with zinc in acetic acid.

Dicarboxylate 5 was synthesized according to a published procedure (scheme 1d). See Bitta & Kubik (2001) Organic Lett. 3:2637-2640.

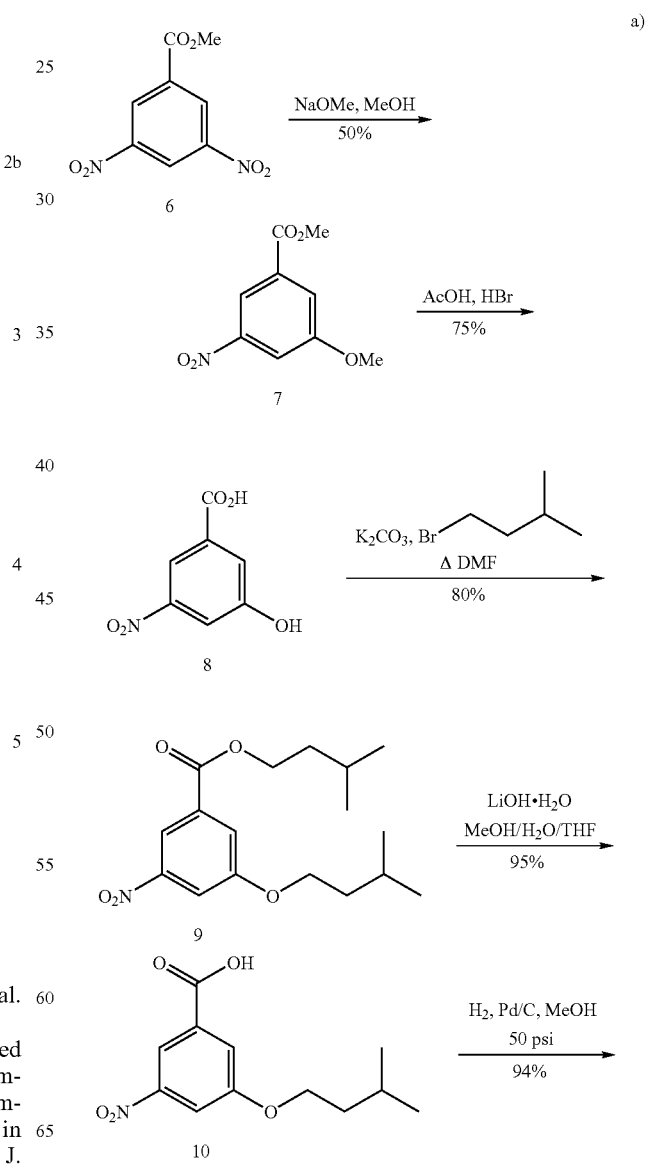

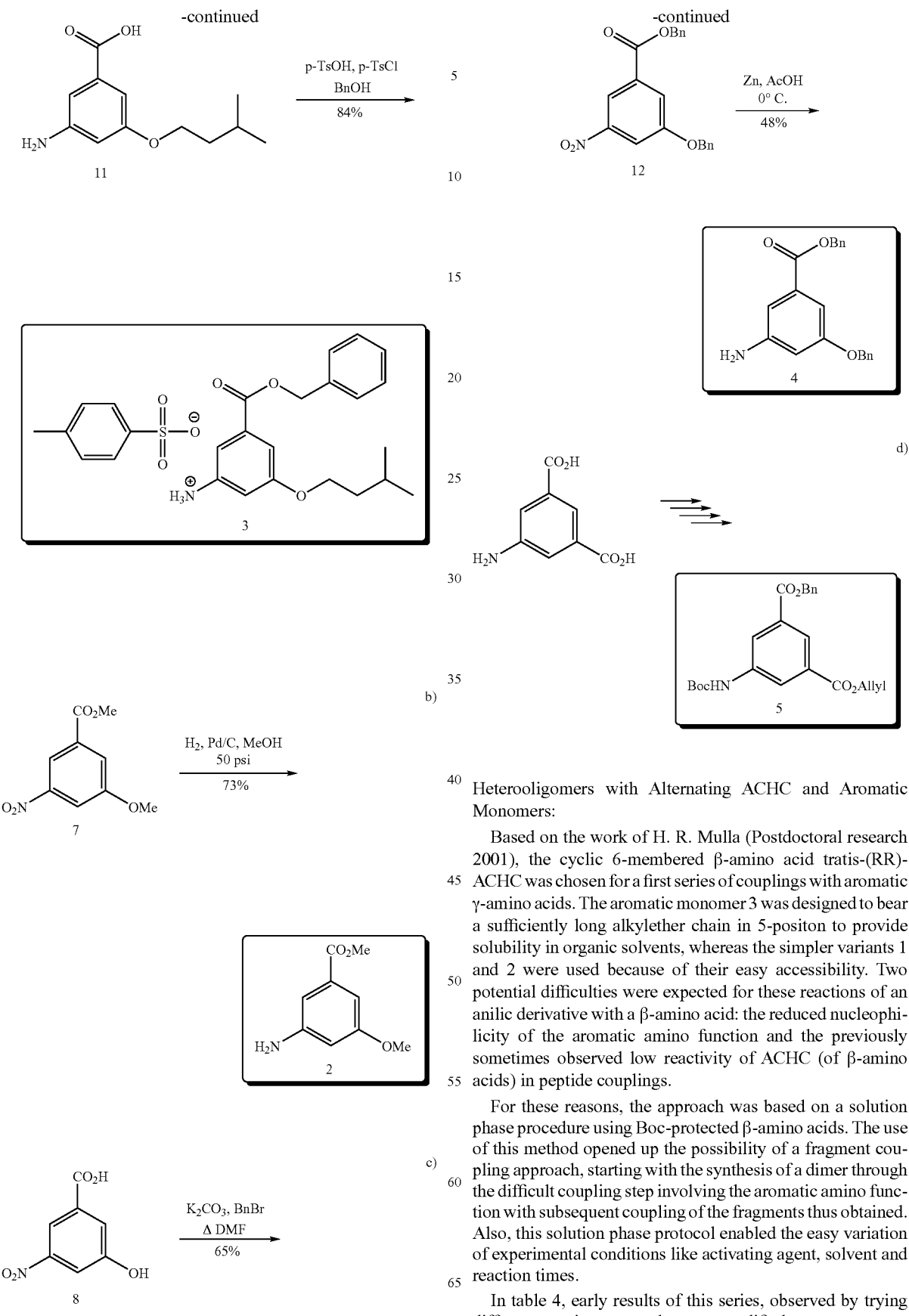

Heterooligomers with Alternating ACHC and Aromatic Monomers:

Based on the work of H. R. Mulla (Postdoctoral research 2001), the cyclic 6-membered β-amino acid tratis-(RR)-ACHC was chosen for a first series of couplings with aromatic γ-amino acids. The aromatic monomer 3 was designed to bear a sufficiently long alkylether chain in 5-positon to provide solubility in organic solvents, whereas the simpler variants 1 and 2 were used because of their easy accessibility. Two potential difficulties were expected for these reactions of an anilic derivative with a β-amino acid: the reduced nucleophilicity of the aromatic amino function and the previously sometimes observed low reactivity of ACHC (of β-amino acids) in peptide couplings.

For these reasons, the approach was based on a solution phase procedure using Boc-protected β-amino acids. The use of this method opened up the possibility of a fragment coupling approach, starting with the synthesis of a dimer through the difficult coupling step involving the aromatic amino function with subsequent coupling of the fragments thus obtained. Also, this solution phase protocol enabled the easy variation of experimental conditions like activating agent, solvent and reaction times.

In table 4, early results of this series, observed by trying different reaction protocols are exemplified.

TABLE 4

(RR)-trans-ACHC: BocNH-cyclohexyl-CO₂H + aromatic amine tosylate salt (H₃N⁺-Ar-CO₂Bn with R substituent; OTs⁻ counterion)

1 (R = H) or 3 (R = O-iso-amyl)
2b (R = OMe)

→ Dimer 15b (R = O-iso-amyl)
  15c (R = H)
  15d (R = OMe)
(BocNH-cyclohexyl-C(O)NH-Ar(R)-CO₂Bn)

| Reaction conditions | aromatic compound | Yield | Activating agent |
|---|---|---|---|
| EDCl, HOAT, DIEA, RT 3 d (CH₂Cl₂) | 1 | 11% | EDC·HCl (N,N-dimethylaminopropyl-N'-ethylcarbodiimide hydrochloride) |
| BOP-Cl, DIEA, 0° C. → RT 3 d (CH₂Cl₂) | 1 | 23% | bis(2-oxo-3-oxazolidinyl)phosphinic chloride |
| TOTU, DIEA, 0° C. → RT 3 d (CH₂Cl₂) | 1 | 28% | EtO₂C-C(CN)=N-O-C(NMe₂)=N⁺Me₂ BF₄⁻ |
| PyBroP, DIEA, RT, 4 d (CH₂Cl₂) | 2b | app. 36% | (product and starting material could not be separated by column chromatography) |
| PyCloP, DIEA, RT, 4 d or Δ, 1 d (CH₂Cl₂ or DMF) | 3 | <33% | Cl-P⁺(pyrrolidinyl)₃ PF₆⁻ |
| PyCloP, DIEA, DMAP RT, 2 d (CH₂Cl₂) | 3 | 86% | PF₆⁻ |

Generally, methylene chloride was used as solvent and DIEA (Huenig's base) as base, whereas the activating reagent as well as reaction times were varied. As aromatic compounds, non-substituted 1 or iso-amyl derivative 3 were employed mainly.

The use of standard coupling reagent EDCl in combination with HOAT, DIEA as base and methylene chloride as solvent at room temperature led to a product formation of only 11%. Other activating agents like BOP-Cl ((2-Oxo-3-oxazolidinyl)phosphinicacid chloride)′, isourea derivative TOTU (O-[(Cyan-ethoxycarbonylmethylen)-amino]-N,N,N′,N′-tetramethyluroniumtetrafluoroborat) and PyCloP (chlorotripyrrolidinophosphonium hexafluorophosphate)—reagents known for their good performance in difficult reactions—initially only resulted in low yields. Also, large amounts of starting material (amine) still present in the crude product rendered column chromatographical isolation of pure product difficult.

While neither a change of solvent (DMF) nor heating of the reaction mixture resulted in a different outcome, the addition of catalytic amounts of DMAP finally proved to be valuable: in combination with PyCloP (or bromo analogue, PyBroP, no difference observed) the reaction time for complete conversion of starting material significantly decreased and clean product could be isolated after a reaction time of 1-2 days (a second portion of DMAP was added after 1 day) and simple column chromatography.

To be able to assess the influence of the nature of the β-amino acid in the reactions, Boc-protected α-alanine or β-alanine were used in similar couplings (scheme 2), using PyCloP as activator.

Here, even in the absence of DMAP acceptable product yields were obtained after reasonable reaction times. Furthermore, the separation of product from residual starting material by column chromatography was much easier than in the cases where ACHC was involved. Overall, these reactions obviously point to the decreased reactivity of ACHC in couplings like this, compared to the acyclic β-amino acid or the α-amino acid.

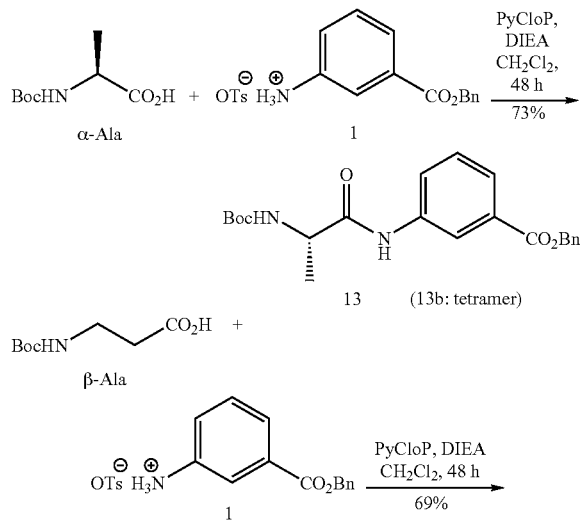

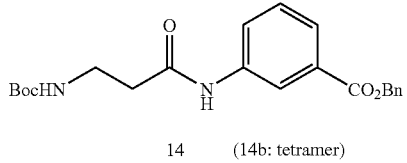

14 (14b: tetramer)

Next, the fragment coupling of two dimer fragments, which were C-deprotected at the aromatic part and N-deprotected at the amino acid part of the compound, respectively, was examined. This deprotection scheme by-passes the coupling problems resulting from decreased nucleophilicity of the aromatic amino function.

Deprotection of the benzylic ester was achieved by either applying hydrogen pressure of 50 psi for 24 hours in methanolic solution with Pd/C as catalyst, or by using conditions of a transfer hydrogenation (5 fold excess of ammonium formate, methanol, Pd/C), the latter method of which seemed to overall offer a cleaner reaction in addition to lesser reaction time. Boc-deprotection was accomplished with an excess of 4 N HCl in dioxane.

Tetramer syntheses were first attempted by applying the reaction conditions, which were found to be optimal in the dimer coupling (PyCloP, DIEA, DMAP), only exchanging methylene chloride for DMF as solvent.

In this fashion, yields of 66% and 25% were obtained in tetramer couplings of deprotected α- and β-alanine dimers 13 and 14, respectively, affording tetramers 13b, and 14b, already indicating a somewhat decreased reactivity of the simple □-amino acid compound compared to the one containing the □-amino acid.

Deprotected versions of the O-isoamyl-aminobenzoate dimer 15b containing the cyclic amino acid ACHC only yielded tetrameric coupling product 16b in ≦20% (scheme 6), no matter what reaction conditions were applied (PyCloP, EDCI/HOAT, TOTU, polypropanephosphonic acid anhydride, additions of DMAP). However, there were strong indications that a major reason for this might be the observed low solubility of the C-deprotected dimer in non-nucleophilic organic solvents.

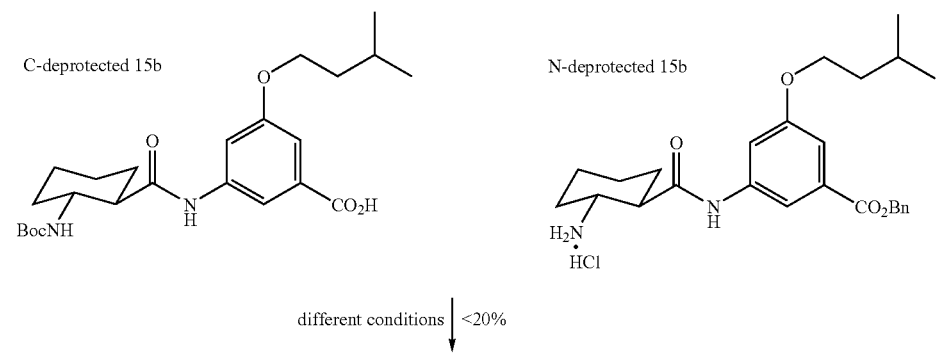

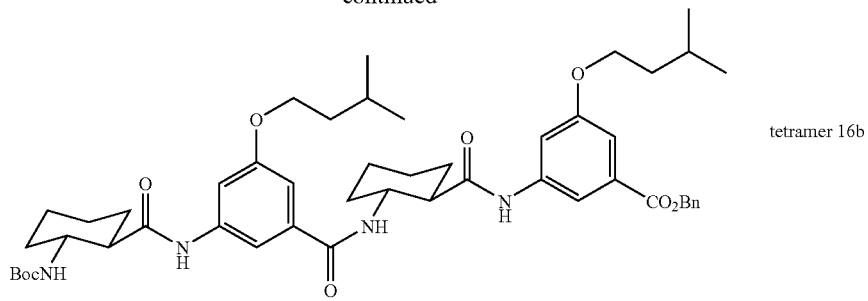

tetramer 16b

Heterooligomers with Alternating ACPC and Aromatic Monomers:

The five-ring homologue of ACHC, trans-ACPC, was thought to maybe overcome the difficulties observed with ACHC, thus a similar reaction sequence was conducted with this compound. Through repetitive couplings and deprotections, a series of oligomers comprising the building blocks (SS)-trans-ACPC and 3-O-isoamyl-aminobenzoate could be obtained in good yields (Scheme 7), using the reaction conditions found earlier to be beneficial.

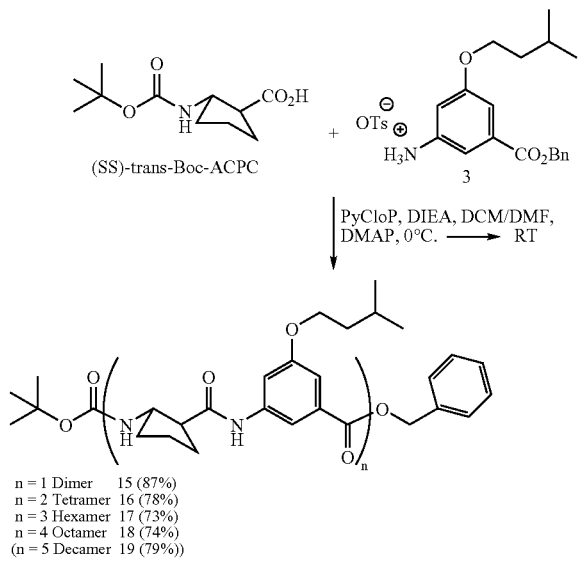

Scheme 7 n = 1 Dimer    15 (87%)
n = 2 Tetramer 16 (78%)
n = 3 Hexamer  17 (73%)
n = 4 Octamer  18 (74%)
(n = 5 Decamer 19 (79%))

Oligomers 15-19 were obtained as colorless solids, soluble in methylene chloride (and in methanol in low concentration). Unfortunately, neither of them showed a tendency for crystallization in several solvents/solvent mixtures, mostly the formation of gel-like aggregates which showed decreased solubility afterwards, seemed to be favored.

Tetramer 16, hexamer 17 and octamer 18 were examined by $^1$H NMR (300 MHz, CDCl$_3$) to obtain information about possible concentration-dependent aggregation, which can be deduced from looking at the behavior of NH-shifts at different concentrations.

Spectra were taken at concentrations ranging from 0.1 M to 0.001 M and in addition to the typical aromatic amide proton shifts at around 10 ppm, the location of several distinguishable signals in the aromatic region was focused on (alicyclic NH signals could not be distinguished from aromatic proton signals) (data not shown).

Judging from areas of constant chemical shifts, concentrations of at least 0.01 M or lower seem to be required to ensure that aggregation does not occur.

Peptides 15-19 were also examined by CD-spectroscopy (data not shown). Two separate spectra were taken for each sample solution (0.1 mM solutions in methanol in a 0.1 mm cell), 190 to 240 nm and 240 to 320 nm. All peptides except for the dimer show a minimum in the amide absorption region at around 220 nm and a maximum in the aromatic region at around 240 nm. The intensity of these depends on the oligomer length, being the strongest for the octamer, then losing intensity going from hexamer to tetramer.

Based on the building blocks ACPC and aromatic amino acid derivatives, two more series of oligomers were synthesized in solution using the fragment coupling approach: one incorporating an additional phenyl group as a benzyloxy function (scheme 8, 20-22) and another one bearing an additional benzylester group (23-25).

In the case of compounds 20 and 21 C-terminal deprotection was accomplished by saponification, while the combination of Pd(PPh$_3$)$_4$/morpholine was used for deprotection of the allylester group in 23 and 24.

All compounds were soluble (partially sonication was necessary) in pure or combinations of ethyl acetate, methanol, methylene chloride, and sample solutions were either stored at 4° C. or at room temperature with hexanes (vapor diffusion method) for two weeks.

Scheme 8

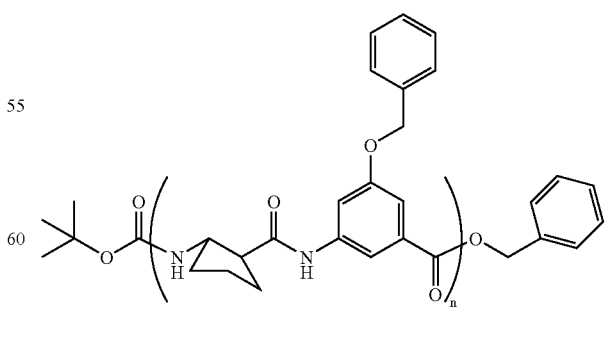

n = 1 Dimer    20 (72%)
n = 2 Tetramer 21 (58%)
n = 3 Hexamer  22 (90%)

-continued

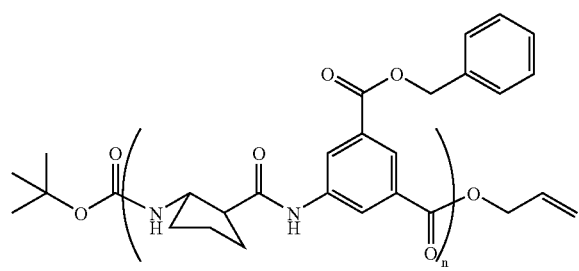

n = 1 Dimer 23 (62%)
n = 2 Tetramer 24 (80%)
n = 3 Hexamer 25 (45%)

Heterooligomers with Alternating APC and Aromatic Monomers:

(SR)-Cbz(Boc)-APC-OH and 3-amino-5-(O-methoxy)-benzoic acid methylester were combined in an alternating fashion to form a dimer and a tetramer (scheme 9, 26, 27). The design was aimed at creating oligomers with different solubility features (possibility of cleaving Boc to get water-soluble, cationic compounds).

Scheme 9

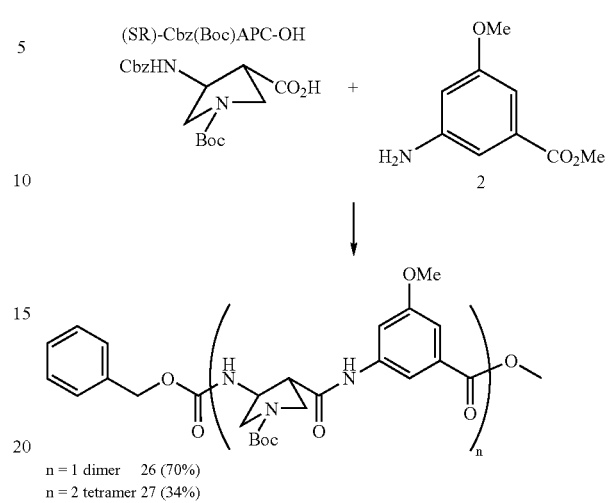

n = 1 dimer 26 (70%)
n = 2 tetramer 27 (34%)

Heterooligomers Containing APC, ACPC and Aromatic Monomers:

A series of heterogeneous oligomers (28-30) with more diversity was synthesized by using (RS)-Cbz(Boc)-APC, (SS)-ACPC and two differently substituted aminobenzoates as monomers (scheme 10).

Scheme 10

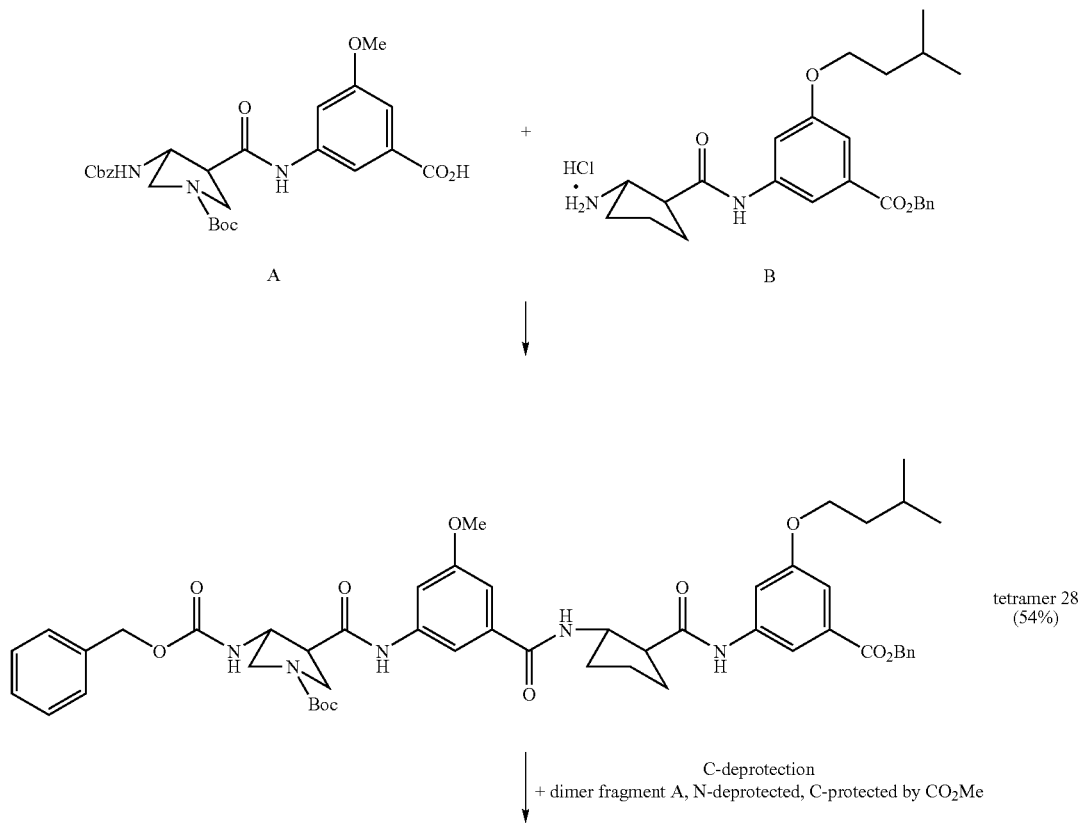

tetramer 28 (54%)

C-deprotection
+ dimer fragment A, N-deprotected, C-protected by $CO_2Me$

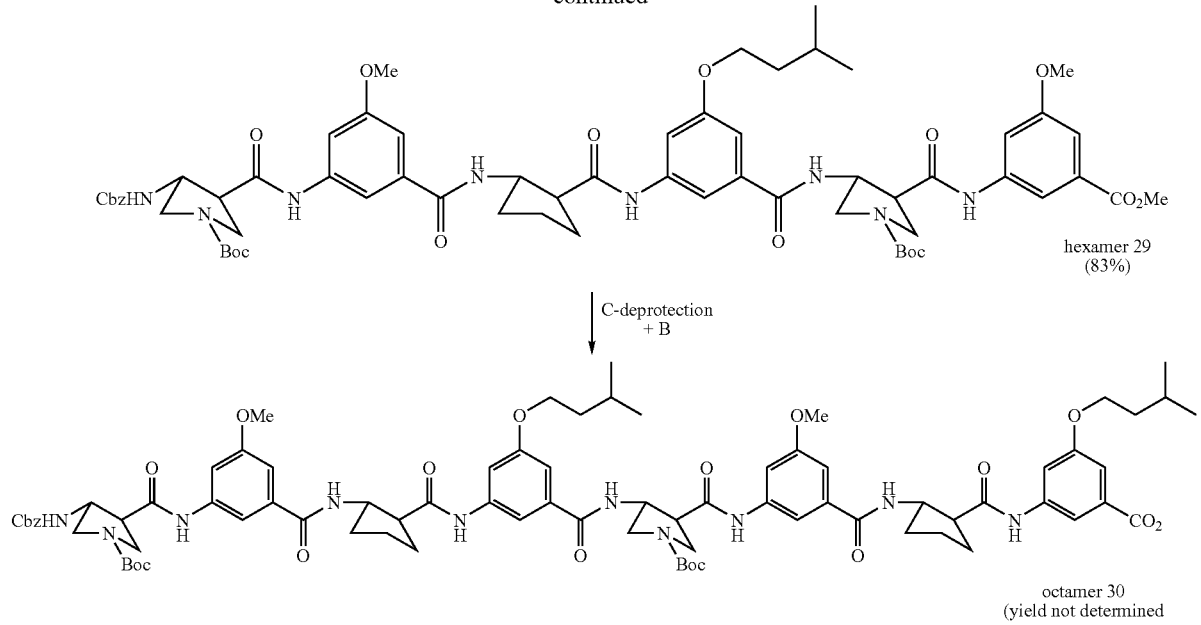

hexamer 29 (83%)

C-deprotection + B octamer 30 (yield not determined)

For future characterization studies, it would be reasonable to use only methyl esters as aromatic monomers, to avoid having any disturbance by the additional aromatic NMR signals that arise in 30 from the C-terminal benzyl ester group. The respective methyl 3-amino-5-iso-pentylbenzoate (not depicted: 3c, methyl ester derivative of monomer 3) can easily be obtained by esterification of 10 with thionyl chloride and methanol (3b, AH-II-129) followed by reductive transfer hydrogenation (3c, AH-II-133).

Heterooligomers with Alternating α-amino Acids and Aromatic Monomers:

Commercially available suitably protected α-tyrosine and α-lysine were alternately combined with a simple, non-substituted amino benzoate to form tetramer 33.

Scheme 11

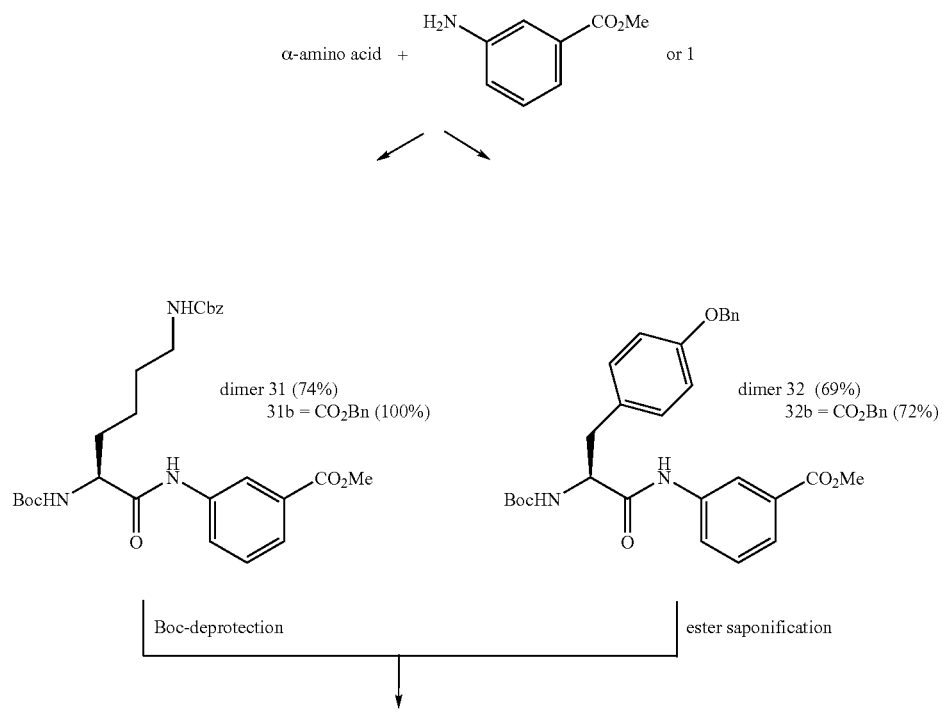

dimer 31 (74%)
31b = CO₂Bn (100%)

dimer 32 (69%)
32b = CO₂Bn (72%)

Boc-deprotection | ester saponification

-continued

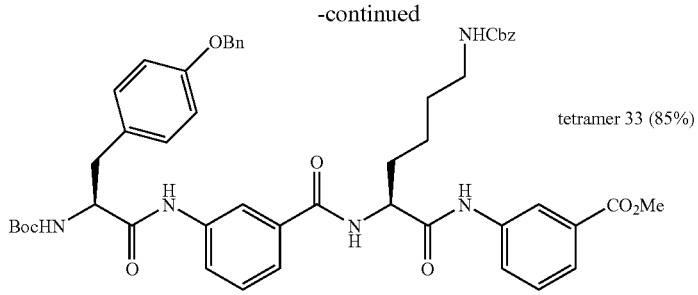

tetramer 33 (85%)

Heterogeneous Oligomers Built from Cyclic β-amino Acids and α-amino Acids in an Alternating Fashion:

The goal of this Example was to design and automatically syntheize, via solid phase synthesis, oligomers composed of alternating cyclic β-amino acids and α-amino acids.

All oligomers were synthesized from Fmoc-protected monomers by automation on the peptide synthesizer "Synergy" (Applied Biosystems Model 432A). The program used for the automated syntheses was as follows: bf—jdacgfi (coupling to amide resin)—jDaCgFi (all couplings of amino acids, C=120)—jDhccgfi (acetylation)—e. The peptides were cleaved from the resin and simultaneously deprotected with TFA/5% $H_2O$ (3 h), then precipitated twice from diethyl ether, lyophilized and purified by reversed phase semi-preparative ($C_{18}$) HPLC.

For conformational analysis, the oligomers were examined by CD-spectroscopy in methanol and buffer, and partially by NMR analysis. All peptides except for 42 were soluble in water and methanol.

The first generation of peptides, consisting of alternating ACPC and □-amino acid monomers with the general motif Ac-ACPC-K-ACPC-Y-ACPC-K-ACPC(-Y-ACPC)-$NH_2$, but comprising different stereochemical combinations, is depicted as follows:

First generation α/β peptides

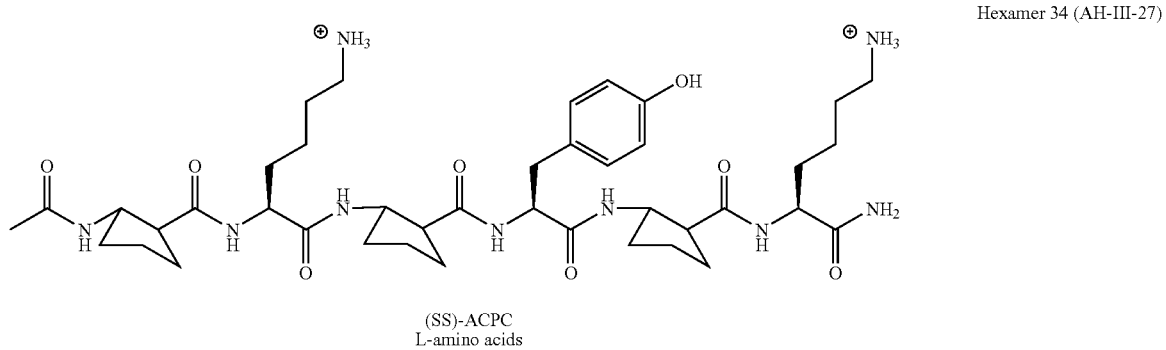

Hexamer 34 (AH-III-27)

(SS)-ACPC
L-amino acids

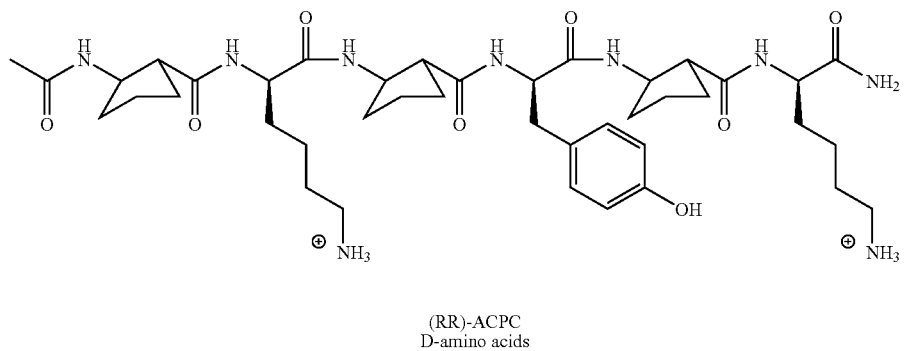

Hexamer 35 (AH-III-1)

(RR)-ACPC
D-amino acids

-continued

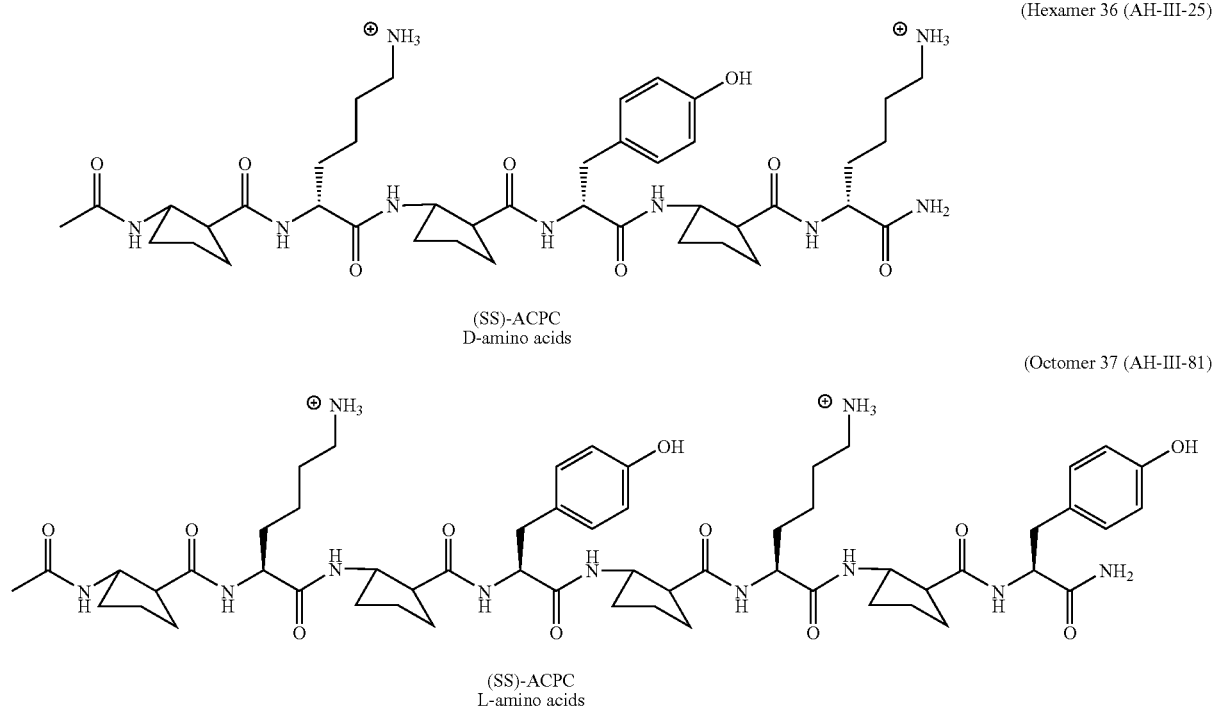

(Hexamer 36 (AH-III-25))
(SS)-ACPC
D-amino acids (Octomer 37 (AH-III-81))
(SS)-ACPC
L-amino acids In combination with ACPC as cyclic β-amino acid, tyrosine and lysine were chosen as α-amino acids to make UV-spectroscopical determination of sample solution concentration for CD possible and to create charge to facilitate HPLC purification by rendering the peptides soluble in water.

The CD spectra of compounds 34-37, in methanol buffer (pH 7) at a concentration of 0.1 mM, were taken (data not shown). As mentioned above, the presence of the tyrosine residue(s) enabled the determination of sample solution concentrations by UV-spectroscopy (☐ [Y] @ 275 nm=1420 L/mol×cm), thus eliminating a potential error source of incorrect concentrations. Peptides 34, 35 and 37 all show a strong absorption around 205 nm, which is more intense in methanol than in buffer. Compounds 34 and 35 display exactly opposite behavior, as expected by their status as enantiomers. Peptide 36, however, having a stereochemical combination of SS-ACPC amd D-amino acids in contrast to SS-ACPC and L-amino acids (or enantiomer) in the other oligomers, does not show strong maxima or minima, but a rather non-expressive curve in the CD-spectrum.

A second generation of heterooligomers with more diversity in the backbone was also designed and synthesized. Here, ACPC was used alternately with APC and in addition to lysine and tyrosine, glutamic acid and alanine were used on the α-amino acids part:

Second generation α/β peptides 38 (AH-III-59)

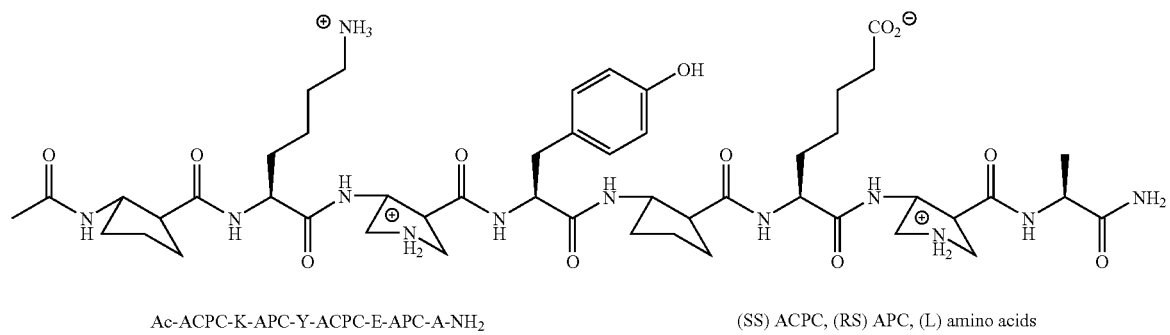

Ac-ACPC-K-APC-Y-ACPC-E-APC-A-NH₂

(SS) ACPC, (RS) APC, (L) amino acids 39 (AA-III-69)

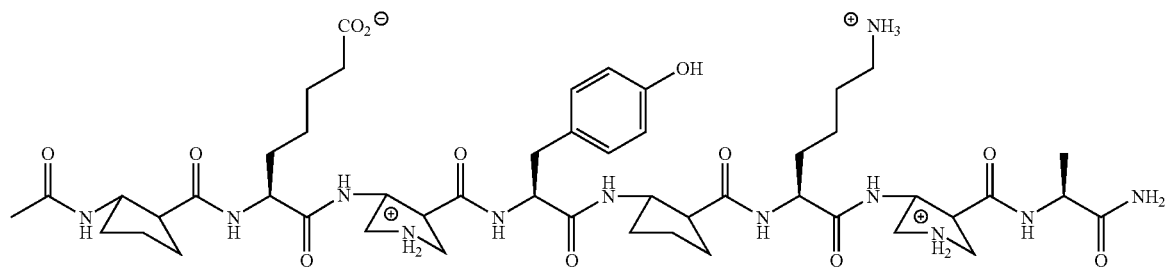

Ac-ACPC-E-APC-Y-ACPC-K-APC-A-NH₂    (SS) ACPC, (RS) APC, (L) amino acids

The CD-spectra of Peptides 38 and 39 (data not shown) exhibit a strong similarity to the ones of 34 and 37: minima at around 205 nm with the signals being more intense in methanol than in aqueous buffer.

Unfortunately, NMR analysis of peptides 38 and 39 still resulted in difficulties, although some NOE assignment was possible. Therefore, in the design of the third generation of α/β peptides, the first or the second ACPC residue, respectively, were exchanged for APC residues with para-methoxy sulfonamide groups, as this was believed to shift the amide, α- and β-protons enough to be able to distinguish between former difficult areas:

In these cases, a strong maximum is observed at around 205 nm in the CD spectra (data not shown). In contrast to all previous oligomers the opposite stereochemistry for α- and β-amino acids was used in this generation of compounds. Also, a determination of concentration was impossible due to the aromatic absorption of the APC-SO₂R-residue. Thus, the assumed concentrations determined by weighing might be an error source.

Peptide 40 in methanol exhibits the strongest signal observed to date, which decreases visibly by changing to buffer solution. For peptide 41, CD curves for both solvents (methanol vs. buffer) are very similar.

Third generation α/β peptides 40 (AH-III-109)

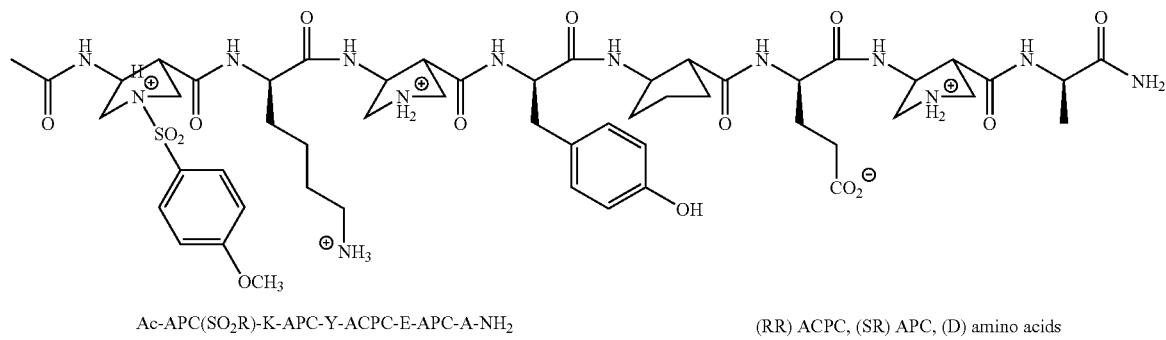

Ac-APC(SO₂R)-K-APC-Y-ACPC-E-APC-A-NH₂    (RR) ACPC, (SR) APC, (D) amino acids 41 (AH-III-111)

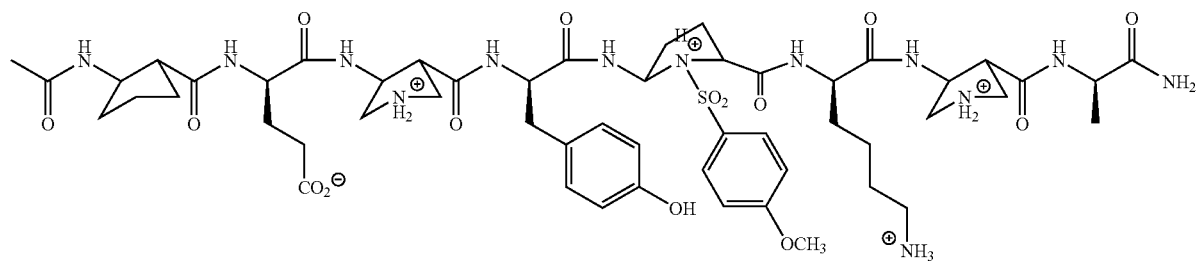

AC-ACPC-E-APC-Y-APC(SO₂R)-K-APC-A-NH₂    (RR) ACPC, (SR) APC, (D) amino acids

Peptide 42, another oligomer from the 5-ring series with alternating phenylalanine and ACPC residues, was also made. The crude compound turned out to be insoluble in common solvents like water, methanol, acetonitrile, acetone, ethyl acetate and methylene chloride, and DMSO. Thus, a purification via HPLC was not possible. The molecular weight of the peptide was confirmed by taking MALDI-TOF of a dilute sample in a solvent mixture.

Peptide 42

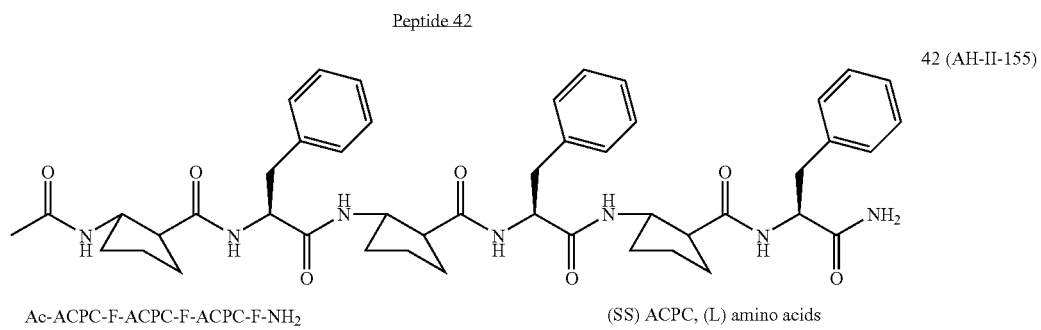

Ac-ACPC-F-ACPC-F-ACPC-F-NH$_2$
(SS) ACPC, (L) amino acids 42 (AH-II-155)

In another series of compounds made, the first generation of peptides (shown above), consisting of alternating 6-ring-β-amino acids (ACHC and PEP) and α-amino acid monomers with the same general motif as in 5-ring oligomers 38 and 39, but comprising different variants of stereochemical combinations, were made are depicted as compounds 43-56.

The automated synthesis of these compounds was more problematic than the synthesis of the 5-ring oligomers (34-41): yields were reduced by unsuccessful deprotection steps with the result of several deletion peptides as byproducts. Curiously, only in the cases of oligomers comprising L-amino acids large amounts of still Fmoc-protected products could also be observed in addition to deletion peptides.

6-ring α/β peptides 43–46

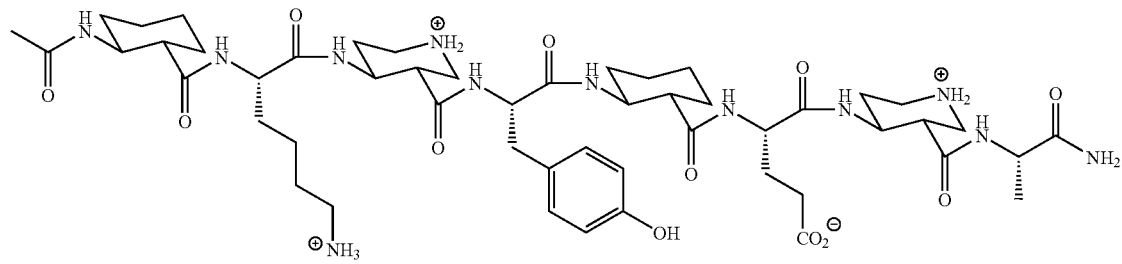

43 (AH-III-89)

Ac-ACHC-K-PIP-Y-ACHC-E-PIP-A-NH$_2$
(SS) ACHC, (SS) PIP, (L) amino acids

-continued

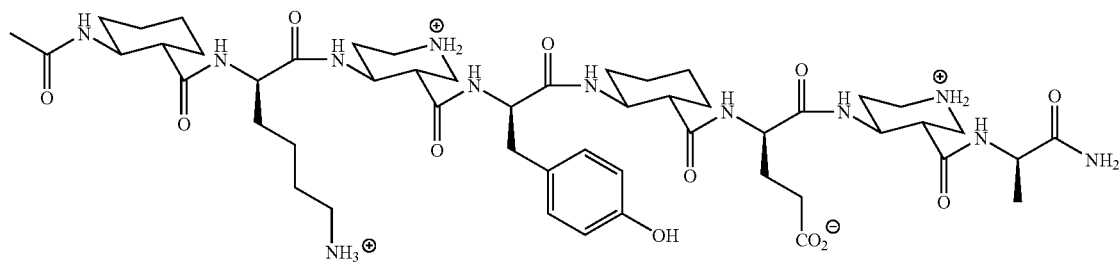

Ac-ACHC-K-PIP-Y-ACHC-E-PIP-A-NH₂
(SS) ACHC, (SS) PIP, (D) amino acids 44 (AH-III-91)

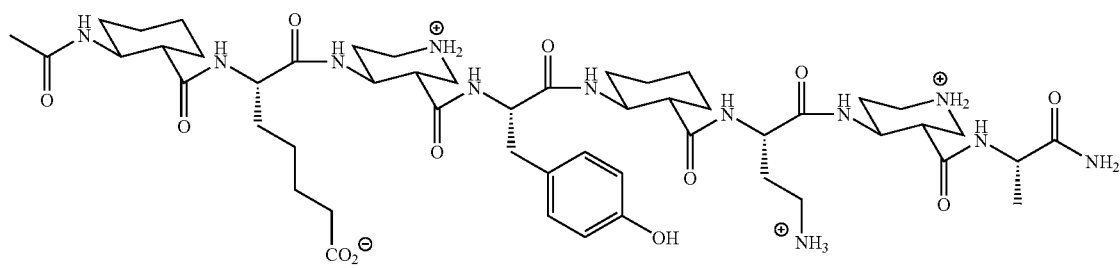

Ac-ACHC-E-PIP-Y-ACHC-K-PIP-A-HN₂
(SS) ACHC, (SS) PIP, (L) amino acids 45 (AH-III-99)

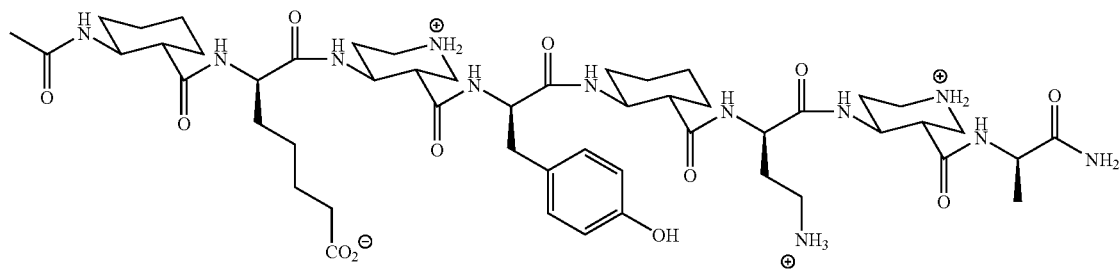

Ac-ACHC-E-PIP-Y-ACHC-K-PIP-A-NH₂
(SS) ACHC, (SS) PIP, (D) amino acids 46 (AH-III-101)

CD-spectra of compounds 43-46 (data not shown) differ from those observed for the related 5-ring peptides (38-39), a maximum occurs at a little below 200 nm and the intensity of the signals is much weaker than in those cases.

Peptides 44 and 46, comprising D-amino acids, as well as 43 and 45 with L-amino acids in the backbone, respectively, show similar CD-spectra. Curiously, for 44 and 46, signal intensity increases in methanol compared to buffer solution.

Experimental Details:

All NMR-spectra described below were obtained on a Bruker 300 MHz spectrometer and were referenced to TMS or the solvent signal.

All peptides synthesized were characterized by MALDI-TOF-MS. For HPLC purification, the solvent system A: H₂O+0.1% TFA, B: CH₃CN+0.1% TFA was used. The time program for semipreparative HPLC (C₁₈ column) usually was a close variation of: 15% B to 35% B over 30 min.

Monomers:

Methyl 3-methoxy-5-nitrobenzoate (7): Five (5) g (22 mmol) methyl 3,5-dinitrobenzoate (Aldrich) were suspended in 80 mL methanol (A.C.S. grade) and heated to reflux for app. 1 h under nitrogen, until a clear brown solution had formed. A simultaneously prepared sodium methoxide solution (prepared by portionwise addition of 0.76 g (33 mmol, 1.5 eq.) sodium to 10 mL methanol, the reaction flask was purged with nitrogen until all sodium had reacted) was added dropwise to the hot solution by syringe, each drop causing a deep red color. The reaction mixture was refluxed for an additional 15 h. After cooling to r.t., it was concentrated to dryness, the remaining brown-purple solid was taken up in 30 mL distilled water and acidified with 2 N HCl. The addition of ethyl acetate caused the present light orange solid to dissolve, phases were separated and extraction with ethyl acetate was repeated twice. The combined organic layers were washed with sat. aq. NaHCO₃, with brine, then dried with MgSO₄ and concentrated, leaving 3.7 g of a pale yellow solid. The crude product was purified by column chromatography (7:3 hexanes/ethyl acetate, $R_f$=0.6, UV; note: starting material coelutes but should be gone after the reaction time given) to afford 2.3 g (50%) of a light yellow solid. The procedure can be scaled up to 30 g starting material: depending on the course of the reaction, crude product material might be sufficiently pure to be carried on into the next step without further purification. mp 88-89° C. [2]; $^1$H NMR (CDCl$_3$) δ 8.46 (dd, J$_1$=1.5 Hz, J$_2$=2.4 Hz, 1H), 7.92 (t, J$_1$=2.4 Hz, J$_2$=2.4 Hz, 1H), 7.88 (dd, J$_1$=1.5 Hz, J$_2$=2.4 Hz, 1H), 3.99 (s, 3H, OCH$_3$), 3.95 (s, 3H, OCH$_3$); $^{13}$C NMR (CDCl$_3$) δ 164.59, 160.00, 148.95, 132.37, 120.84, 116.36, 112.65, 56.02, 52.60.

3-Hydroxy-5-nitrobenzoic acid (8): Five (5) g (23.6 mmol) 7 were dissolved in 56 mL acetic acid by heating to light reflux under nitrogen atmosphere and 82 mL aqueous hydrobromic acid (48%) were added. The yellow solution was kept under reflux for 16 h. After the reaction mixture had been concentrated, the remaining orange solid was taken up in ethyl acetate, washed with water, and brine, dried with MgSO$_4$ and concentrated again. To remove acetic acid, it was suspended in heptane and rotovapped several times. The orange solid could be recrystallized from 2 N HCl, affording 3.25 g (75%) of a yellow crystalline solid. As alternative solvent system for crystallization, ethyl acetate/hexanes can be used. The reaction can be followed by TLC: MeOH/ethyl; acetate 1:1, R$_f$ (product)=0.73. mp 194-195° C. [2]; $^1$H NMR (acetone-d$_6$) δ 8.39-8.25 (m, 1H), 7.89-7.84 (m, 2H).

iso-Pentyl 3-iso-pentyloxy-5-nitrobenzoate (9): 5.15 g (28 mmol) 8 were dissolved in 15 mL DMF (anhydrous, Aldrich) and added to a suspension of 15.5 g (112 mmol, 4 eq.) K$_2$CO$_3$ in 25 mL DMF under nitrogen atmosphere. 13.4 mL (112 mmol, 4 eq.) iso-pentyl bromide were added. The thick, canary-yellow reaction mixture was heated to 90° C. and became stirrable again. It was left at this temperature for at least 8 h. Product formation could be followed by TLC (hexanes/ethyl acetate 9:1, R$_f$ (product)=0.85). After cooling to r.t., DMF was removed with a vacuum rotovap, then ethyl acetate and water were added. After phase separation, the water layer was extracted with ethyl acetate two more times, the organics were pooled, washed with brine, dried with MgSO$_4$, concentrated and put under vacuum overnight. The crude product was purified by column chromatography (hexanes/ethyl acetate 9:1), yielding 5.15 g (80%) of a yellow liquid. $^1$H NMR (CDCl$_3$) δ 8.42 (dd, J$_1$=1.5 Hz, J$_2$=2.4 Hz, 1H), 7.90 (t, J$_1$=2.4 Hz, J$_2$=2.4 Hz, 1H),7.87 (dd, J$_1$=1.5 Hz, J$_2$=2.4 Hz, 1H), 4.40 (t, J=6.7 Hz, 2H, PhOCH$_2$CH$_2$CH(CH$_3$)$_2$), 4.11 (t, J=6.6 Hz, 2H, PhOCH$_2$CH$_2$CH(CH$_3$)$_2$), 1.93-1.65 (m, 6H), 0.99 (d, J=6.6 Hz, 12H, 2×CH(CH$_3$)$_2$); $^{13}$C NMR (CDCl$_3$) δ164.38, 159.51, 148.94, 132.69, 121.46, 116.10, 112.87, 67.40, 64.42, 37.38, 37.08, 24.97, 24.77, 22.29; ESI-MS m/z 360 [M+K−2]$^+$, 408 [M+2Na+K], 669 [M$_2$+Na]$^+$.

3-iso-Pentyloxy-5-nitrobenzoic acid (10): 4.05 g (96.6 mmol) LiOH.H$_2$O were dissolved in a mixture of 100 mL H$_2$O, 30 mL methanol and 40 mL THF. 5.2 g (16 mmol) 9 were added and it was stirred at r.t. for 20 h, during this time turning into a yellow, homogeneous solution. Most of the THF and methanol were taken off by rotovapping, the remaining solution was acidified with 2 N HCl and extracted with ethyl acetate three times. The combined organic layers were washed with brine, dried with MgSO$_4$ and put under vacuum, yielding 3.9 g (96%) of a yellow solid, which was pure by NMR. For characterization, a sample was recrystallized from ethyl acetate. mp 142° C.; $^1$H NMR (CDCl$_3$) δ 8.53 (dd, J$_1$=1.5 Hz, J$_2$=2.4 Hz, 1H), 7.98 (t, J$_1$=2.4 Hz, J$_2$=2.4 Hz, 1H), 7.94 (dd, J$_1$=1.5 Hz, J$_2$=2.4 Hz, 1H), 4.14 (t, J=6.4 Hz, 2H, PhOCH$_2$CH$_2$CH(CH$_3$)$_2$), 1.99-1.80 (m, 1H), 1.80-1.70 (m, 2H), 1.01 (d, J=6.3 Hz, 6H, CH(CH$_3$)$_2$); $^{13}$C NMR (acetone-d$_6$) δ165.52, 160.75, 150.12, 133.90, 122.35, 116.67, 113.68, 68.41, 38.33, 25.68, 22.74; ESI-MS m/z 252 [M−1]$^+$.

3-iso-Pentyloxy-5-aminobenzoic acid (11): In a hydrogenation flask, 3.9 g (15.4 mmol) acid 10 were dissolved in 50 mL methanol and while the flask was purged with nitrogen, 0.35 g Pd/C (10%) were added. The reaction mixture was shaken under a pressure of 40-50 psi for 24-36 h, then the colorless liquid was decanted off portionwise and separated from remaining catalyst by filtration through a syringe filter. Evaporation and drying under vacuum afforded 3.35 g (98%) of a brown solid, which was found to be sufficiently pure by NMR. mp 132° C.; $^1$H NMR (methanol-d$_4$) δ 8.53 (dd, J$_1$=1.4 Hz, J$_2$=2.4 Hz, 1H), 7.98 (t, J$_1$=2.3 Hz, J$_2$=2.3 Hz, 1H), 7.94 (dd, J$_1$=1.4 Hz, J$_2$=2.3 Hz, 1H), 4.14 (t, J=6.4 Hz, 2H, PhOCH$_2$CH$_2$CH(CH$_3$)$_2$), 2.14 (s, 2H), 1.92-1.75 (m, 1H), 1.69-1.60 (m, 2H), 1.01 ((d, J=6.3 Hz, 6H, CH(CH$_3$)$_2$); 13C NMR (methanol-d$_4$) δ 173.64, 164.12, 152.94, 136.89, 113.11, 109.58, 108.74, 70.08, 41.87, 28.96, 25.68; ESI-MS m/z 224 [MH]$^+$.

Benzyl 3-iso-pentyloxy-5-aminobenzoate, tosyl salt (3): 3.4 g (17.8 mmol) p-toluenesulfonic acid and 3.3 g (14.8 mmol) amino acid 11 were stirred in 30 mL benzyl alcohol at r.t. under inert gas atmosphere for 30 min. 2.82 g (17.8 mmol) p-toluenesulfonyl chloride were added to the brown solution and the mixture was heated to 80° C. for 5 h. The hot solution was poured into 230 mL diethyl ether under stirring or shaking and kept in the refridgerator for 16 h. A white precipitate formed during this time, which was filtered off and washed with ice-cold diethyl ether, yielding 6 g (84%) of tosyl salt 3. mp 168° C.; $^1$H NMR (methanol-d$_4$) δ 7.75-7.69 (m, 1H), 7.69-7.65 (m, 1H), 7.62-7.59 (m, 1H), 7.58-7.55 (m, 1H), 7.48-7.32 (m, 5H), 7.24-7.21 (m, 1H), 7.21-7.18 (m, 1H), 7.13-7.10 (m, 1H), 5.37 (s, 2H, PhCH$_2$), 4.09 (t, J=7.8 Hz, 2H, PhOCH$_2$CH$_2$CH(CH$_3$)$_2$), 2.35 (s, 3H), 1.90-1.75 (m, 1H), 1.75-1.63 (m, 2H), 0.97 (d, J=7.8 Hz, 6H, CH(CH$_3$)$_2$); ESI-MS m/z 314 [MH]$^+$.

Methyl 3-iso-pentyloxy-5-nitrobenzoate (3b): In a three-neck reaction flask with a reflux condensor attached to 2 gas wash bottles, the second one filled with NaOH$_{(aq)}$ for absorption of developing CO$_2$ and SO$_2$, 3.7 g (14.6 mmol) 3-iso-pentyloxy-5-nitrobenzoic acid (10) were dissolved in methanol and cooled to 0° C., then 1.6 mL (21.9 mmol) thionyl chloride were added dropwise under stirring. The mixture was refluxed for 4 h, then stirred overnight at r.t.. It was concentrated, then repeatedly taken up in methanol and concentrated again, and put under vacuum. Finally, 2.97 g (76%) of a red-brown liquid, which was found to be sufficiently pure by NMR, were obtained. $^1$H NMR (CDCl$_3$) δ 8.44 (dd, J$_1$=1.4 Hz, J$_2$=2.2 Hz, 1H), 7.88 (t, J$_1$=2.2 Hz, J$_2$=2.2 Hz, 1H), 7.87 (dd, J$_1$=1.4 Hz, J$_2$=2.2 Hz, 1H), 4.41 (t, J=6.8 Hz, 2H, PhOCH$_2$CH$_2$CH(CH$_3$)$_2$), 3.94 (s, 3H, OCH$_3$), 1.88-1.65 (m, 3H), 0.99 (d, J=6.6 Hz, 6H, CH(CH$_3$)$_2$).

Methyl 3-iso-pentyloxy-5-aminobenzoate (3c): Compound 3c was prepared from 3b using the same protocol as for the reduction of 7 to 2. Yield: 100%. $^1$H NMR (CDCl$_3$) δ 6.99-6.95 (m, 2H), 6.41 (t, J$_1$=2.2 Hz, J$_2$=2.2 Hz, 1H), 3.98 (t, J=6.6 Hz, 2H, PhOCH$_2$CH$_2$CH(CH$_3$)$_2$), 3.88 (s, 3H, OCH$_3$), 3.78 (sb, 2H), 1.90-1.74 (m, 1H), 1.70-1.62 (m, 2H), 0.96 (d, J=6.7 Hz, 6H, CH(CH$_3$)$_2$).

Methyl 3-methoxy-5-aminobenzoate (2): 2 g (9.5 mmol) methyl 3-methoxy-5-nitrobenzoate (7) were dissolved in 50 mL methanol by heating, then 0.3 g Pd/C (10%) were added under a stream of nitrogen, followed by 2.99 g (47.5 mmol) ammonium formate. The mixture was refluxed for 3 h, then stirred overnight at r.t.. The clear layer above the catalyst was decanted off portionwise and filtered through a syringe filter. The catalyst that remained in the flask was washed twice with methanol during this procedure. After concentration, 1.69 g of a brown solid were obtained, which were purified by column chromatography (hexanes/ethyl acetate, 7:3). Drying under vacuum afforded 1.25 g (73%) of a colorless solid. $^1$H NMR (CDCl$_3$) δ 7.00-6.97 (m, 2H), 6.42 (t, J$_1$=2.2 Hz, J$_2$=2.2

Hz), 3.89 (s, 3H, OCH$_3$), 3.80 (s, 3H, OCH$_3$), 3.78 (sb, 2H); $^{13}$C NMR (CDCl$_3$) δ 167.13 160.71, 147.49, 131.95, 109.01, 105.71, 104.36, 55.19, 51.880 ESI-MS m/z 314 [MH]$^+$.

Benzyl 3-benzyloxy-5-nitrobenzoate (12): Compound 12 was prepared from 3-hydroxy-5-nitrobenzoic acid (8), following the same protocol as for the synthesis of iso-pentyl 3-iso-pentyloxy-5-nitrobenzoate (9). Scale: 2 g (10.9 mmol) 8; 5.2 mL (43.6 mmol) benzyl bromide; 6.03 g (43.6 mmol) K$_2$CO$_3$; 15 mL DMF anhydrous. Crude yield: 6.5 g dark red oil. Column chromatography (hexanes/ethyl acetate, 9:1, R$_f$=0.5), purified yield: 2.58 g white solid (65%). $^1$H NMR (CDCl$_3$) δ 8.49 (dd, J$_1$=1.4 Hz, J$_2$=2.0 Hz, 1H), 8.01-7.98 (m, 2H), 7.49-7.34 (m, 10H), 5.41 (s, 2H, PhCH$_2$), 5.19 (s, 2H, PhCH$_2$).

Benzyl 3-benzyloxy-5-aminobenzoate (4): 2.52 g (38.5 mmol) Zn were suspended in 6 mL methylene chloride (dry, distilled), 0.9 mL (15.7 mmol) acetic acid were added and the suspension was cooled to 0° C. A solution of 0.7 g (1.93 mmol) nitrobenzoate 12 in 2 mL methylene chloride was added by syringe. After 2 h of stirring, TLC (hexanes/ethyl acetate, 7:3, R$_f$=0.4) indicated complete conversion of starting material. Zn was filtered off and the filtrate was concentrated, taken up in ethyl acetate and washed with aqueous NaHCO$_3$ three times, then with brine. After drying with MgSO$_4$ and evaporation, an orange-brown oil was obtained, which was purified by column chromatography (hexanes/ethyl acetate, 7:3) to afford 310 mg (48%) of a yellow oil. $^1$H NMR (CDCl$_3$) δ 7.50-7.27 (m, 10H), 7.12 (dd, J$_1$=1.3 Hz, J$_2$=2.2 Hz, 1H), 7.02 (dd, J$_1$=1.3 Hz, J$_2$=2.2 Hz, 1H), 6.49 (t, J$_1$=2.2 Hz, J$_2$=2.2 Hz, 1H), 5.38 (s, 2H, PhCH$_2$), 5.03 (s, 2H), 3.69 (s, 2H, PhCH$_2$).

Oligomers:

General procedure A: Boc-deprotection: Boc-protected monomers or oligomers were stirred for 1 h with 40 eq. of 4 N HCl in dioxane at r.t.. Dioxane was removed on the rotovap, the solid residue was taken up in methylene chloride and concentrated again, then mostly leaving a yellow-white solid. Yields were assumed to be quantitative and the material was taken into the coupling reaction.

General procedure B: C-terminal-deprotection, benzyl ester: Depending on other protection or functional groups that were present, benzyl esters were deprotected either by transfer hydrogenation or by hydrolysis.

Typical conditions for transfer hydrogenations were: 0.33 mmol substrate, 50 mg Pd/C (10%), 5 eq. NH$_4$HCO$_2$, 5 mL methanol. The mixture was refluxed for app. 1-3 h (TLC-control, also the reflux condensor must be carefully examined throughout this time for ammonium formate precipitation which might block this way and therefore cause pressure buildup in the reaction vessel). After cooling, it was filtered through a syringe filter, concentrated and put under vacuum. Yields were assumed to be quantitative.

Deprotection by hydrolysis was performed according to general procedure C, below, but generally extended reaction times were necessary.

General procedure C: C-terminal-deprotection, methyl ester: At 0° C., 0.33 mmol of the methyl ester were dissolved in 4 mL solvent (6:3: 1, THF/eOH/H$_2$O). 5 eq. (1.65 mmol) LiOH·H$_2$O were added and stirring was continued at 0° C. until TLC indicated complete conversion (usually at least 3 h). Methanol and THF were taken off by rotovapping, H$_2$O was added and it was extracted once with ethyl acetate, this then being discarded. The aqueous phase was acidified with 1 N HCl at 0° C., then extracted three times with ethyl acetate. The combined organics were washed with brine, and dried with MgSO$_4$. After filtration, it was concentrated, which mostly left a white solid. Yields were assumed to be quantitative.

General procedure D: C-terminal-deprotection, allylic ester: In the case of compounds 23 and 24, deprotection of an allylic ester group was necessary. This was accomplished with Pd(PPh$_3$)$_4$ as catalyst: 0.38 mmol substrate were dissolved in 8 mL THF, 2 eq. (0.77 mmol) morpholine were added, followed by a catalytic amount of Pd(PPh$_3$)$_4$. If TLC did not show conversion, the amount of catalyst was increased. For workup, the mixture was concentrated, taken up in ethyl acetate, extracted three times with 2 N HCl at 0° C., washed three times with water, dried (MgSO$_4$), concentrated, and put under vacuum. Although NMR indicated an impurity probably caused by PPh$_3$, the product was carried on and the impurity was removed by purification after the coupling procedure.

General procedure E: Peptide coupling, PyCloP-method: 0.35 mmol (1.5 eq.) PyCloP were dissolved in 2 mL solvent (preferentially methylene chloride (distilled), but at oligomer level of tetramer and higher, usage of DMF (anhydrous, Aldrich)/methylene chloride mixtures or pure DMF became necessary for solubility reasons) and cooled to 0° C. The C-deprotected fragment (0.23 mmol) was added and stirring was continued for 5 min, then the N-deprotected compound (0.23 mmol) was added, followed by 3.8 eq. (0.87 mmol) DIEA. Finally, 0.3 eq. (0.069 mmol) DMAP were added. Stirring was continued, at first at 0° C., then at r.t., for app. 1 d. Solvents were evaporated and purification was accomplished by column chromatography (hexanes/ethyl acetate or methylene chloride/methanol).

Dimer Boc-ACHC-ABA-3-(H)-OBn (15b): $^1$H NMR (CDCl$_3$) δ 8.35 (sb, 1H, amide-NH), 8.15-8.16 (m, 1H), 8.00 (d, J=8.8 Hz, 1H), 7.81 (d, J=9.1 Hz, 1H), 7.55-7.23 (m, 6H), 5.37 (s, 2H, PhCH$_2$), 4.69 (d, J=8.4 Hz, 1H, Boc-NH), 3.71-3.58 (m, 1H), 2.39-2.52 (m, 1H), 2.25-2.12 (m, 1H), 2.05-1.95 (m, 1H), 1.90-1.73 (m, 2H), 1.65-1.22 (m, 4H), 1.34 (s, 9H, C(CH$_3$)$_3$); ESI-MS m/z 475 [M+Na]$^+$.

Dimer Boc-ACHC-ABA-3-(O-iso-pentyl)-OBn (15c): $^1$H NMR (CDCl$_3$) δ 8.29 (sb, amide-NH, 1H), 7.73 (t, J=2.0 Hz , 1H), 7.60-7.62 (m, 1H), 7.47-7.30 (m, 6H), 5.34 (s, PhCH$_2$, 2H), 4.70 (d, J=7.9 Hz, Boc-NH, 1H), 4.01 (t, J=6.6 Hz, 2H, PhOCH$_2$CH$_2$CH(CH$_3$)$_2$), 3.70-3.55 (m, 1H), 2.53-2.40 (m, 1H), 2.20-2.10 (m, 1H), 2.05-1.95 (m, 1H), 1.90-1.75 (m, 3H), 1.70-1.60 (m, 2H), 1.55-1.20 (m, 5H), 1.34 (s, 9H, C(CH$_3$)$_3$); 0.95 (d, J=6.7 Hz, 6H, (CH$_3$)$_2$CH); $^{13}$C NMR (CDCl$_3$) δ171.64, 165.90, 159.41, 155.98, 139.32, 135.79, 131.12, 128.35, 128.01, 112.96, 110.96, 79.88, 66.59, 66.50, 53.17, 51.10, 37.68, 33.15, 28.10, 25.04, 24.77, 22.35; MALDI-MS m/z 561 [M+Na]$^+$, 577 [M+K]$^+$.

Tetramer Boc-[ACHC-ABA-3-(O-iso-pentyl)]$_2$-OBn (16b): $^1$H NMR (CDCl$_3$/methanol-d$_4$) δ 7.80 (sb, amide-NH, 1H), 7.64-7.62 (m, 1H), 7.59-7.54 (m, 1H), 7.52 (s, 1H), 7.43-7.33 (m, 5H), 7.29-7.24 (m, 1H), 7.10 (sb, 1H), 7.00-6.96 (m, 1H), 5.76 (d, J=8.6 Hz, Boc-NH, 1H), 5.32 (s, 2H, PhCH$_2$), 4.29-4.10 (m, 1H), 3.96 (t, J=6.6 Hz, 2H, PhOCH$_2$CH$_2$CH(CH$_3$)$_2$), 3.90 (t, J=6.6 Hz, 2H, PhOCH$_2$CH$_2$CH(CH$_3$)$_2$), 3.74-3.52 (m, 1H), 2.53-2.40 (m, 1H), 2.29-1.92 (m, 4H), 1.92-1.69 (m, 8H), 1.69-1.53 (m, 5H), 1.53-1.05 (m, 6H), 1.29 (s, 9H, C(CH$_3$)$_3$), 0.92 (d, J=6.8 Hz, 12H, 2×(CH$_3$)$_2$CH); MALDI-MS m/z 891 [M+Na]$^+$, 907 [M+K]$^+$.

Dimer Boc-α-Ala-ABA-3-(H)-OBn (13): $^1$H NMR (CDCl$_3$) δ 8.77 (sb, 1H, amide-NH), 8.02 (t, J=1.7 Hz, 1H), 7.87 (d, J=8.8 Hz, 1H), 7.52 (d, J=7.6 Hz, 1H), 7.45-7.29 (m, 6H), 5.34 (s, 2H, PhCH$_2$), 5.18 (d, J=7.4 Hz, 1H, Boc-NH), 4.42-4.26 (m, 1H, CHCH$_3$), 1.44 (s, 9H, C(CH$_3$)$_3$), 1.42 (d, 3H, CHCH$_3$).

Dimer Boc-β-Ala-ABA-3-(H)-OBn (14): $^1$H NMR (CDCl$_3$) δ 8.69 (sb, 1H, amide-NH), 8.11-8.13 (m, 1H), 7.99 (d, J=7.2 Hz, 1H), 7.80 (d, J=7.9 Hz, 1H), 7.48-7.30 (m, 6H), 5.40 (sb, 1H, Boc-NH), 5.39 (s, 2H, PhCH$_2$), 3.48 (q, J=6.1 Hz, 2H, CH$_2$NHBoc), 2.65 (t, J=6.1 Hz, 2H, CH$_2$CH$_2$NHBoc), 1.42 (s, 9H, C(CH$_3$)$_3$).

Tetramer Boc-[α-Ala-ABA-3-(H)]$_2$-OBn (13b): $^1$H NMR (CDCl$_3$/methanol-d$_4$) δ 9.80 (d, J=15.9 Hz, 1H, amide-NH), 8.22 (t, J=1.7 Hz, 1H), 8.08 (d, J=7.3 Hz, 1H), 7.92-7.86 (m, 1H), 7.84-7.72 (m, 3H), 7.56-7.50 (m, 1H), 7.46-7.26 (m, 6H), 6.19 (d, J=6.8 Hz, 1H, Boc-NH), 5.36 (s, 2H, PhCH$_2$), 4.88-4.76 (m, 1H, CHCH$_3$), 4.44-4.29 (m, 1H, CHCH$_3$), 1.59 (d, J=7.0 Hz, 3H, CHCH$_3$), 1.45 (d, J=7.0 Hz, 3H, CHCH$_3$), 1.43 (s, 9H, C(CH$_3$)$_3$); MALDI-MS m/z 611 [M+Na]$^+$, 627 [M+K]$^+$.

Tetramer Boc-[β-Ala-ABA-3-(H)]$_2$-OBn (14b): $^1$H NMR (CDCl$_3$/methanol-d$_4$) δ 8.21-8.23 (m, 1H), 7.97-7.99 (m, 1H), 7.85-7.80 (m, 1H), 7.79-7.72 (m, 1H), 7.70-7.62 (m, 1H), 7.50-7.48 (m, 1H), 7.48-7.29 (m, 7H), 6.40 (sb, 1H, Boc-NH), 5.35 (s, 2H, PhCH$_2$), 3.70 (t, 2H, CH$_2$CH$_2$), 3.39 (t, 2H, CH$_2$CH$_2$), 2.69 (t, 2H, CH$_2$CH$_2$), 2.53 (t, 2H, CH$_2$CH$_2$), 1.40 (s, 9H, C(CH$_3$)$_3$); MALDI-MS m/z 611 [M+Na]$^+$, 627 [M+K]$^+$.

Dimer Boc-ACPC-ABA-3-(O-iso-pentyl)-OBn (15): $^1$H NMR (CDCl$_3$) δ 10.31 (sb, 1H, amide-NH), 7.78 (t, J=2.0 Hz, 1H), 7.70 (sb, 1H), 7.46-7.31 (m, 6H), 5.34 (s, 2H, PhCH$_2$), 4.82 (d, J=5.1 Hz, 1H, Boc-NH), 4.13-3.98 (m, 1H), 4.02 (t, J=6.7 Hz, 2H, PhOCH$_2$CH$_2$CH(CH$_3$)$_2$), 2.90-2.80 (m, 1H), 2.35-2.22 (m, 1H), 2.11-1.95 (m, 1H), 1.90-1.63 (m, 7H), 1.46 (s, 9H, C(CH$_3$)$_3$), 0.95 (d, J=6.4 Hz, 6H, CH(CH$_3$)$_2$); $^{13}$C NMR (CDCl$_3$) δ171.97, 166.08, 159.43, 156.84, 140.27, 135.88, 131.15, 128.34, 127.94, 118.92, 112.47, 110.63, 110.09, 80.48, 66.51, 56.81, 54.41, 37.72, 33.64, 28.20, 26.73, 24.80, 22.38; MALDI-MS m/z 547 [M+Na]$^+$, 563 [M+K]$^+$.

Tetramer Boc-[ACPC-ABA-3-(O-iso-pentyl)]$_2$-OBn (16): $^1$H NMR (CDCl$_3$) δ 10.76 (sb, 1H, amide-NH), 10.44 (sb, 1H, amide-NH), 7.91 (t, J=1.6 Hz, 1H), 7.73 (t, J=2.3 Hz, 1H), 7.70 (sb, 1H), 7.49-7.43 (m, 2H), 7.41-7.28 (m, 5H), 7.19-7.15 (m, 1H), 6.43 (d, J=5.4 Hz, amide-NH), 5.36 (s, 2H, PhCH$_2$), 4.81 (d, J=5.7 Hz, 1H, Boc-NH), 4.45-4.36 (m, 1H), 4.12-4.00 (m, 1H), 4.03 (t, J=6.8 Hz, 4H, 2×PhOCH$_2$CH$_2$CH(CH$_3$)$_2$), 3.02-2.95 (m, 1H), 2.93-2.84 (m, 1H), 2.45-2.22 (m, 2H), 2.18-2.00 (m, 2H), 1.94-1.60 (m, 13H), 1.60-1.40 (m, 1H), 1.50 (s, 9H, C(CH$_3$)$_3$), 0.97 (d, J=6.5 Hz, 6H, CH(CH$_3$)$_2$), 0.95 (d, J=6.5 Hz, 6H, CH(CH$_3$)$_2$); $^{13}$C NMR (CDCl$_3$) δ172.38, 172.26, 168.65, 166.03, 159.53, 159.20, 156.75, 140.13, 135.86, 134.94, 131.02, 128.20, 127.70, 112.78, 110.35, 110.27, 109.23, 108.79, 108.48, 80.33, 66.75, 66.31, 56.88, 56.59, 54.19, 53.92, 37.64, 33.54, 33.24, 28.09, 27.04, 25.15, 24.69, 24.66, 22.27; MALDI-MS m/z 863 [M+Na]$^+$, 879 [M+K]$^+$.

Hexamer Boc-[ACPC-ABA-3-(O-iso-pentyl)]$_3$-OBn (17): $^1$H NMR (CDCl$_3$) δ 10.95 (sb, 1H, amide-NH), 10.37 (sb, 1H, amide-NH), 10.16 (sb, 1H, amide-NH), 7.93 (t, J=1.5 Hz, 1H), 7.81-7.76 (m, 1H), 7.74 (t, J=2.4 Hz, 1H), 7.49-7.40 (m, 3H), 7.38-7.22 (m, 7H), 7.14-7.10 (m, 1H), 7.30-6.80 (m, 1H), 7.02-6.98 (m, 1H), 5.34 (s, 2H, PhCH$_2$), 4.84 (d, J=4.3 Hz, 1H, Boc-NH), 4.65-4.53 (m, 1H), 4.50-4.39 (m, 1H), 4.12-3.95 (m, 1H), 4.02 (t, J=6.6 Hz, 4H, 2×PhOCH$_2$CH$_2$CH(CH$_3$)$_2$), 3.91-3.79 (m, 2H, PhOCH$_2$CH$_2$CH(CH$_3$)$_2$), 3.08-2.99 (m, 1H), 2.96-2.86 (m, 1H), 2.55-2.44 (m, 1H), 2.40-2.27 (m, 1H), 2.26-2.15 (m, 1H), 2.14-2.00 (m, 3H), 1.99-1.50 (m, 24H), 1.44 (s, 9H, C(CH$_3$)$_3$), 0.94 (d, J=6.5 Hz, 6H, CH(CH$_3$)$_2$), 0.93 (d, J=6.5 Hz, 6H, CH(CH$_3$)$_2$), 0.89 (d, J=6.5 Hz, 6H, CH(CH$_3$)$_2$); MALDI-MS m/z 1179 [M+Na]$^+$.

Octamer Boc-[ACPC-ABA-3-(O-iso-pentyl)]$_4$-OBn (18): $^1$H NMR (CDCl$_3$) δ 11.01 (sb, 1H, amide-NH), 10.01 (sb, 1H, amide-NH), 9.91 (sb, 1H, amide-NH), 9.65 (sb, 1H, amide-NH), 8.25 (sb, 1H), 7.98-7.94 (m, 1H), 7.80-7.22 (m, 14H), 7.20-7.05 (m, 1H), 7.05-6.96 (m, 1H), 6.95-6.75 (m, 2H), 5.33 (s, 2H, PhCH$_2$), 5.12 (sb, 1H, Boc-NH), 4.80-4.68 (m, 1H), 4.65-4.53 (m, 1H), 4.52-4.40 (m, 1H), 4.25-4.38 (m, 1H), 4.00-3.75 (m, 6H), 4.02 (t, J=6.6 Hz, 6H, 3×PhOCH$_2$CH$_2$CH(CH$_3$), 3.10-2.60 (m, 3H), 2.38-1.20 (m, 37H), 1.44 (s, 9H, C(CH$_3$)$_3$), 0.99-0.82 (m, 24H, 4×CH(CH$_3$)$_2$); MALDI-MS m/z 1495 [M+Na]$^+$, 1511 [M+K]$^+$, 1373 [M-Boc+2H]+

Decamer Boc-[ACPC-ABA-3-(O-iso-pentyl)]$_5$-OBn (19): $^1$H NMR (CDCl$_3$, significant signals) δ 11.08 (sb, 1H, amide-NH), 10.37 (sb, 1H, amide-NH), 10.00 (sb, 1H, amide-NH), 9.75 (sb, 1H, amide-NH), 9.09 (sb, 1H, amide-NH), 5.02 (s, 2H, PhCH$_2$), 5.22 (d, J=5.9 Hz, 1H, Boc-NH); MALDI-MS m/z 1813 [M+Na]$^+$.

Dimer Boc-ACPC-ABA-3-(O-benzyl)-OBn (20): $^1$H NMR (CDCl$_3$) δ 10.34 (sb, 1H, amide-NH), 7.89 (t, J=2.2 Hz, 1H), 7.77-7.75 (m, 1H), 7.47-7.28 (m, 11H), 5.35 (s, 2H, PhCH$_2$), 5.11 (s, 2H, PhCH$_2$), 4.77 (d, J=5.3 Hz, 1H, Boc-NH), 4.10-4.02 (m, 1H), 2.92-2.82 (m, 1H), 2.36-2.24 (m, 1H), 2.10-1.98 (m, 1H), 1.90-1.68 (m, 4H), 1.48 (s, 9H, C(CH$_3$)$_3$); MALDI-MS mn/z 567 [M+Na]$^+$, 583 [M+K]$^+$.

Tetramer Boc-[ACPC-ABA-3-(O-benzyl)]$_2$-OBn (21): $^1$H NMR (CDCl$_3$/methanol-d$_4$) δ 11.02 (s, 1H, amide-NH), 10.78 (s, 1H, amide-NH), 9.22 (d, J=7.4 Hz, 1H), 8.60 (t, J=1.5 Hz, 1H), 8.53 (t, J=2.0 Hz, 1H), 8.42-8.40 (m, 1H), 8.35-8.33 (m, 1H), 8.27-8.09 (m, 16H), 7.76 (dd, J$_1$=1.5 Hz, J$_2$=2.4 Hz, 1H), 7.74 (m, 7.99-7.95, 1H), 7.45 (d, J=8.0 Hz, 1H), 6.12 (s, 2H, PhCH$_2$), 5.93 (s, 2H, PhCH$_2$), 5.89 (s, 2H, PhCH$_2$), 5.22-5.32 (m, 1H), 4.84-4.74 (m, 1H), 3.71-3.60 (m, 1H), 3.50-3.39 (m, 1H), 2.89-2,64 (m, 4H), 2.64-2.36 (m, 7H), 2.34-2.20 (m, 1H), 2.13 (s, 9H, C(CH$_3$)$_3$); MALDI-MS m/z 904 [M+Na]$^+$, 920 [M+K]$^+$, 782 [M-Boc+2H]$^+$.

Hexamer Boc-[ACPC-ABA-3-(O-benzyl)]$_3$-OBn (22): $^1$H NMR (CDCl$_3$) δ 10.92 (s, 1H, amide-NH), 10.31 (s, 1H, amide-NH), 10.31 (s, 1H, amide-NH), 7.89-7.88 (m, 1H), 8.00-7.83 (m, 1H), 7.83-7.80 (m, 1H), 7.64 (s, 1H), 7.43-7.15 (m, 26H), 7.06 (s, 1H), 5.32 (s, 2H, PhCH$_2$), 5.07 (s, 2H, PhCH$_2$), 5.02 (s, 2H, PhCH$_2$), 4.92 (s, rotamers?, 2H, PhCH$_2$), 4.80 (s, 1H, Boc-NH), 4.71-4.60 (m, 1H), 4.50-4.40 (m, 1H), 4.14-4.05 (m, 1H), 2.96-2.86 (m, 2H), 2.40-2.30 (m, 1H), 2.30-1.40 (m, 19H); 1.41 (s, 9H, C(CH$_3$)$_3$); MALDI-MS m/z 1239 [M+Na]$^+$, 1255 [M+K]$^+$, 1117 [M-Boc+2H]$^+$.

Dimer Boc-ACPC-ABA-3-(CO$_2$Bn)-O-allyl (23): $^1$H NMR (CDCl$_3$,) δ 10.61 (s, 1H, amide-NH), 8.58 (t, J=1.8 Hz, 1H), 8.51 (t, J=1.8 Hz, 1H), 8.45 (t, J=1.4 Hz, 1H), 7.47-7.30 (m, 5H), 6.12-5.96 (m, 1H, CH$_2$CH=CH$_2$), 5.47-5.37 (m, 1H, CH$_2$CH=CHH), 5.39 (s, 2H, PhCH$_2$), 5.32-5.25 (m, 1H, CH$_2$CH=CHH), 4.87-4.78 (m, 3H, CH$_2$CH=CHH, Boc-NH), 4.12-4.03 (m, 1H), 2.94-2.85 (m, 1H), 2.40-2.25 (m, 1H), 2.12-1.98 (m, 1H), 1.93-1.69 (m, 3H), 1.54-1.39 (m, 1H), 1.50 (s, 9H, C(CH$_3$)$_3$); MALDI-MS m/z 545 [M+Na]$^+$, 561 [M+K]$^+$.

Tetramer Boc-[ACPC-ABA-3-(CO$_2$Bn)]$_2$-O-allyl (24): $^1$H NMR (CDCl$_3$) δ 10.85 (s, 1H, amide-NH), 10.59 (s, 1H, amide-NH), 8.60 (t, J=1.8 Hz, 1H), 8.58 (t, J=1.8 Hz, 1H), 8.46 (sb, 1H), 8.43 (t, J=1.6 Hz, 1H), 8.25 (sb, 1H), 8.15 (sb, 1H), 7.50-7.27 (m, 10H), 6.80 (d, J=4.1 Hz, 1H, amide-NH), 6.10-5.96 (m, 1H, CH$_2$CH=CH$_2$), 5.45-5.35 (m, 1H, CH$_2$CH=CHH), 5.39 (s, 2H, PhCH$_2$), 5.37 (s, 2H, PhCH$_2$), 5.31-5.24 (m, 1H, CH$_2$CH=CHH), 4.90-4.80 (m, 3H, CH$_2$CH=CHH, Boc-NH), 4.50-4.39 (m, 1H), 4.13-4.04 (m, 1H), 3.06-2.98 (m, 1H), 2.94-2.84 (m, 1H), 2.44-2.00 (m, 4H), 1.94-1.65 (m, 8H), 1.46 (s, 9H, C(CH$_3$)$_3$); MALDI-MS m/z 910 [M+Na]$^+$, 926 [M+K]$^+$, 788 [M-Boc+2H]$^+$.

Hexamer Boc-[ACPC-ABA-3-(CO$_2$Bn)]$_3$-O-allyl (25): $^1$H NMR (CDCl$_3$) δ 10.94 (s, 1H, amide-NH), 10.68 (s, 1H, amide-NH), 10.06 (s, 1H, amide-NH), 8.65-8.54 (m, 2H), 8.52-8.38 (m, 3H), 8.24 (s, 3H), 7.96 (s, 1H), 7.79 (s, 1H), 7.56 (sb, 1H), 7.48-7.14 (m, 15H), 6.08-5.94 (m, 1H, CH$_2$CH=CH$_2$), 5.43-5.18 (m, 8H, 3×PhCH$_2$, CH$_2$CH=CH$_2$), 4.92-4.69 (m, 4H), 4.46-4.36 (m, 1H), 4.12-4.02 (m, 1H), 3.10-2.99 (m, 1H), 2.94-2.80 (m, 1H), 2.58-2.46 (m, 1H), 2.36-2.26 (m, 1H), 2.22-1.34 (m, 18H), 1.47 (s, 9H, C(CH$_3$)$_3$); MALDI-MS m/z 1274 [M+Na]$^+$, 1290 [M+K]$^+$, 1152 [M-Boc+2H]$^+$.

Dimer Cbz-APC(Boc)-ABA-3-(OMe)-OMe (26): $^1$H NMR (CDCl$_3$) δ 9.08, 8.73 (sb (rotamers), 1H, amide-NH), 7.70 (sb, 1H), 7.64-7.58 (m, 1H), 7.40-7.30 (m, 6H), 5.29 (sb, 1H, Cbz-NH), 5.17 (s, 2H, PhCH$_2$), 4.40-4.30 (m, 1H), 3.92-3.80 (m, 1H), 3.91 (s, 3H, OCH$_3$), 3.85 (s, 3H, OCH$_3$), 3.78-3.65 (m, 2H), 3.47-3.32 (m, 1H), 3.28-3.12 (m, 1H), 1.46 (s, 9H, C(CH$_3$)$_3$); $^1$H NMR (DMSO-d$_6$) □ 10.30 (s, 1H, amide-NH), 7.85-7.81 (m, 1H), 7.72 (d, J=8.0 Hz, 1H, Cbz-NH), 7.53 (t, J=2.2 Hz, 1H), 7.35-7.25 (m, 5H), 7.16 (dd, J$_1$=1.3 Hz, J$_2$=2.5 Hz, 1H), 5.01 (s, 2H, PhCH$_2$), 4.34-4.22 (m, 1H), 3.85 (s, 3H, OCH$_3$), 3.79 (s, 3H, OCH$_3$), 3.71-3.56 (m, 2H), 3.42-3.29 (m, 1H), 3.19-3.00 (m, 2H), 1.40 (s, 9H, C(CH$_3$)$_3$); MALDI-MS m/z 550 [M+Na]$^+$, 566 [M+K]$^+$, 428 [M-Boc+2H]$^+$.

Tetramer Cbz-[APC(Boc)-ABA-3-(OMe)]$_2$-OMe (27): $^1$H NMR (CDCl$_3$) δ 9.86, 9.01 (sb, 2H, amide-NH), 7.80-7.65 (m, 1H), 7.70-7.64 (m, 1H), 7.43-7.20 (m, 7H), 7.10-6.95 (m, 2H), 5.80 (sb, 1H, Cbz-NH), 5.10 (s, 2H, PhCH$_2$), 4.75-4.59 (m, 1H), 4.56-4.41 (m, 1H), 3.88-3.60 (m, 7H), 3.90 (s, 3H, OCH$_3$), 3.83 (s, 3H, OCH$_3$), 3.79 (s, 3H, OCH$_3$), 3.40-3.15 (m, 3H), 1.47 (s, 9H, C(CH$_3$)$_3$), 1.46 (s, 9H, C(CH$_3$)$_3$); MALDI-MS m/z 911 [M+Na]$^+$, 927 [M+K]$^+$, 733 [M-Boc-C(CH$_3$)$_3$+2H]$^+$.

Tetramer Cbz-APC(Boc)-ABA-3-(OMe)-ACPC-ABA-3-(O-iso-pentyl)-OBn (28): $^1$H NMR (CDCl$_3$) δ 10.35 (sb, 1H, amide-NH), 9.20 (sb, 1H, amide-NH), 7.73 (s, 2H), 7.45-7.20 (m, 12H), 7.00 (s, 1H), 6.88 (sb, 1H), 5.67 (d, J=5.1 Hz, 1H, Cbz-NH), 5.32 (s, 2H, PhCH$_2$O$_2$C), 5.07 (s, 2H, PhCH$_2$O$_2$C), 4.52-4.34 (m, 2H), 3.97 (t, J=6.8 Hz, 2H, PhOCH$_2$CH$_2$CH (CH$_3$)$_2$), 3.82-3.60 (m, 4H), 3.74 (s, 3H, OCH$_3$), 3.38-3.08 (m, 2H), 2.98-2.89 (m, 1H), 2.32-2.18 (m, 2H), 1.96-1.58 (m, 6H), 1.44 (s, 9H, C(CH$_3$)$_3$), 0.93 (d, J=6.5 Hz, 6H, CH(CH$_3$)$_2$); MALDI-MS m/z 942 [M+Na]$^+$, 958 [M+K]$^+$, 820 [M-Boc+2H]$^+$.

Hexamer Cbz-APC(Boc)-ABA-3-(OMe)-ACPC-ABA-3-(O-iso-pentyl)-APC(Boc)-ABA-3-(OMe)-OMe (29): $^1$H NMR (CDCl$_3$/methanol-d$_4$, significant signals) δ 5.00 (s, 2H, PhCH$_2$O$_2$C), 3.87 (s, 3H, OCH$_3$), 3.80 (s, 3H, OCH$_3$), 3.76 (s, 3H, OCH$_3$), 1.45 (s, 18H, C(CH$_3$)$_3$), 0.92 (d, J=6.4 Hz, 6H, CH(CH$_3$)$_2$); MALDI-MS m/z 1228 [M+Na]$^+$, 1009 [M-Boc+2H]$^+$.

Octamer Cbz-[APC(Boc)-ABA-3-(OMe)-ACPC-ABA-3-(O-iso-pentyl)]$_2$-OBn (30): $^1$H NMR (CDCl$_3$/methanol-d$_4$, significant signals) δ 5.34 (s, 2H, PhCH$_2$O$_2$C), 5.03, 5.01 (s (rotamers?), 2H, PhCH$_2$O$_2$C), 3.77 (s, 3H, OCH$_3$), 3.75 (s, 3H, OCH$_3$), 1.47 (s, 18H, 2×C(CH$_3$)$_3$), 0.95 (d, J=6.7 Hz, 6H, CH(CH$_3$)$_2$), 0.93 (d, J=6.3 Hz, 6H, CH(CH$_3$)$_2$); MALDI-MS m/z 1620 [M+Na+4H]$^+$.

Dimer Boc-α-Lys(Cbz)-ABA-3-(H)-OMe (31): $^1$H NMR (CDCl$_3$) δ8.81 (sb, 1H, amide-NH), 8.12 (s, 1H), 7.80 (d, J=7.6 Hz, 1H), 7.73 (d, J=7.9 Hz, 1H), 7.39-7.28 (m, 6H), 5.39 (d, J=7.1 Hz, 1H, Boc-NH), 5.09 (s, 2H, PhCH$_2$), 4.97 (t, J=5.1 Hz, 1H, Cbz-NH), 4.31-4.19 (m, 1H), 3.88 (s, 3H, OCH$_3$), 3.20 (t, J. =6.5 Hz, J$_2$=6.5 Hz, 2H, CHCH$_2$R), 2.01-1.86 (m, 1H), 1.80-1.62 (m, 1H), 1.62-1.40 (m, 4H), 1.44 (s, 9H, C(CH$_3$)$_3$); MALDI-MS m/z 536 [M+Na]$^+$, 552 [M+K]$^+$.

Dimer Boc-α-Lys(Cbz)-ABA-3-(H)-OBn (31b): $^1$H NMR (CDCl$_3$) δ 8.68 (sb, 1H, amide-NH), 8.06 (s, 1H), 7.89 (d, J=7.9 Hz, 1H), 7.77 (d, J=7.6 Hz, 1H), 7.47-7.28 (m, 11H), 5.34 (s, 2H, PhCH$_2$), 5.33 (d, J=6.9 Hz, 1H, Boc-NH), 5.09 (s, 2H, PhCH$_2$), 4.91 (t, J=5.7 Hz, 1H, Cbz-NH), 4.30-4.15 (m, 1H), 3.19 (t, J$_1$=6.2 Hz, J$_2$=6.2 Hz, 2H, CHCH$_2$R), 2.02-1.87 (m, 1H), 1.79-1.62 (m, 1H), 1.61-1.40 (m, 4H), 1.43 (s, 9H, C(CH$_3$)$_3$); MALDI-MS m/z 613 [M+Na]$^+$, 629 [M+K]$^+$.

Dimer Boc-α-Tyr(OBn)-ABA-3-(H)-OMe (32): $^1$H NMR (CDCl$_3$) δ 8.07 (sb, 1H, amide-NH), 7.96 (t, J=1.8 Hz, 1H), 7.76 (d, J=7.7 Hz, 1H), 7.70 (d, J=8.2 Hz, 1H), 7.45-7.28 (m, 11H), 7.17 (s, 1H), 7.14 (s, 1H), 6.93 (s, 1H), 6.90 (s, 1H), 5.16 (d, J=7.3 Hz, 1H, Boc-NH), 5.03 (s, 2H, PhCH$_2$O), 4.53-4.39 (m, 1H, CHCH$_2$), 3.89 (s, 3H, OCH$_3$), 3.10 (s, 1H, CHCHH), 3.08 (s, 1H, CHCHH), 1.43 (s, 9H, C(CH$_3$)$_3$); MALDI-MS m/z 527 [M+Na]$^+$, 543 [M+K]$^+$.

Dimer Boc-α-Tyr(OBn)-ABA-3-(H)-OBn (32b): $^1$H NMR (CDCl$_3$) δ 8.74 (sb, 1H, amide-NH), 8.01 (t, J=1.9 Hz, 1H), 7.73 (d, J=7.8 Hz, 1H), 7.68 (d, J=8.6 Hz, 1H), 7.42-7.19 (m, 11H), 7.14 (s, 1H), 7.12 (s, 1H), 6.87 (s, 1H), 6.84 (s, 1H), 5.52 (d, J=8.1 Hz, 1H, Boc-NH), 5.30 (s, 2H, PhCH$_2$O), 4.95 (s, 2H, PhCH$_2$O), 4.66-4.51 (m, 1H, CHCH$_2$), 3.16-2.90 (m, 2H, CHCH$_2$), 1.39 (s, 9H, C(CH$_3$)$_3$); MALDI-MS m/z 604 [M+Na]$^+$, 620 [M+K]$^+$.

Tetramer Boc-α-Tyr(Cbz)-ABA-3-(H)-α-Lys(Cbz)-ABA-3-(H)-OMe (33): $^1$H NMR (CDCl$_3$, significant signals) δ 9.58 (sb, 1H, amide-NH), 9.40 (sb, 1H, amine-NH), 7.15 (s, 1H), 7.12 (s, 1H), 6.84 (s, 1H), 6.82 (s, 1H), 5.03 (s, 2H, PhCH$_2$O), 4.96 (s, 2H, PhCH$_2$O), 3.89 (s, 3H, OCH$_3$), 1.42 (s, 9H, C(CH$_3$)$_3$); MALDI-MS m/z 908 [M+Na]$^+$.

BIBLIOGRAPHY

Abele, Guichard, & Seebach (1998) "(S)-β$^3$-homolysine- and (S)-β$^3$-homoserine-containing β-peptides: CD spectra in aqueous solution," *Helv. Chim. Acta* 81:2141.

Appella, D. H.; Leplae, P. R.; Raguse, T. L.; Gellman, S. H. (2000) "(R,R,R)-2,5-Diaminocyclohexanecarboxylic Acid, a Building Block for Water-Soluble, Helix-Forming β-Peptides," *J. Org. Chem.* 65: 4766-4769.

Appella, Christianson, Karle, Powell, & Gellman (1996) "β-Peptide Foldamers: Robust Helix Formation in a New Family of β-Amino Acid Oligomers," *J. Am. Chem. Soc.* 118:13071.

Appella, Christianson, Klein, Powell, Huang, Barchi, & Gellman (1997) "Residue-Based Control of Helix Shape in β-Peptide Oligomers *Nature* 387:381.

Appella, Christianson, Karle, Powell & Gellman (1999)$^a$ "Synthesis and Characterization of trans-2-Aminocyclohexanecarboxylic Acid Oligomers: An Unnatural Secondary Structure, and Implications for β-Peptide Tertiary Structure," *J. Am. Chem. Soc.* 121:6206.

Appella, Christianson, Klein, Richards, Powell, & Gellman ($_{1999}$)$^b$ "Synthesis and Characterization of Helix-Forming β-Peptides: trans-2-aminocyclopentanecarboxylic acid oligomers," *J. Am. Chem. Soc.* 121:7574.

Barchi, Huang, Appella, Christianson, Durell, & Gellman (2000) "Solution Conformations of Helix-Forming β-Amino Acid Homooligomers," *J. Am. Chem. Soc.* 122: 2711.

Blaskovich, Lin, Delarue, Sun, Park, Coppola, Hamilton, & Sebti (2000) "Design of GFB-111, a platelet-derived growth factor binding molecule with antiangiogenic and anticancer activity against human tumors in mice," *Nature Biotechnol.* 18:1065.

Bolm, Schiffers, Dinter, & Gerlach (2000) "Practical and highly enantioselective ring opening of cyclic meso-anhydrides mediated by cinchona alkaloids," *J. Org. Chem.* 65:6984.

Bothner-By, Stephens, Lee, Warren, & Jeanloz R. W. (1984) *J. Am. Chem. Soc.* (1984) 106:811.

Braunschweiler & Ernst (1983) *J. Magn. Reson.* 53:521.

Cammers-Goodwin, Allen, Oslick, McClure, Lee, & Kemp (1996) "Mechanism of stabilization of helical conformations of polypeptides by water containing trifluoroethanol," *J. Am. Chem. Soc.* 118:3082.

Chin & Schepartz (2001) "Concerted evolution of structure and function in a miniature protein," *J. Am. Chem. Soc.* 123:2929.

Chung, Huck, Christianson, Stanger, Krauthauser, Powell & Gellman (2000) *J. Am. Chem. Soc.* 122:3995.

Cochran (2000) "Antagonists of protein-protein interactions," *Chem. Biol.* 7: R85.

Colucci, Tung, Petri & Rich (1990) *J. Org. Chem.* 55: 2895-2903.

Creighton, T. E. (1993) "Proteins: structures and molecular properties," 2nd Edition, p. 14.

Curran, Chandler, Kennedy, & Keaney (1996) "N-α-Benzoyl-cis-4-amino-L-proline: a γ-turn mimetic," *Tetrahedron Lett.* 37:1933.

Dado and Gellman (1994) *J. Am. Chem. Soc.* 116:1054-1062.

Fisk, Powell, & Gellman (2000) *J. Am. Chem. Soc.* 122:5443.

Degrado, Schneider, & Hamuro (1999) Pept. Res. 54:206.

Gellman (1998)$^a$ *Acc. Chem. Res.* 31:173.

Gellman ($_{1998}$)$^b$ "Minimal model systems for β-sheet secondary structure in proteins," *Curr. Opin. Chem. Biol.* 2:717.

Gómez-Vidal & Silverman (2001) "Short, highly efficient syntheses of protected 3-azido- and 4-azidoproline and their precursors," *Org. Lett.* 3:2481.

Goodman, Verdini, Toniolo, Phillips, & Bovey (1969) *Proc. Natl. Acad. Sci. USA* 64:444.

Gung, Zou, Stalcup, & Cottrell, (1999) "Characterization of a water-soluble, helical β-peptide," *J. Org. Chem.* 64:2176.

Hamuro et al. (1999) *J. Am. Chem. Soc.* 121:12200-12201.

Hanessian, Luo, Schaum, Michnick (1998) "Design of secondary structures in unnatural peptides: stable helical γ-tetra-, hexa-, and octapeptides and consequences of α-substitution," *J. Am. Chem. Soc.* 120:8569.

Hanessian, Luo, Schaum (1999) *Tetrahedron Lett.* 40:4925.

Herlt, Kibby, Rickards (1981) *Aust. J. Chem.* 34:1319-1324

Hintermann, Gademann, Jaun, Seebach (1998) "γ-Peptides forming more stable secondary structures than α-peptides: synthesis and helical NMR-solution structure of the γ-hexapeptide analog of H-(Val-Ala-Leu)$_2$-OH," *Helv. Chim. Acta* 81:983.

Kobayashi, Kamiyama, & Ohno (1990) "Chiral synthon obtained with pig-liver Esterase-introduction of chiral centers into cyclohexene skeleton," *Chem. Pharm. Bull.* 38:350-354.

Kobayashi, Kamiyama, & Ohno (1990) "The first enantioselective synthesis of fortamine, the 1,4-diaminocyclitol moiety of fortimicin-A, by chemicoenzymatic approach," *J. Org. Chem.* 55:1169.

Lacroix, Kortemme, Lopez do la Paz, & Serrano (1999) *Curr. Opin. Struct. Biol.* 9:487.

Lee, Syud, Wang, Gellman (2001) "Diversity in Short β-Peptide 12-Helices: High Resolution Structural Analysis in Aqueous Solution of a Hexamer Containing Sulfonylated Pyrrolidine Residues," *J. Am. Chem. Soc.* 123:7721.

LePlae, Umezawa, Lee, Gellman (2001) *J. Org. Chem.* 66:5629-5632.

Luo & Baldwin (1997) "Mechanism of helix induction by trifluoroethanol: a framework for extrapolating the helix-forming properties of peptides from trifluoroethanol/water mixtures back to water," *Biochemistry* 36:8413.

Macura & Ernst (1980) *Mol. Phys.* 41:95.

Merrifield, R. B. (1963) "Solid Phase Peptide Synthesis. I. The Synthesis of a Tetrapeptide," *J. Am. Chem. Soc.* 85:2149-2154.

Ragothama, Awasthi, Balaram, (1998) "β-Hairpin nucleation by Pro-Gly β-turns. Comparison of D-Pro-Gly and L-Pro-Gly sequences in an apolar octapeptide," *J. Chem. Soc., Perkin Trans.* 2:137.

Seebach et al. (1996)$^a$ *Helv. Chim. Acta.* 79:913-941.

Seebach et al. (1996)$^b$ *Helv. Chim. Acta.* 79:2043-2066.

Seebach & Matthews (1997) J. Chem. Soc., Chem. Commun. 2015-2022.

Seebach, Brenner, Rueping, Schweizer, Jaun (2001) "Preparation and determination of x-ray-crystal and NMR-solution structures of $\gamma^{2,3,4}$-peptides," *J. Chem. Soc., Chem. Commun.* 207.

Suhara et al. (1996) *Tetrahedron Lett.* 37(10):1575-1578

Walgers, Lee, & Cammers-Goodwin, (1998) "An indirect chaotropic mechanism for the stabilization of helix conformation of peptides in aqueous trifluoroethanol and hexafluoro-2-propanol," *J. Am. Chem. Soc.* 120:5073.

Wang, Liu, Zhang, Shan, Han, Srinivasula, Croce, Alnemri, & Huang (2000) "Structure-based discovery of an organic compound that binds Bcl-2 protein and induces apoptosis of tumor cells," *Proc. Natl. Acad. Sci. USA* 97:7124.

Woll, Lai, Guzei, Taylor, Smith, Gellman, "Parallel Sheet Secondary Structure in γ-Peptides," *J. Am. Chem. Soc.*, in press.

Zutshi, Brickner, & Chmielewski (1998) "Inhibiting the assembly of protein-protein interfaces," *Curr. Opin Chem. Biol.* 2:62.

What is claimed is:

1. An isolated, unnatural polypeptide compound of formula:

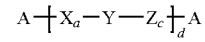

wherein:
each X and each Z is independently variable and is selected from the group consisting of α-amino acid residues, β-amino acid residues, and γ-amino acid residues, provided that at least one X or Z is an α-amino acid residue and at least another two of X or Z are two cyclically-constrained β-amino acid residues; and wherein each cyclically-constrained β-amino acid residue is independently selected from the group consisting of:

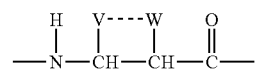

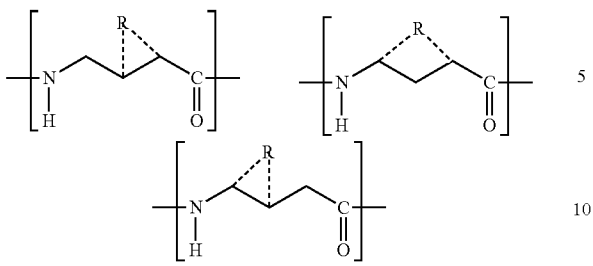

wherein V and W are combined, together with the carbon atoms to which they are bonded, and independently define a substituted or unsubstituted, monocyclic or bicyclic $C_3$-$C_{10}$ cycloalkyl, cycloalkenyl or heterocyclic ring having one or more N, O or S atom(s) as the heteroatom(s);

the substituents on carbon atoms of the rings being independently selected from the group consisting of linear, branched, or cyclic $C_1$-$C_6$-alkyl, alkenyl, alkynyl; mono- or bicyclic aryl, mono- or bicyclic heteroaryl having up to 5 heteroatoms selected from N, O, and S; mono- or bicyclic aryl-$C_1$-$C_6$-alkyl, and mono- or bicyclic heteroaryl-$C_1$-$C_6$-alkyl;

the substituents on nitrogen heteroatoms of the rings being independently selected from the group consisting of hydrogen, monocyclic or bicyclic $C_1$-$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —S(=O)$_2$—R$^{17}$, —C(=O)—R$^{17}$, —S(=O)$_2$—(CH$_2$)$_{n+1}$—R$^{18}$, and —C(=O)—(CH$_2$)$_n$—R$^{18}$, where n = 1 to 6;

wherein R$^{17}$ is independently selected from the group consisting of hydrogen, monocyclic or bicyclic $C_1$-$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein R$^{18}$ is independently selected from the group consisting of hydroxy, linear, branched, or cyclic $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl; mono- or bicyclic heteroaryl-$C_1$-$C_6$-alkyl; $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substitutent(s) is selected from the group consisting of $C_1$-$C_6$-alkyl, aryl, heteroaryl; O-alkylurethane, O-arylurethane, and O-heteroarylurethane; and wherein R$^5$ and R$^6$ are independently selected from the group consisting of hydrogen, hydroxy, linear, branched, or cyclic $C_1$-$C_{16}$-alkyl, alkenyl, or alkynyl; mono- or di-$C_1$-$C_{16}$ alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{0-6}$—NHC(=O)R$^7$, —(CH$_2$)$_{0-6}$—NHS(=O)$_2$—CH$_2$—R$^7$, —(CH$_2$)$_{0-6}$—C(=O)—OH, —(CH$_2$)$_{0-6}$—C(=O)—OR$^7$, —(CH$_2$)$_{0-6}$—C(=O)—NH$_2$, —(CH$_2$)$_{0-6}$—C(=O)—NHR$^7$, —(CH$_2$)$_{0-6}$—C(=O)—N(R$^7$)$_2$, —(CH$_2$)$_{0-6}$—O—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$—R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein R$^7$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and R$^8$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substitutent(s) is selected from the group consisting of $C_1$-$C_6$-alkyl, aryl, heteroaryl; O-alkylurethane, O-arylurethane, and O-heteroarylurethane; and wherein R$^9$ is selected from the group consisting of linear, branched, or cyclic $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH$_2$)$_{1-6}$—OR$^{11}$, —(CH$_2$)$_{1-6}$—SR$^{11}$, —(CH$_2$)$_{1-6}$—S(=O)—CH$_2$—R$^{11}$, —(CH$_2$)$_{1-6}$—S(=O)$_2$—CH$_2$—R$^{11}$, —(CH$_2$)$_{1-6}$—NR$^{11}$R$^{11}$, —(CH$_2$)$_{1-6}$—NHC(=O)R$^{11}$, —(CH$_2$)$_{1-6}$—NHS(=O)$_2$—CH$_2$—R$^{11}$, —(CH$_2$)$_{0-6}$—C(=O)—OH, —(CH$_2$)$_{0-6}$—C(=O)—

OR$^{11}$, —(CH$_2$)$_{0-6}$—C(=O)—NH$_2$, —(CH$_2$)$_{0-6}$—C(=O)—NHR$^{11}$, —(CH$_2$)$_{0-6}$—C(=O)—N(R$^{11}$)$_2$, —(CH$_2$)$_{1-6}$—O—(CH$_2$)$_{2-6}$—R$^{12}$, —(CH$_2$)$_{1-6}$—S—(CH$_2$)$_{2-6}$—R$^{12}$, —(CH$_2$)$_{1-6}$—S(=O)—(CH$_2$)$_{2-6}$—R$^{12}$, —(CH$_2$)$_{1-6}$—S(=O)$_2$—(CH$_2$)$_{2-6}$—R$^{12}$, —(CH$_2$)$_{1-6}$—NH—(CH$_2$)$_{2-6}$—R$^{12}$, —(CH$_2$)$_{1-6}$—N—{(CH$_2$)$_{2-6}$—R$^{12}$}$_2$, —(CH$_2$)$_{1-6}$—NHC(=O)—(CH$_2$)$_{2-6}$—R$^{12}$, and —(CH$_2$)$_{1-6}$—NHS(=O)$_2$—(CH$_2$)$_{2-6}$—R$^{12}$;

R$^{10}$ and R$^{13}$ are independently selected from the group consisting of hydrogen, linear, branched, or cyclic C$_1$-C$_6$-alkyl, alkenyl, or alkynyl; mono- or di-C$_1$-C$_6$ alkylamino, mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl, —(CH$_2$)$_{1-6}$—OR$^{11}$, —(CH$_2$)$_{1-6}$—SR$^{11}$, —(CH$_2$)$_{1-6}$—S(=O)—CH$_2$—R$^{11}$, —(CH$_2$)$_{1-6}$—S(=O)$_2$—CH$_2$—R$^{11}$, —(CH$_2$)$_{1-6}$—NR$^{11}$R$^{11}$, —(CH$_2$)$_{1-6}$—NHC(=O)R$^{11}$, —(CH$_2$)$_{1-6}$—NHS(=O)$_2$—CH$_2$—R$^{11}$, —(CH$_2$)$_{0-6}$—C(=O)—OH, —(CH$_2$)$_{0-6}$—C(=O)—OR$^{11}$, —(CH$_2$)$_{0-6}$—C(=O)—NH$_2$, —(CH$_2$)$_{0-6}$—C(=O)—NHR$^{11}$, —(CH$_2$)$_{0-6}$—C(=O)—N(R$^{11}$)$_2$, —(CH$_2$)$_{1-6}$—O—(CH$_2$)$_{2-6}$—R$^{12}$, —(CH$_2$)$_{1-6}$—S—(CH$_2$)$_{2-6}$—R$^{12}$, —(CH$_2$)$_{1-6}$—S(=O)—(CH$_2$)$_{2-6}$—R$^{12}$, —(CH$_2$)$_{1-6}$—S(=O)$_2$—(CH$_2$)$_{2-6}$—R$^{12}$, —(CH$_2$)$_{1-6}$—NH—(CH$_2$)$_{2-6}$—R$^{12}$, —(CH$_2$)$_{1-6}$—N—{(CH$_2$)$_{2-6}$—R$^{12}$}$_2$, —(CH$_2$)$_{1-6}$—NHC(=O)—(CH$_2$)$_{2-6}$—R$^{12}$, and —(CH$_2$)$_{1-6}$—NHS(=O)$_2$—(CH$_2$)$_{2-6}$—R$^{12}$; wherein R$^{11}$ is independently selected from the group consisting of hydrogen, C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl; and R$^{12}$ is selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$-C$_6$-alkylamino, carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of C$_1$-C$_6$-alkyl, aryl, heteroaryl; O-alkylurethane, O-arylurethane, and O-heteroarylurethane;

R$^{14}$ is selected from the group consisting of hydrogen, linear, branched, or cyclic C$_1$-C$_6$-alkyl, alkenyl, or alkynyl; mono- or di-C$_1$-C$_6$ alkylamino, mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl, —S(=O)$_2$—(CH$_2$)$_{1-6}$—R$^{11}$, —C(=O)R$^{11}$, —S(=O)$_2$—(CH$_2$)$_{2-6}$R$^{12}$, and —C(=O)—(CH$_2$)$_{1-6}$—R$^{12}$; wherein R$^{11}$ and R$^{12}$ are as defined above;

R$^{15}$ and R$^{16}$ are selected from the group listed above for R$^{10}$ and R$^{13}$, and are further selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$-C$_6$-alkylamino, carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of C$_1$-C$_6$-alkyl, aryl, heteroaryl; O-alkylurethane, O-arylurethane, and O-heteroarylurethane and each "Y" is a single bond; and "A" is independently selected from the group consisting of hydrogen and an amino-terminus protecting group, and "A'" is selected from the group consisting of hydroxy and a carboxy-terminus protecting group; and each "a," "c," and "d" is an independently variable positive integer, and wherein "a"+"c">3; or salts thereof.

2. An isolated, unnatural polypeptide compound of formula:

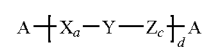

wherein:

each X and each Z is independently variable and is selected from the group consisting of α-amino acid residues, β-amino acid residues, and γ-amino acid residues, provided that at least one X or Z is an α-amino acid residue and at least another two of X or Z are two cyclically-constrained residues, the two cyclically-constrained residues being cyclically-constrained β-amino acid residues or cyclically-constrained γ-amino acid residues, or one cyclically-constrained β-amino acid residue and one cyclically-constrained γ-amino acid residue; and wherein the cyclically-constrained β-amino acid residues are selected from the group consisting of:

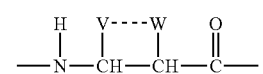

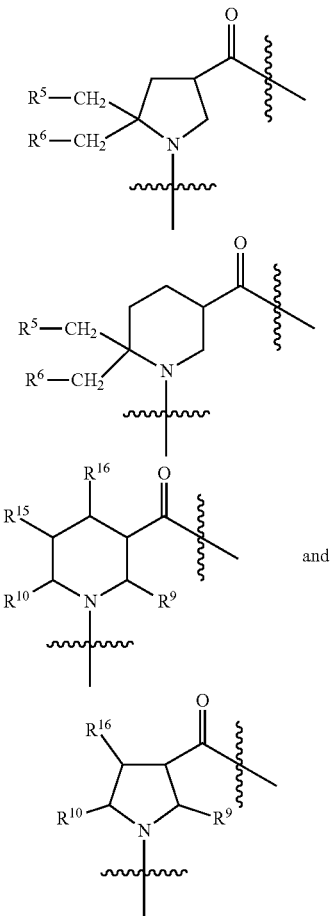

wherein V and W are combined, together with the carbon atoms to which they are bonded, and independently define a substituted or unsubstituted, monocyclic or bicyclic $C_3$-$C_{10}$ cycloalkyl, cycloalkenyl or heterocyclic ring having one or more N, O or S atom(s) as the heteroatom(s);

the substituents on carbon atoms of the rings being independently selected from the group consisting of linear, branched, or cyclic $C_1$-$C_6$-alkyl, alkenyl, alkynyl; mono- or bicyclic aryl, mono- or bicyclic heteroaryl having up to 5 heteroatoms selected from N, O, and S; mono- or bicyclic aryl-$C_1$-$C_6$-alkyl, and mono- or bicyclic heteroaryl-$C_1$-$C_6$-alkyl the substituents on nitrogen heteroatoms of the rings being independently selected from the group consisting of hydrogen, monocyclic or bicyclic $C_1$-$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —S(=O)$_2$—R$^{17}$, —C(=O)—R$^{17}$, —S(=O)$_2$—(CH$_2$)$_{n+1}$—R$^{18}$, and —C(=O)—(CH$_2$)$_n$—R$^{18}$, where n=1 to 6;

wherein R$^{17}$ is independently selected from the group consisting of hydrogen, monocyclic or bicyclic $C_1$-$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein R$^{18}$ is independently selected from the group consisting of hydroxy, linear, branched, or cyclic $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl; mono- or bicyclic heteroaryl-$C_1$-$C_6$-alkyl; $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and wherein R$^5$ and R$^6$ are independently selected from the group consisting of hydrogen, hydroxy, linear, branched, or cyclic $C_1$-$C_{16}$-alkyl, alkenyl, or alkynyl; mono- or di-$C_1$-$C_{16}$ alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{0-6}$—NHC(=O)R$^7$, —(CH$_2$)$_{0-6}$—NHS(=O)$_2$—CH$_2$—R$^7$, —(CH$_2$)$_{0-6}$—C(=O)—OH, —(CH$_2$)$_{0-6}$—C(=O)—OR$^7$, —(CH$_2$)$_{0-6}$—C(=O)—NH$_2$, —(CH$_2$)$_{0-6}$—C(=O)—NHR$^7$, —(CH$_2$)$_{0-6}$—C(=O)—N(R$^7$)$_2$, —(CH$_2$)$_{0-6}$—O—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$—R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein R$^7$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and R$^8$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane;

wherein $R^9$ is selected from the group consisting of linear, branched, or cyclic $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{1-6}$—$OR^{11}$, —$(CH_2)_{1-6}$—$SR^{11}$, —$(CH_2)_{1-6}$—S(=O)—$CH_2$—$R^{11}$, —$(CH_2)_{1-6}$—S(=O)$_2$—$CH_2$—$R^{11}$, —$(CH_2)_{1-6}$—$NR^{11}R^{11}$, —$(CH_2)_{1-6}$—NHC(=O)$R^{11}$, —$(CH_2)_{1-6}$—NHS(=O)$_2$—$CH_2$—$R^{11}$, —$(CH_2)_{0-6}$—C(=O)—OH, —$(CH_2)_{0-6}$—C(=O)—$OR^{11}$, —$(CH_2)_{0-6}$—C(=O)—$NH_2$, —$(CH_2)_{0-6}$—C(=O)—$NHR^{11}$, —$(CH_2)_{0-6}$—C(=O)—$N(R^{11})_2$, —$(CH_2)_{1-6}$—O—$(CH_2)_{2-6}$—$R^{12}$, —$(CH_2)_{1-6}$—S—$(CH_2)_{2-6}$—$R^{12}$, —$(CH_2)_{1-6}$—S(=O)—$(CH_2)_{2-6}$—$R^{12}$, —$(CH_2)_{1-6}$—S(=O)$_2$—$(CH_2)_{2-6}$—$R^{12}$, —$(CH_2)_{1-6}$—NH—$(CH_2)_{2-6}$—$R^{12}$, —$(CH_2)_{1-6}$—N—{$(CH_2)_{2-6}$—$R^{12}$}$_2$, —$(CH_2)_{1-6}$—NHC(=O)—$(CH_2)_{2-6}$—$R^{12}$, and —$(CH_2)_{1-6}$—NHS(=O)$_2$—$(CH_2)_{2-6}$—$R^{12}$; and $R^{10}$ and $R^{13}$ are independently selected from the group consisting of hydrogen, linear, branched, or cyclic $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{1-6}$—$OR^{11}$, —$(CH_2)_{1-6}$—$SR^{11}$, —$(CH_2)_{1-6}$—S(=O)—$CH_2$—$R^{11}$, —$(CH_2)_{1-6}$—S(=O)$_2$—$CH_2$—$R^{11}$, —$(CH_2)_{1-6}$—$NR^{11}R^{11}$, —$(CH_2)_{1-6}$—NHC(=O)$R^{11}$, —$(CH_2)_{1-6}$—NHS(=O)$_2$—$CH_2$—$R^{11}$, —$(CH_2)_{0-6}$—C(=O)—OH, —$(CH_2)_{0-6}$—C(=O)—$OR^{11}$, —$(CH_2)_{0-6}$—C(=O)—$NH_2$, —$(CH_2)_{0-6}$—C(=O)—$NHR^{11}$, —$(CH_2)_{0-6}$—C(=O)—$N(R^{11})_2$, —$(CH_2)_{1-6}$—O—$(CH_2)_{2-6}$—$R^{12}$, —$(CH_2)_{1-6}$—S—$(CH_2)_{2-6}$—$R^{12}$, —$(CH_2)_{1-6}$—S(=O)—$(CH_2)_{2-6}$—$R^{12}$, —$(CH_2)_{1-6}$—S(=O)$_2$—$(CH_2)_{2-6}$—$R^{12}$, —$(CH_2)_{1-6}$—NH—$(CH_2)_{2-6}$—$R^{12}$, —$(CH_2)_{1-6}$—N—{$(CH_2)_{2-6}$—$R^{12}$}$_2$, —$(CH_2)_{1-6}$—NHC(=O)—$(CH_2)_{2-6}$—$R^{12}$, and —$(CH_2)_{1-6}$—NHS(=O)$_2$—$(CH_2)_{2-6}$—$R^{12}$; wherein $R^{11}$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and $R^{12}$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane;

$R^{14}$ is selected from the group consisting of hydrogen, linear, branched, or cyclic $C_1$-$C_6$-alkyl, alkenyl, or alkynyl; mono- or di-$C_1$-$C_6$ alkylamino, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —S(=O)$_2$—$(CH_2)_{1-6}$—$R^{11}$, —C(=O)$R^{11}$, —S(=O)$_2$—$(CH_2)_{2-6}R^{12}$, and —C(=O)—$(CH_2)_{1-6}$—$R^{12}$; wherein $R^{11}$ and $R^{12}$ are as defined above;

$R^{15}$ and $R^{16}$ are selected from the group listed above for $R^{10}$ and $R^{13}$, and are further selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and wherein the cyclically-constrained γ-amino acid residues are selected from the group consisting of:

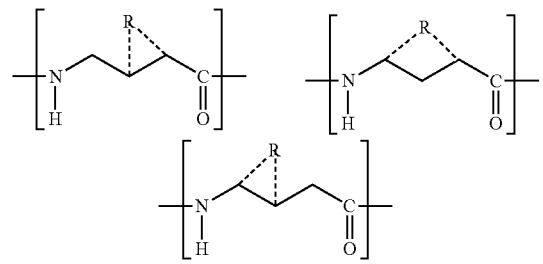

wherein R, together with the carbons to which it is attached, and further together with the β-position carbon in the γ-amino acid backbone where appropriate, independently defines a substituted or unsubstituted, monocyclic or bicyclic $C_3$ to $C_{10}$ cycloalkyl, cycloalkenyl, or heterocycle moiety, the heterocycle moiety having 1, 2, or 3 heteroatoms selected from the group consisting of N, S, and O; and each "Y" is a single bond; and "A" is independently selected from the group consisting of hydrogen and an amino-terminus protecting group, and "A'" is selected from the group consisting of hydroxy and a carboxy-terminus protecting group; and each "a," "c," and "d" is an independently variable positive integer, and wherein "a"+"c">3; or salts thereof.

3. The compound of claim 2, wherein at least one of X or Z is a cyclically-constrained β-amino acid residue wherein V and W, and the carbon atoms to which they are bonded, define a substituted or unsubstituted $C_4$ to $C_6$ cycloalkyl, cycloalkenyl, or heterocyclic ring having one nitrogen atom as the sole heteroatom.

4. The compound of claim 2, wherein at least one of X or Z is a cyclically-constrained β-amino acid residue wherein V and W, and the carbon atoms to which they are bonded, define a substituted or unsubstituted cyclopentyl, cyclohexyl, pyrrolidinyl, or piperdinyl ring.

5. A method of disrupting or mimicking binding interactions between two protein molecules or fragments thereof, the method comprising:

in an in vivo, in vitro, or ex vivo reaction between the two proteins or fragments thereof, (a) introducing to the reaction an unnatural polypeptide compound according to claim 1; and then (b) quantifying the effect of the added compound from step (a) on thermodynamic or kinetic parameters of the binding interaction between the two protein molecules or fragments thereof.

\* \* \* \* \*